(12) United States Patent
Dimitrov et al.

(10) Patent No.: US 10,604,582 B2
(45) Date of Patent: Mar. 31, 2020

(54) ANTI-CD276 ANTIBODIES (B7H3)

(71) Applicants: THE UNITED STATES OF AMERICA, as represented by THE SECRETARY, DEPARTMENT OF HEALTH, Bethesda, MD (US); BIOMED VALLEY DISCOVERIES, INC., Kansas City, MO (US)

(72) Inventors: Dimiter S. Dimitrov, Frederick, MD (US); Zhongyu Zhu, Frederick, MD (US); Bradley St. Croix, Frederick, MD (US); Steven Seaman, Martinsburg, WV (US); Saurabh Saha, Wellesley Hills, MA (US); Xiaoyan Michelle Zhang, Lexington, MA (US); Gary A. DeCrescenzo, Parkville, MO (US); Dean Welsch, Parkville, MO (US)

(73) Assignees: The United States Of America, as represented by The Secretary, Department of Health, Bethesda, MD (US); Biomed Valley Discoveries, Inc., Kansas City, MO (US)

( * ) Notice: Subject to any disclaimer, the term of this patent is extended or adjusted under 35 U.S.C. 154(b) by 33 days.

(21) Appl. No.: 15/512,000

(22) PCT Filed: Sep. 16, 2015

(86) PCT No.: PCT/US2015/050365
§ 371 (c)(1),
(2) Date: Mar. 16, 2017

(87) PCT Pub. No.: WO2016/044383
PCT Pub. Date: Mar. 24, 2016

(65) Prior Publication Data
US 2018/0186890 A1 Jul. 5, 2018

Related U.S. Application Data

(60) Provisional application No. 62/051,650, filed on Sep. 17, 2014.

(51) Int. Cl.
| | | |
|---|---|---|
| C07K 16/30 | (2006.01) | |
| C07K 16/28 | (2006.01) | |
| A61K 39/395 | (2006.01) | |
| A61K 47/68 | (2017.01) | |
| A61K 35/00 | (2006.01) | |
| A61K 39/00 | (2006.01) | |
| G01N 33/574 | (2006.01) | |
| A61P 35/00 | (2006.01) | |

(52) U.S. Cl.
CPC ........ *C07K 16/30* (2013.01); *A61K 39/39558* (2013.01); *A61K 47/6803* (2017.08); *A61K 47/6849* (2017.08); *A61K 47/6851* (2017.08); *A61P 35/00* (2018.01); *C07K 16/2827* (2013.01); *G01N 33/57492* (2013.01); *A61K 2039/505* (2013.01); *A61K 2300/00* (2013.01); *C07K 2317/24* (2013.01); *C07K 2317/622* (2013.01); *C07K 2317/92* (2013.01); *G01N 2333/70532* (2013.01)

(58) Field of Classification Search
None
See application file for complete search history.

(56) References Cited

U.S. PATENT DOCUMENTS

| | | |
|---|---|---|
| 3,832,253 A | 8/1974 | DiPalma et al. |
| 3,854,480 A | 12/1974 | Zaffaroni |
| 4,235,871 A | 11/1980 | Papahadjopoulos et al. |
| 4,450,150 A | 5/1984 | Sidman |
| 4,452,775 A | 6/1984 | Kent |
| 4,501,728 A | 2/1985 | Geho et al. |
| 4,667,014 A | 5/1987 | Nestor, Jr. et al. |
| 4,748,034 A | 5/1988 | de Rahm |
| 4,837,028 A | 6/1989 | Allen |
| 4,892,827 A | 1/1990 | Pastan et al. |
| 5,019,369 A | 5/1991 | Presant et al. |
| 5,075,109 A | 12/1991 | Tice et al. |
| 5,225,539 A | 7/1993 | Winter |
| 5,239,660 A | 8/1993 | Ooi |
| 5,449,752 A | 9/1995 | Fujii et al. |
| 5,512,658 A | 4/1996 | Pastan et al. |
| 5,545,806 A | 8/1996 | Lonberg et al. |
| 5,569,825 A | 10/1996 | Lonberg et al. |
| 5,585,089 A | 12/1996 | Queen et al. |
| 5,602,095 A | 2/1997 | Pastan et al. |
| 5,608,039 A | 3/1997 | Pastan et al. |
| 5,639,641 A | 6/1997 | Pedersen et al. |
| 5,693,761 A | 12/1997 | Queen et al. |
| 5,714,352 A | 2/1998 | Jakobovits |
| 5,821,238 A | 10/1998 | Pastan et al. |
| 5,854,044 A | 12/1998 | Pastan et al. |

(Continued)

FOREIGN PATENT DOCUMENTS

| | | |
|---|---|---|
| EP | 0239400 B1 | 9/1987 |
| EP | 2703486 A1 | 5/2014 |

(Continued)

OTHER PUBLICATIONS abstract of Gardiner et al, Journal of Clinical Oncology, 2017, abstract e14059 (Year: 2017).*

(Continued)

*Primary Examiner* — Karen A. Canella
(74) *Attorney, Agent, or Firm* — Bryan Cave Leighton Paisner LLP

(57) ABSTRACT

Polypeptides and proteins that specifically bind to and immunologically recognize CD276 are disclosed. Chimeric antigen receptors (CARs), anti-CD276 binding moieties, nucleic acids, recombinant expression vectors, host cells, populations of cells, pharmaceutical compositions, and conjugates relating to the polypeptides and proteins are also disclosed. Methods of detecting the presence of (a) cancer or (b) tumor vasculature in a mammal and methods of (a) treating or preventing cancer or (b) reducing tumor vasculature in a mammal are also disclosed.

37 Claims, 16 Drawing Sheets
Specification includes a Sequence Listing.

(56) References Cited

U.S. PATENT DOCUMENTS

| | | |
|---|---|---|
| 6,265,150 B1 | 7/2001 | Terstappen et al. |
| 2002/0197266 A1 | 12/2002 | Debinski |
| 2003/0198638 A1 | 10/2003 | Watkins |
| 2010/0215656 A1 | 8/2010 | Pastan et al. |
| 2012/0294796 A1 | 11/2012 | Johnson et al. |

FOREIGN PATENT DOCUMENTS

| | | |
|---|---|---|
| GB | 2188638 A | 10/1987 |
| WO | 2008116219 A2 | 9/2008 |
| WO | 2011109400 A2 | 9/2011 |
| WO | 2012041234 A1 | 4/2012 |
| WO | 2012079000 A1 | 6/2012 |
| WO | 2012147713 A1 | 11/2012 |
| WO | 2013059593 A1 | 4/2013 |
| WO | 2014011518 A1 | 1/2014 |

OTHER PUBLICATIONS

Loo, D., et al. Development of an Fc-enhanced anti-B7-H3 monoclonal antibody with potent antitumor activity. Clin Cancer Res. Jul. 15, 2012;18(14):3834-45.

Orentas, R.J., et al. Identification of cell surface proteins as potential immunotherapy targets in 12 pediatric cancers. Front Oncol. Dec. 17, 2012;2:194.

Rudikoff, S., et al. Single amino acid substitution altering antigen-binding specificity. Proc Natl Acad Sci U S A. Mar. 1982; 79(6): 1979-1983.

Colman, P.M., Effects of amino acid sequence changes on antibody-antigen interactions. Res Immunol. Jan. 1994;145(1):33-36.

Abaza, M.S., et al. Effects of amino acid substitutions outside an antigenic site on protein binding to monoclonal antibodies of predetermined specificity obtained by peptide immunization: demonstration with region 94-100 (antigenic site 3) of myoglobin. J Protein Chem. Oct. 1992;11(5):433-444.

Gussow, D. and Seemann, G., Humanization of monoclonal antibodies. Methods in Enzymology (1991) 203:99-121.

Ibragimova, G.T. and Wade, R.C., Stability of the beta-sheet of the WW domain: A molecular dynamics simulation study. Biophys J. Oct. 1999;77(4):2191-8.

Gura, T., Systems for identifying new drugs are often faulty. Science. Nov. 7, 1997;278(5340):1041-2.

Chames, P., et al. Therapeutic antibodies: successes, limitations and hopes for the future. Br J Pharmacol. May 2009;157(2):220-33.

Byers, T., What can randomized controlled trials tell us about nutrition and cancer prevention? CA Cancer J Clin. Nov.-Dec. 1999;49(6):353-61.

Violette, P.D. and Saad, F., Chemoprevention of prostate cancer: myths and realities. J Am Board Fam Med. Jan.-Feb. 2012;25(1):111-9.

Jemal, A., et al., Cancer Incidence, Mortality, and Associated Risk Factors Among Asian Americans of Chinese, Filipino, Vietnamese, Korean, and Japanese Ethnicities, CA: A Cancer Journal for Clinicians, 57: 43-66 (2007).

Choi, N. W., et al. Synthesis and assembly of a cholera toxin B subunit-rotavirus VP7 fusion protein in transgenic potato, Mol. Biotechnol. 31: 193-202 (2005).

Kohler, G., et al., Derivation of specific antibody-producing tissue culture and tumor lines by cell fusion, Eur. J. Immunol. Jul. 1976;6(7):511-9.

Greenfield, E. A. (ed.), Antibodies: A Laboratory Manual, Second Edition: Generating Monoclonal Antibodies Successful Plating Strategies, CSH Press (2013).

Murphy, K., et al., (ed) Janeway's Immunobiology, 8th Ed., Taylor & Francis, Incl, NY, NY (2011).

Haskard, D.O., et al., The production of human monoclonal autoantibodies form patients with rheumatoid arthritis by the EBV-hybridoma technique, Journal of Immunology Methods, vol. 74, Issue 2, 361-637 (1984).

Green, M. R., et al., Molecular Cloning: A Laboratory Manual, 4th Ed., vol. 1, CSH Lab Press, New York (2012).

Ausubel, F. M., et al., Current Protocols in Molecular Biology, Green Publishing Associates and John Wiley & Sons, NY (2007).

Pedersen, J. T., et al., Comparison of Surface Accessible Residues in Human and Murine Immunoglobulin Fv Domains: Implication for Humanization of Murine Antibodies, Journal of Molecular Biology, vol. 235, Issue 3, 959-973 (1994).

Chan, W. C., et al., Fmoc Solid phase peptide synthesis, A Practical Approach, Oxford Univ. Press, Oxford, UK 2001.

Reid, R. E., et al., Peptide and Protein Drug Analysis, ed., New York : M. Dekker, 2000.

Westwood, O.M.R., et al., An Introduction to Epitope Mapping, ed., Oxford Univ. Press, UK 200.0.

Hudecz, F., Peptide Synthesis and Applications, Methods in Mol. Bio., 298: 209-223 (2005).

Kirin, S. I., et al., Amino Acid and Peptide Bioconjugates of Copper(II) and Zinc(II) Complexes with a Modified N,N-Bis(2-picolyl)amine Ligand, Inorg. Chem., 2005, 44 (15), pp. 5405-5415.

Graham, F. L, et al., A technique for the assay of infectivity of human adenovirus 5 DNA, Virology, 52: 456-467 (1973).

Davis, L.G., et al., Basic Methods in Molecular Biology, Elsevier (1986).

Chu, G., et al., SV40 DNA transfection of cells in suspension: analysis of the efficiency of transcription and translation of T-antigen, 13: 97 (1981).

Capecchi, M. R., High efficiency transformation by direct microinjection of DNA into cultured mammalian cellsCell, 22:479-488 (1980).

Shigekawa, BioTechniques, 6:742-751 (1988).

Mannino, RJ, et al., Liposome mediated gene transfer, BioTechniques, Jul. 1, 1988, 6(7):682-690.

Felgner, P.L., et al., Lipofection: a highly efficient, lipid-mediated DNA-transfection procedure, Proc. Natl. Acad. Sci. USA, vol. 84, No. 21, pp. 7413-7417 (Nov. 1, 1987).

Klein, T.M., et al., High-velocity microprojectiles for delivering nucleic acids into living cells, Nature 327, 70-73, (1987).

Springer, C.J., et al., Suicide Gene Therapy: Methods and Reviews, (Cancer Research UK Centre for Cancer Therapeutics at the Institute of Cancer Research, Humana Press 2004.

Remington, The Science and practice of pharmacy, 21 Ed., Lippincott Williams and Wilkins, Philadelphia, PA, 2005.

Thompson, J.E., et al., A Practical Guide to Contemporary Pharmacy Practice, Lippincott Williams & Wilkins, Phil., PA, 2009.

Trissel, L. A., Handbook on Injectable Drugs,16th Ed., 2010.

Szoka, F., Jr., et al., Comparative Properties and Methods of Preparation of Lipid Vesicles (Liposomes), Annu. Rev. Biophys. Bioeng. 1980, 9:457-508.

Clay, T.M., et al., Efficient Transfer of a Tumor Antigen-Reactive TCR to Human Peripheral Blood Lymphocytes Confers Anti-Tumor Reactivity, Journal of Immunology, J Immunol 1999; 163:507-513.

Zhao, Y., et al., Primary human lymphocytes transduced with NY-ESO-1 antigen-specific TCR genes recognize and kill diverse human tumor cell lines, Journal of Immunology, vol. 174, Issue 7, Apr. 1, 2005.

Roder, JC., et al., The EBV-hybridoma technique, Methods Enzymol. 1986;121:140-67.

Reiter, Y., et al., Engineering interchain disulfide bonds into conserved framework regions of Fv fragments: improved biochemical characteristics of recombinant immunotoxins containing disulfide-stabilized Fv, Protein Engineering, vol. 7, Issue 5, pp. 697-704, May 1994.

International Preliminary Report on Patentability and Written Opinion from the International Searching Authority, dated Mar. 21, 2017.

Kwok, et al. "Development of a 'mouse and human cross-reactive' affinity-matured exosite inhibitory human antibody specific to TACE (ADAM17) for cancer immunotherapy," Protein Engineering Design and Selection vol. 27 No. 6 pp. 179-190 (2014).

Communication from EP 15 772 128.3 dated May 11, 2018.

\* cited by examiner

ANTI-CD276 ANTIBODIES (B7H3)

CROSS-REFERENCES TO RELATED APPLICATIONS

The present application is the National Stage of International Application No. PCT/US2015/050365, filed on Sep. 16, 2015 which claims benefit to U.S. Provisional Application No. 62/051,650, filed Sep. 17, 2014. The entire contents of the above applications are incorporated by reference as if recited in full herein.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: one 36,286 Byte ASCII (Text) file named "721482_ST25.txt," dated Sep. 16, 2015.

BACKGROUND OF THE INVENTION

Cancer is a public health concern. Despite advances in treatments such as chemotherapy, the prognosis for many cancers, including solid tumors, may be poor. It is estimated that about 559,650 Americans will die from cancer, corresponding to 1,500 deaths per day (Jemal et al., *CA Cancer J. Clin.*, 57:43-66 (2007)). Accordingly, there exists an unmet need for additional treatments for cancer, particularly solid tumors.

BRIEF SUMMARY OF THE INVENTION

An embodiment of the invention provides a polypeptide comprising (i) SEQ ID NOs: 1-6, (ii) SEQ ID NOs: 11-16, or (iii) SEQ ID NOs: 20-25.

Another embodiment of the invention provides a protein comprising a first polypeptide chain comprising (i) SEQ ID NOs: 1-3, (ii) SEQ ID NOs: 11-13, or (iii) SEQ ID NOs: 20-22 and a second polypeptide chain comprising (i) SEQ ID NOs: 4-6, (ii) SEQ ID NOs: 14-16, or (iii) SEQ iD NOs: 23-25.

Another embodiment of the invention provides a conjugate comprising

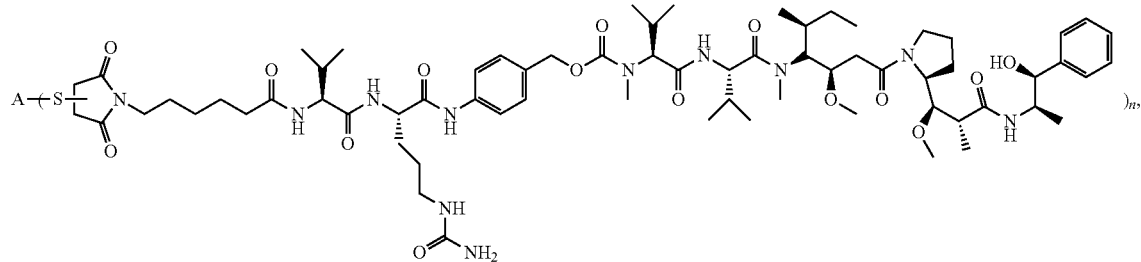

wherein:
n is an even integer, and
A is an anti-CD276 binding moiety comprising the amino acid sequences of SEQ ID NOs: 26 and 27.

Further embodiments of the invention provide related anti-CD276 binding moieties, nucleic acids, recombinant expression vectors, host cells, populations of cells, conjugates, kits, and pharmaceutical compositions relating to the polypeptides and proteins of the invention.

Additional embodiments of the invention provide methods of detecting the presence of (a) cancer or (b) tumor vasculature in a mammal and methods of treating or preventing cancer or (b) reducing tumor vasculature in a mammal.

or transduced to express mouse CD276 (CHO-msCD276) or human CD276 (CHO-huCD276).

Figure 5:
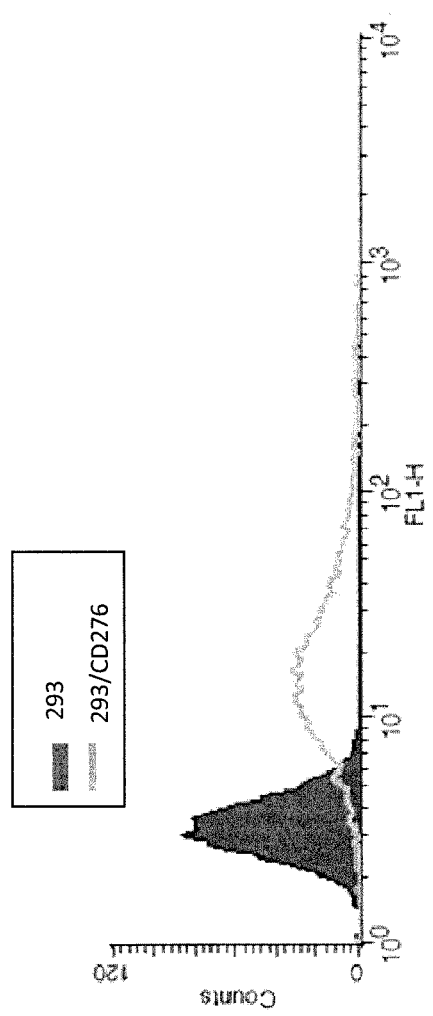

FIG. 5 is a graph showing the number of counts measured by flow cytometry indicating the level of binding of FITC-labeled human anti-CD276 antibody m8524 IgG1 to human embryonic kidney (HEK) cells that were untransduced (293) (shaded peak) or transduced to express human CD276 (293/CD276) (unshaded peak).

Figure 6:
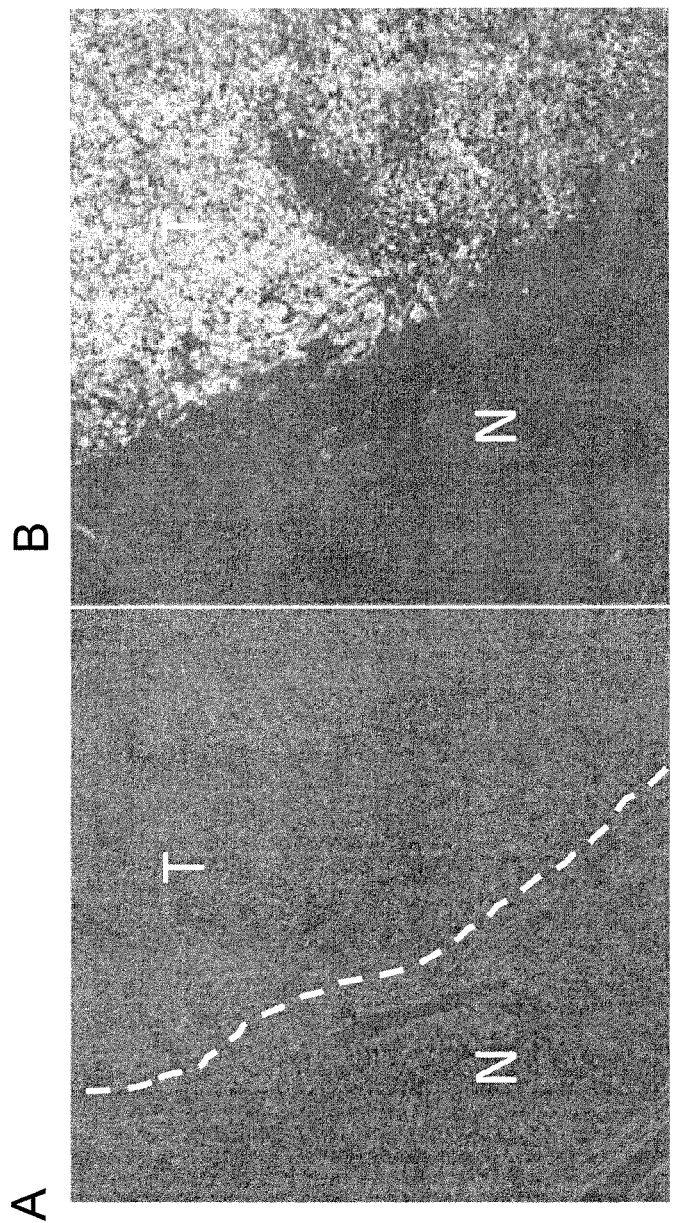

FIGS. 6A and 6B are photographic images of a sample of the normal liver/tumor margin of MC38 colon cancer tumor-bearing mice stained with laminin (FIG. 6A) or FITC-labeled human anti-CD276 antibody (m8524) (FIG. 6B). N=normal liver; T=tumor.

Figure 7:
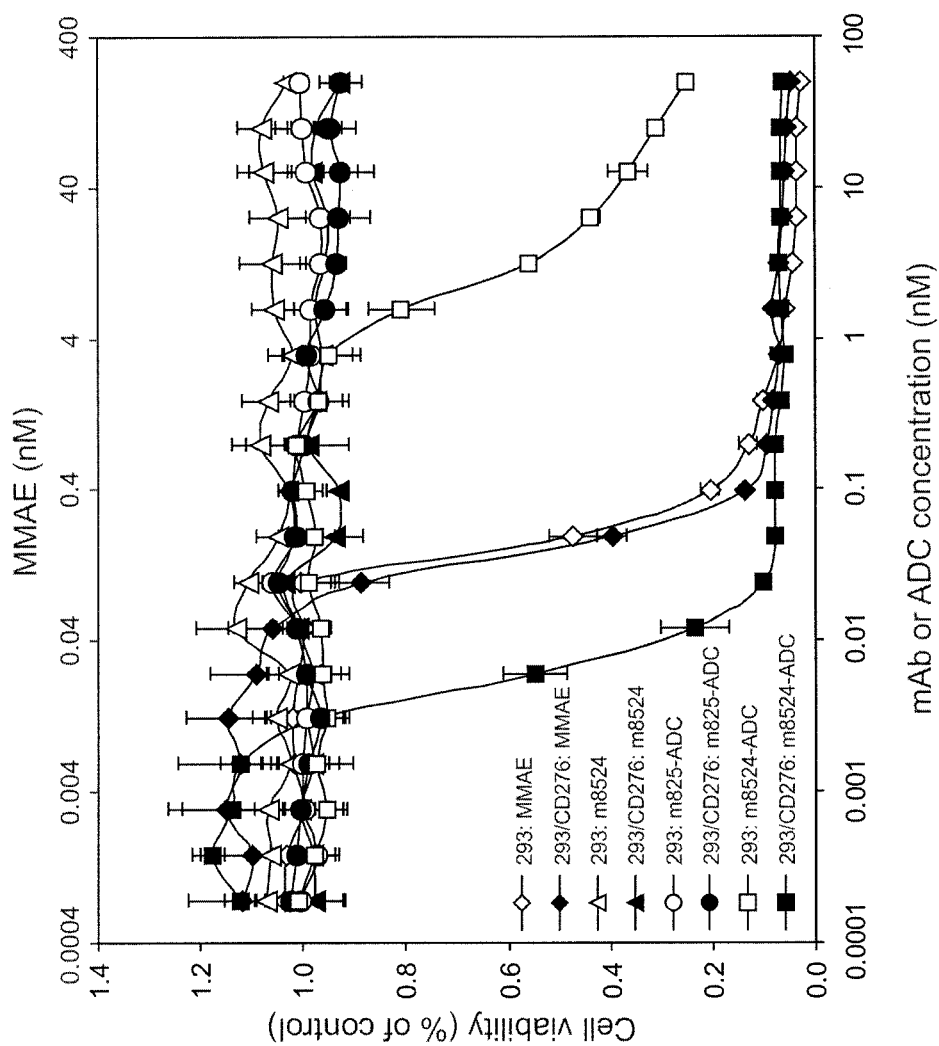

FIG. 7 is a graph showing cell viability (% of control) of 293 cells treated with monomethyl auristatin E (MMAE) (open diamonds), m276 (m8524) (open triangles), m825 (irrelevant control antibody)-antibody drug conjugate (ADC) (open circles), or m8524-ADC (open squares) and 293 cells transduced with CD276 (293/CD276) treated with MMAE (closed diamonds), m8524 (closed triangles), m825-ADC (closed circles), or m8524-ADC (closed squares) at various concentrations (nM) of MMAE and monoclonal antibody (mAb) or ADC.

Figure 8:
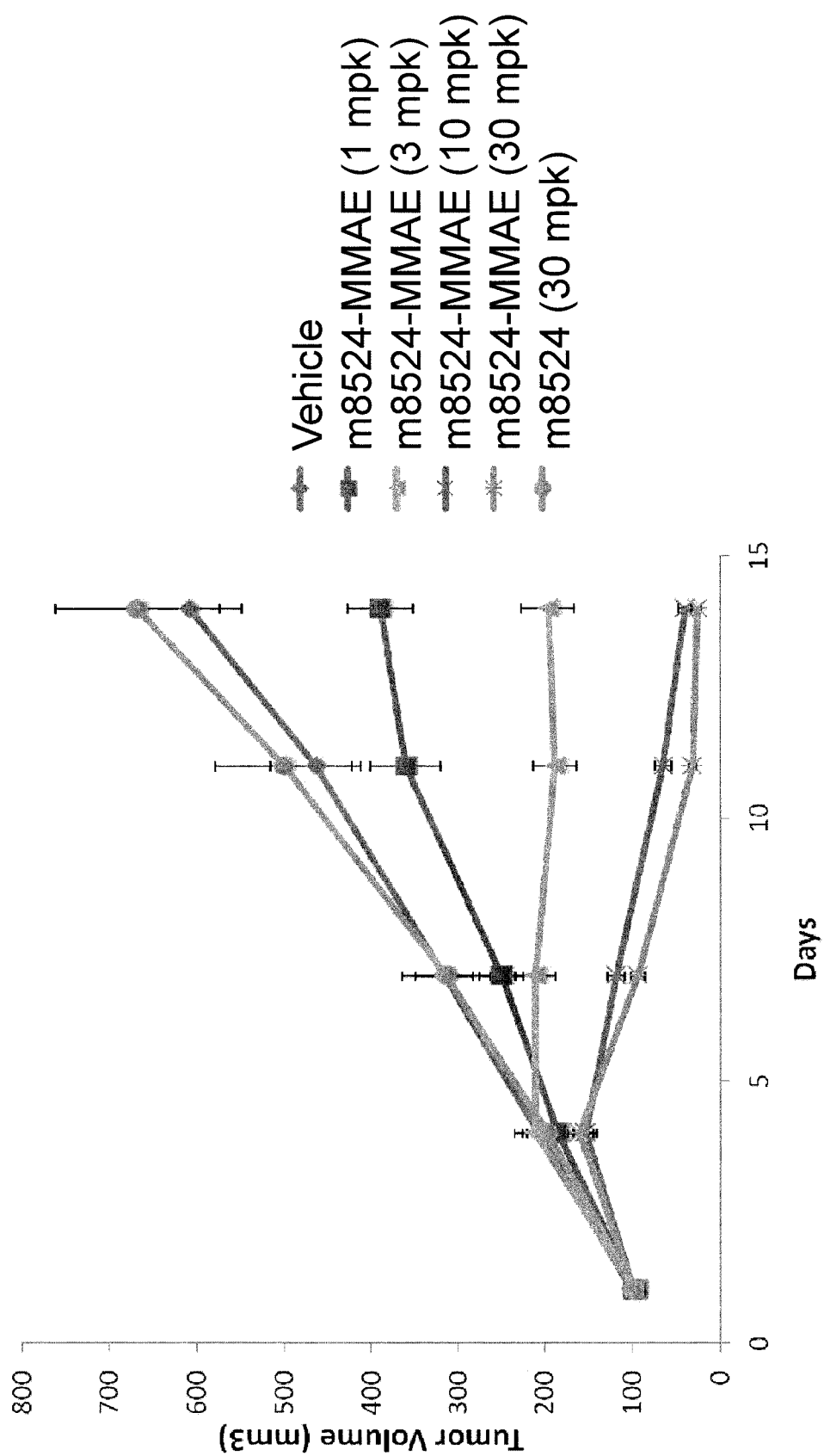
Figure 9:
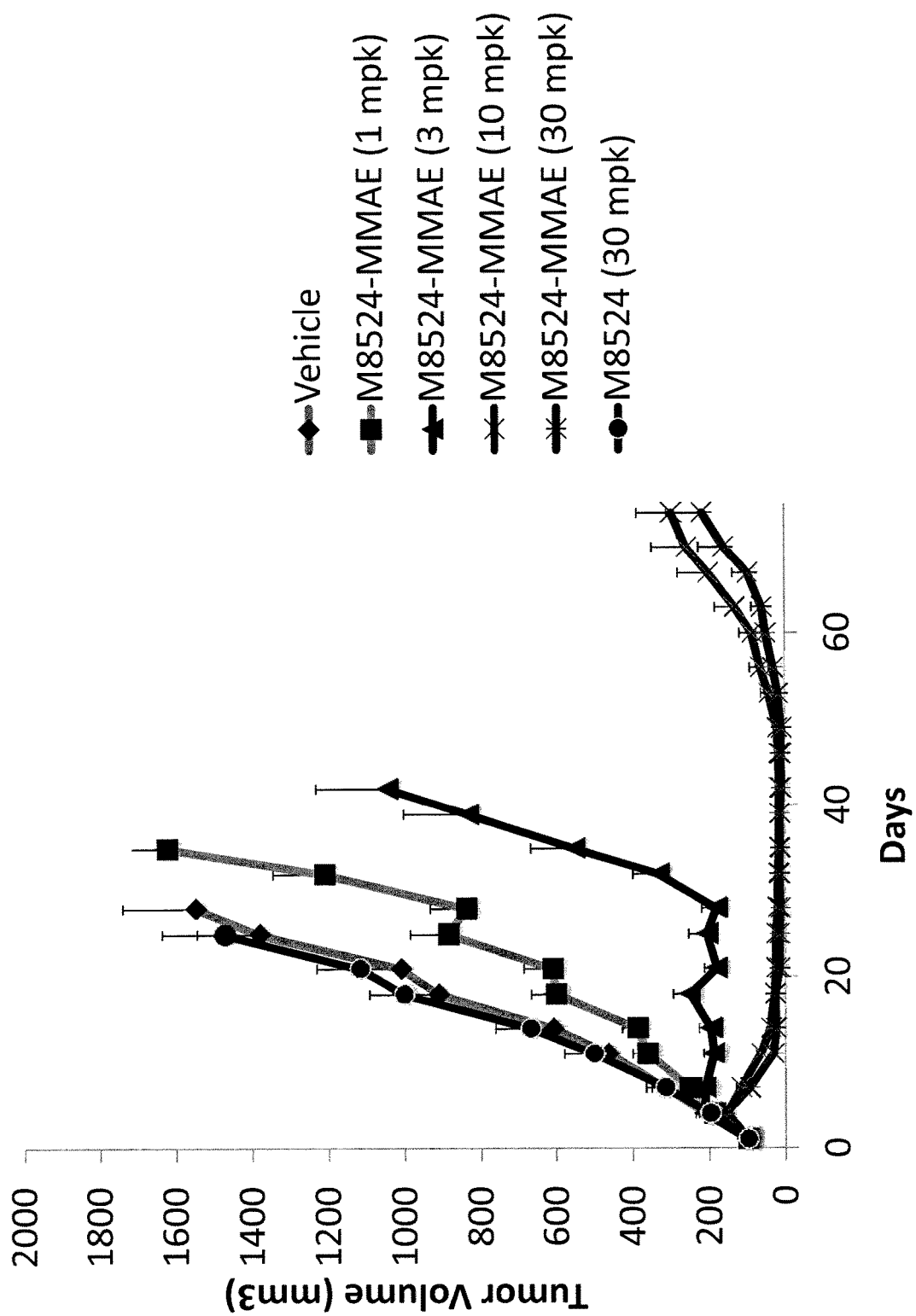

FIGS. 8 and 9 are graphs showing the tumor volume (mm$^3$) in HCT-116 tumor bearing mice treated with control (vehicle) (diamonds), m8524 (M276) alone (30 mg/kg (mpk)) (circles), or m8524 (m276)-MMAE ADCs at various dosages (1 mpk (squares), 3 mpk (triangles), 10 mpk (x), or 30 mpk (*)) at various time points (days) up to about 15 days (FIG. 8) and up to about 75 days (FIG. 9) after administration. In FIG. 8, the compositions were administered on days 1, 4, 7, and 11.

Figure 10:
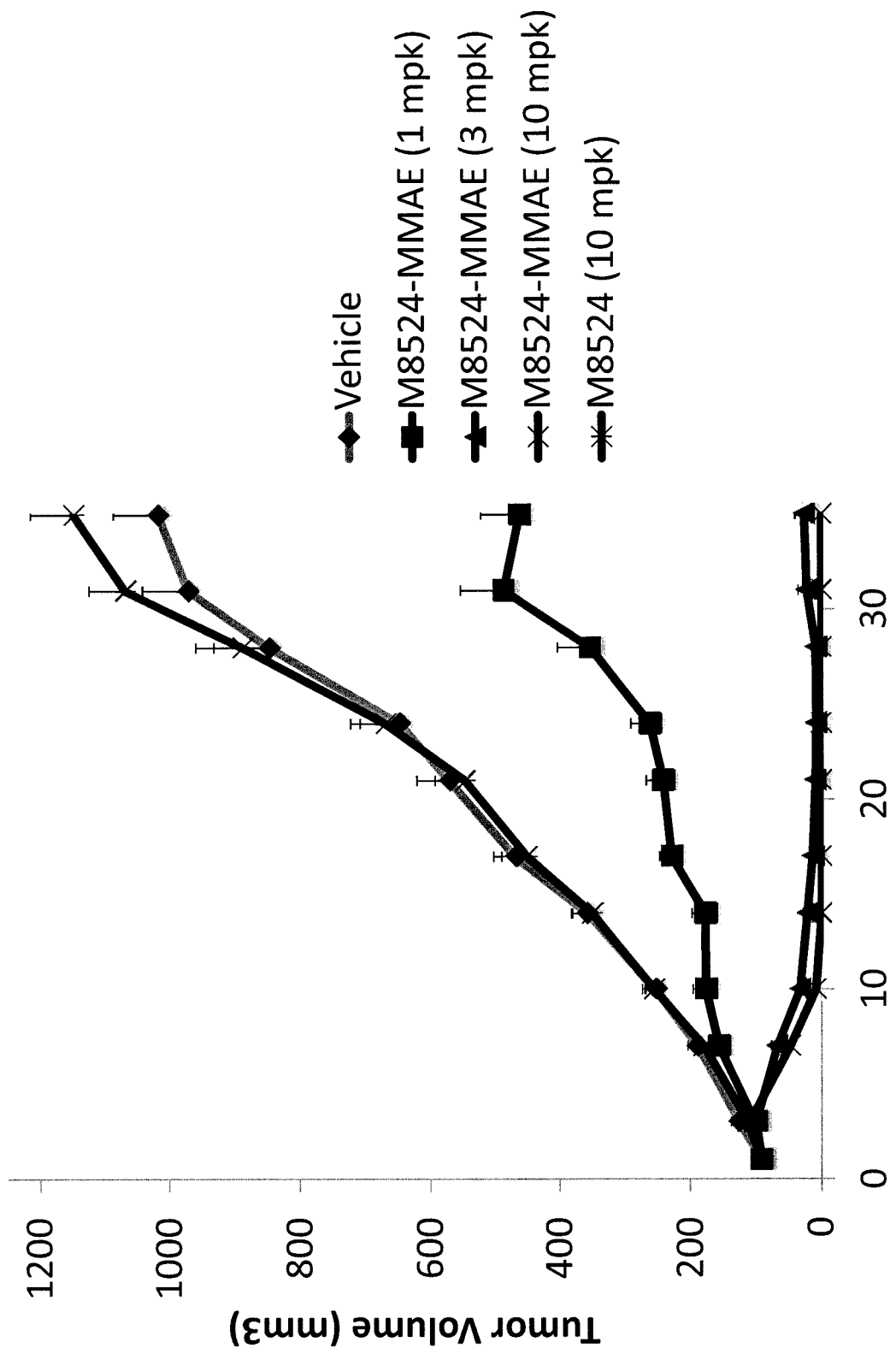
Figure 11:
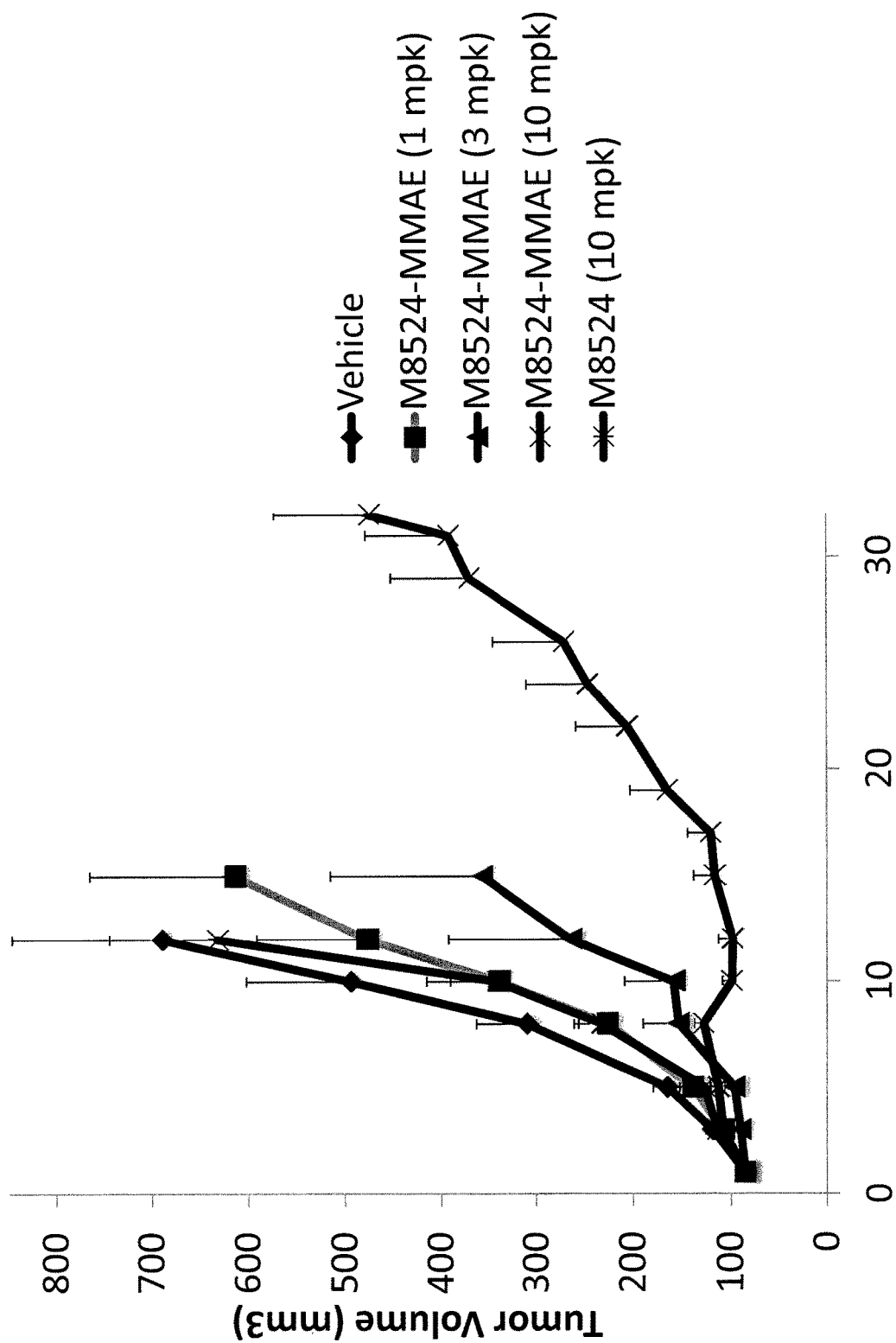

FIGS. 10 and 11 are graphs showing the tumor volume (mm$^3$) of HT-29 (FIG. 10) or KM12 (FIG. 11) in tumor bearing mice treated with control (vehicle) (diamonds), m8524 (M276) alone (10 mg/kg (mpk)) (*), or m8524 (m276)-MMAE ADCs at various dosages (1 mpk (squares), 3 mpk (triangles), or 10 mpk (x) at various time points (days) after administration.

Figure 12:
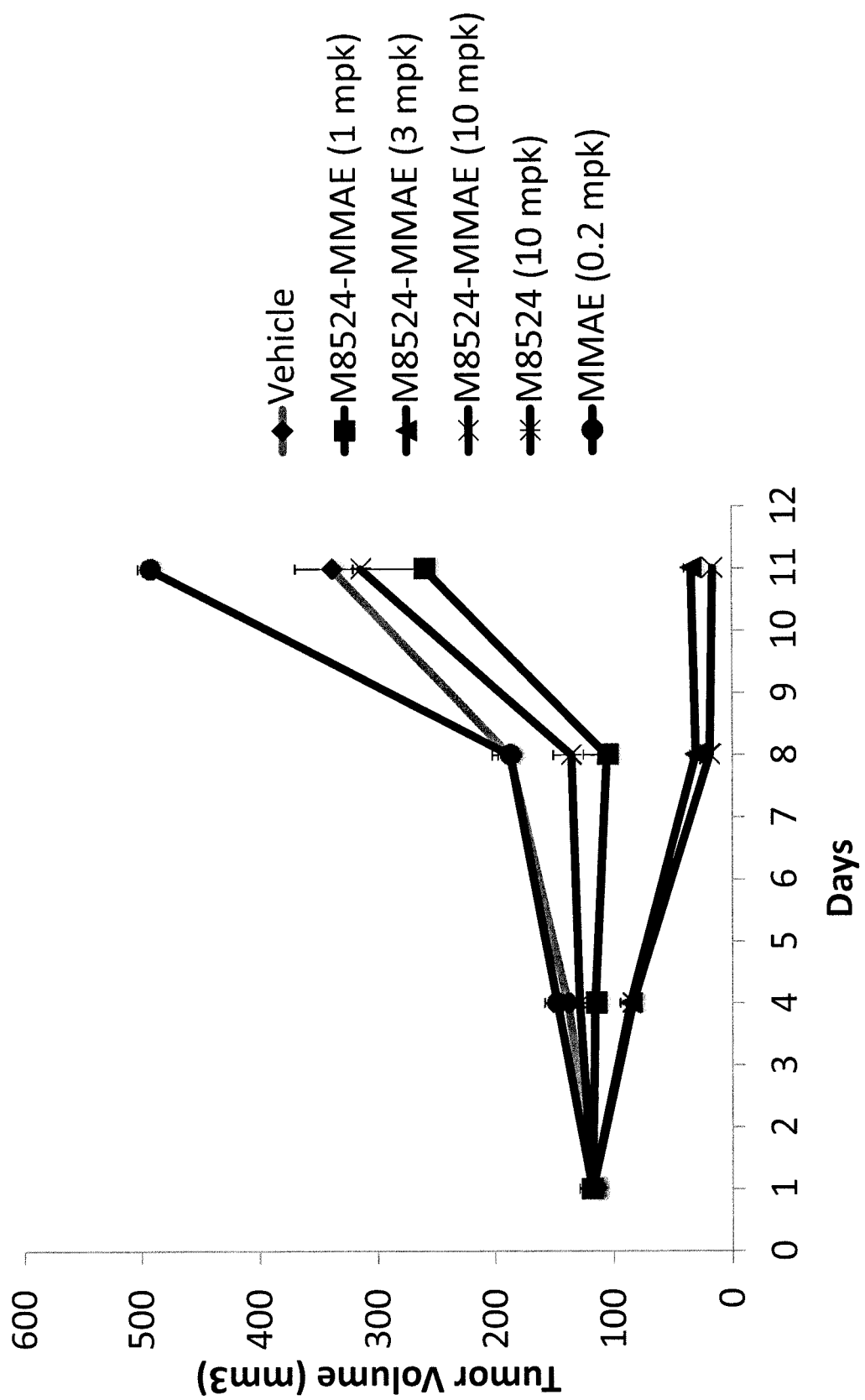

FIG. 12 is a graph showing the tumor volume (mm$^3$) in OVCAR3 tumor bearing mice treated with control (vehicle) (diamonds), m8524 (m276) alone (10 mg/kg (mpk)) (*), MMAE alone (0.2 mpk) (circles), or m8524 (m276)-MMAE ADCs at various dosages (1 mpk (squares), 3 mpk (triangles), or 10 mpk (x) at various time points (days) after administration. In FIG. 12, the compositions were administered on days 1, 4, 8, and 11.

Figure 13:
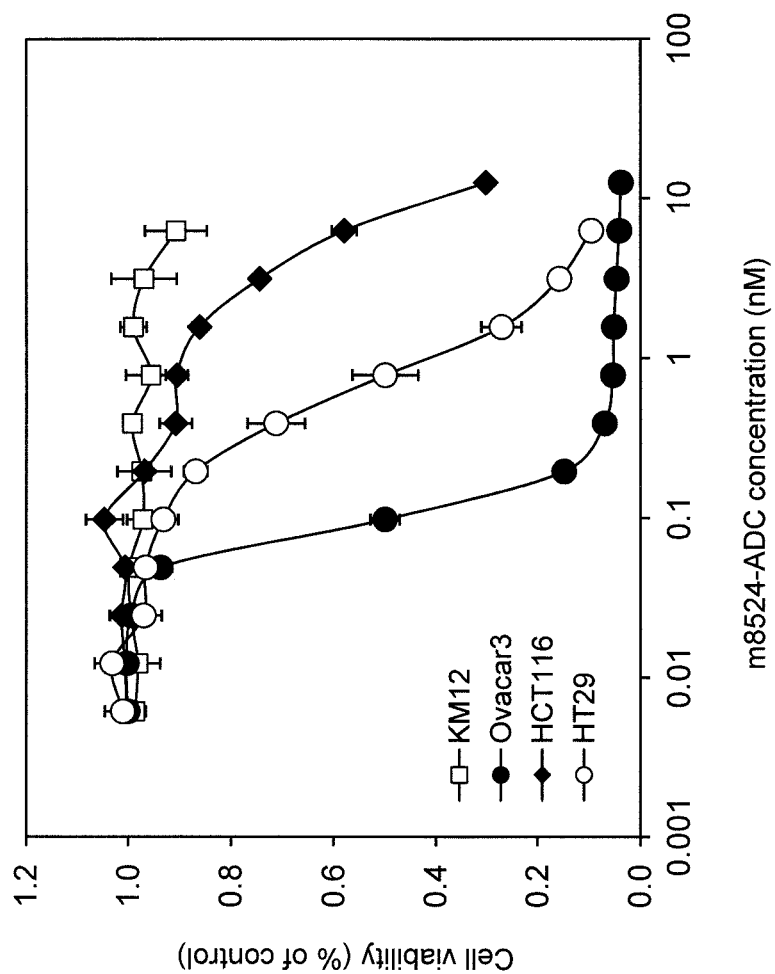

FIG. 13 is a graph showing the cell viability (% of control) of HCT116 (diamonds), HT29 (open circles), KM12 (squares) and OVCAR3 (closed circles) cancer cell lines treated with various concentrations (nM) of m8524-MMAE ADC.

Figure 14:
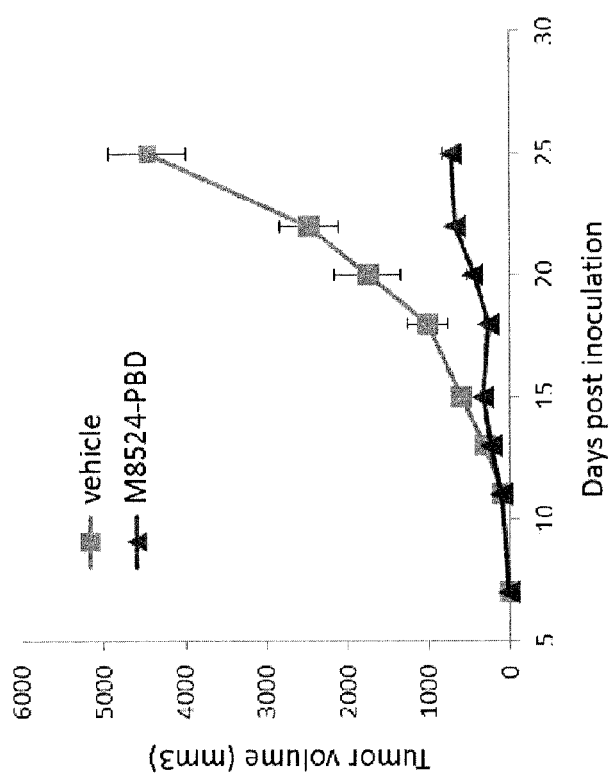

FIG. 14 is a graph showing the tumor volume (mm$^3$) in MC38 tumor-bearing mice treated with control (vehicle) (squares) or m8524 (m276)-PBD ADC (triangles) at various time points (days) following inoculation with MC38 cells.

Figure 15:
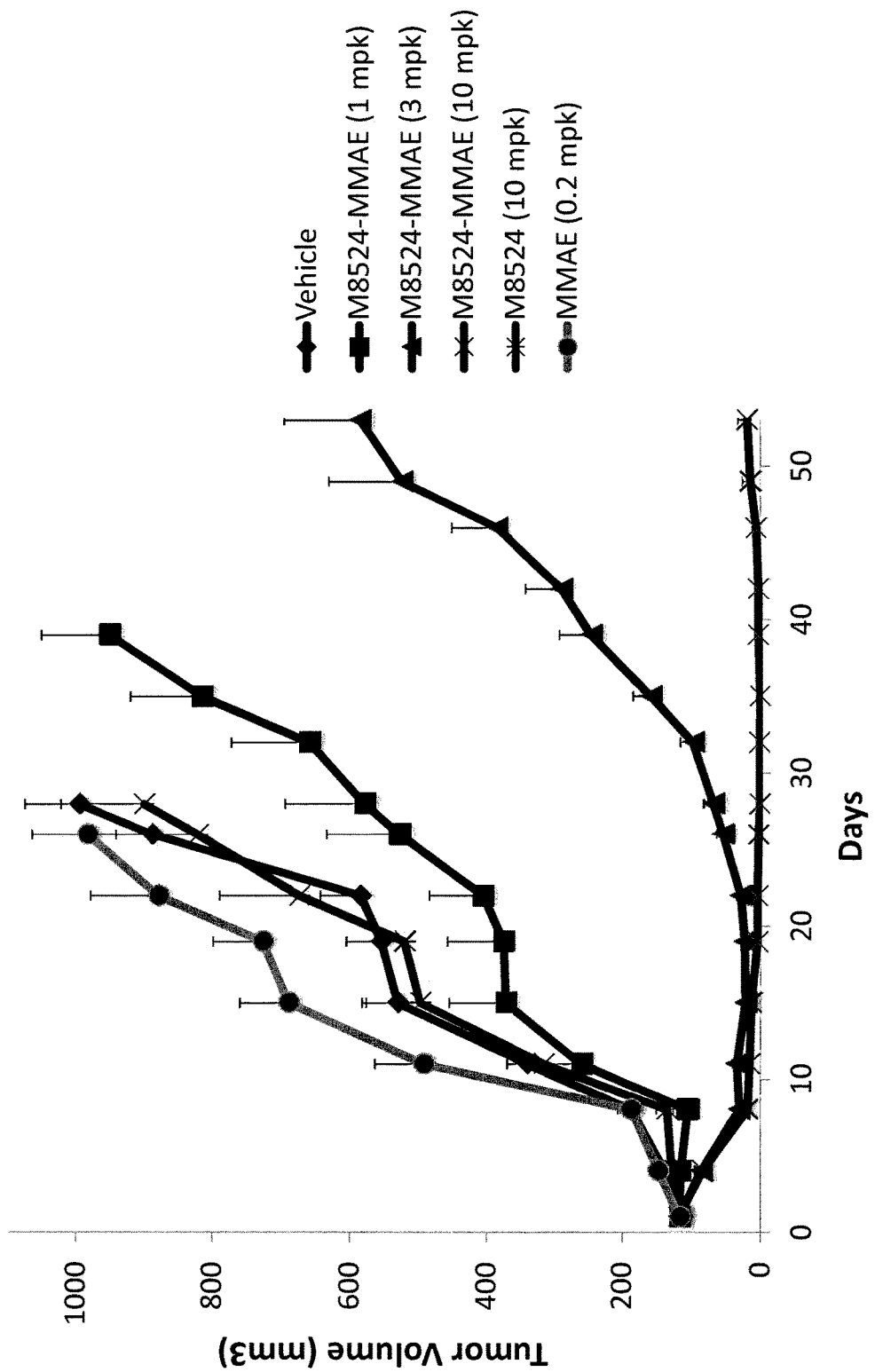

FIG. 15 is a graph showing the tumor volume (mm$^3$) in OVCAR3 tumor-bearing mice treated with control (vehicle) (diamonds), m8524 (M276) alone (10 mg/kg (mpk)) (*), MMAE alone (0.2 mpk) (circles), or m8524 (m276)-MMAE ADCs at various dosages (1 mpk (squares), 3 mpk (triangles), or 10 mpk (x) at various time points (days) after administration.

Figure 16:
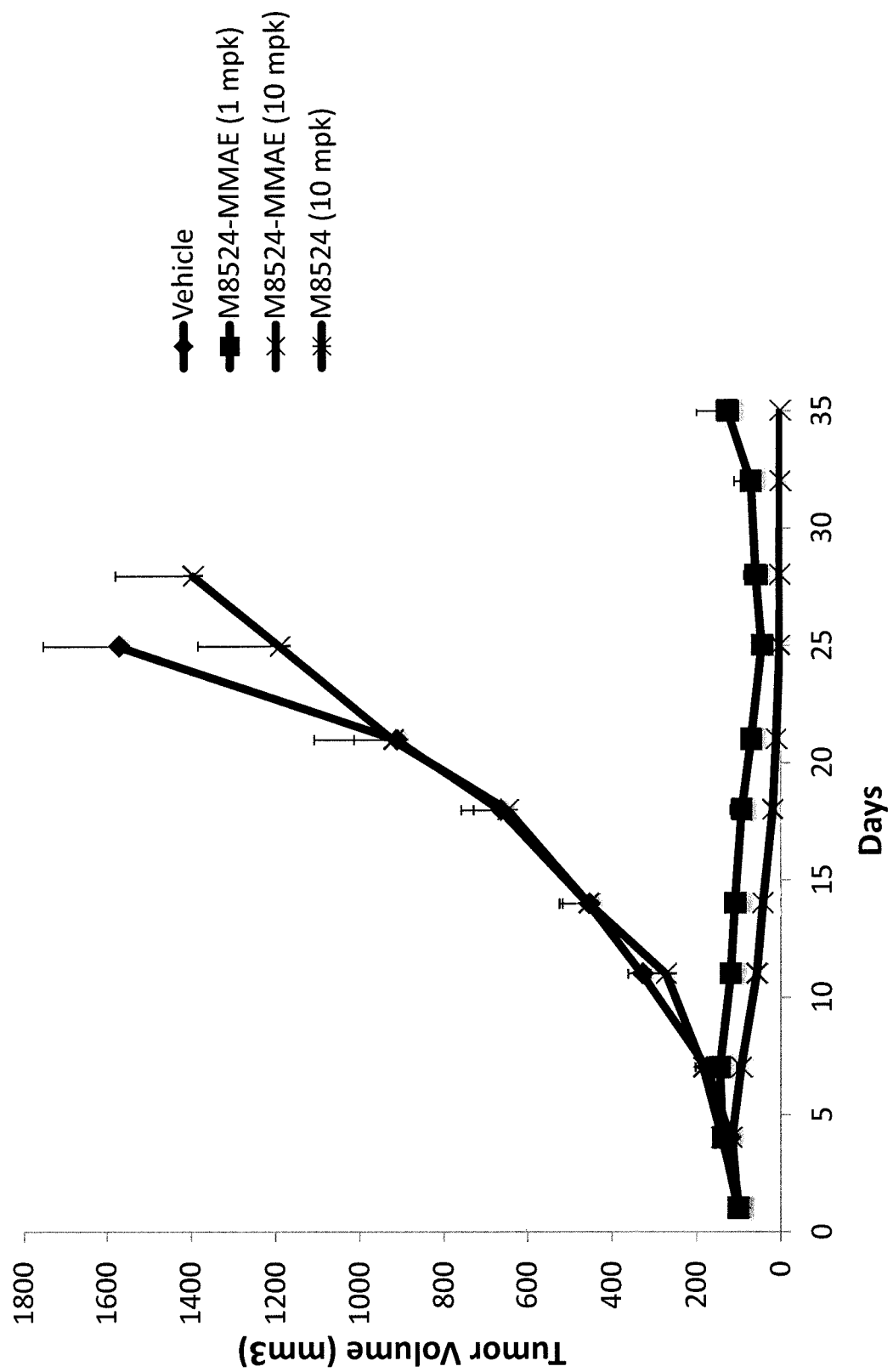

FIG. 16 is a graph showing the tumor volume (mm$^3$) in MDA-MB231 tumor-bearing mice treated with control (vehicle) (diamonds), m8524 (M276) alone (10 mg/kg (mpk)) (*), or m8524 (m276)-MMAE ADCs at a dosage of 1 mpk (squares) or 10 mpk (x) at various time points (days) after administration.

DETAILED DESCRIPTION OF THE INVENTION

An embodiment of the invention provides polypeptides and proteins comprising an antigen binding domain of an anti-CD276 antibody. The polypeptides and proteins advantageously specifically recognize and bind to CD276 (also known as B7-H3) with high affinity. The polypeptides and proteins advantageously specifically recognize and bind to soluble CD276 and also specifically recognize and bind to CD276 expressed on a cell surface. CD276 is expressed or overexpressed on a variety of human tumors, including pediatric solid tumors and adult carcinomas. Examples of cancers that express or overexpress CD276 include, but are not limited to, neuroblastoma, Ewing's sarcoma, rhabdomyosarcoma, and prostate, ovarian, colorectal, and lung cancers. CD276 is also expressed in tumor vasculature and is a tumor endothelial marker. Without being bound to a particular theory or mechanism, it is believed that by specifically recognizing and binding to CD276, the inventive polypeptides and proteins may, advantageously, target CD276-expressing cancer cells and/or tumor vasculature. In an embodiment of the invention, the inventive polypeptides and proteins may elicit an antigen-specific response against CD276. Accordingly, without being bound to a particular theory or mechanism, it is believed that by specifically recognizing and binding CD276, the inventive proteins and polypeptides may provide for one or more of the following: detecting CD276-expressing cancer cells and/or tumor vasculature, targeting and destroying CD276-expressing cancer cells and/or tumor vasculature, reducing or eliminating cancer cells and/or tumor vasculature, facilitating infiltration of immune cells and/or effector molecules to tumor site(s) and/or tumor vasculature, and enhancing/extending anti-cancer and/or anti-tumor vasculature responses.

The term "polypeptide" as used herein includes oligopeptides and refers to a single chain of amino acids connected by one or more peptide bonds. The polypeptide may comprise one or more variable regions (e.g., two variable regions) of an antigen binding domain of an anti-CD276 antibody, each variable region comprising a complementarity determining region (CDR) 1, a CDR2, and a CDR3. Preferably, a first variable region comprises a CDR1 comprising the amino acid sequence of SEQ ID NO: 1, 11, or 20 (CDR1 of first variable region), a CDR2 comprising the amino acid sequence of SEQ ID NO: 2, 12, or 21 (CDR2 of first variable region), and a CDR3 comprising the amino acid sequence of SEQ ID NO: 3, 13, or 22 (CDR3 of first variable region), and the second variable region comprises a CDR1 comprising the amino acid sequence of SEQ ID NO: 4, 14, or 23 (CDR1 of second variable region), a CDR2 comprising the amino acid sequence of SEQ ID NO: 5, 15, or 24 (CDR2 of second variable region), and a CDR3 comprising the amino acid sequence of SEQ ID NO: 6, 16, or 25 (CDR3 of second variable region). In this regard, the inventive polypeptide can comprise SEQ ID NOs: 1-3, 4-6, 11-13, 14-16, 20-22, 23-25, 1-6, 11-16, or 20-25. Accordingly, an embodiment of the invention provides a polypeptide comprising (i) SEQ ID NOs: 1-6, (ii) SEQ ID NOs: 11-16, or (iii) SEQ ID NOs: 20-25. Preferably, the polypeptide comprises the amino acid sequences of SEQ ID NOs: 20-25.

In an embodiment, the polypeptides each comprise one or more variable regions (e.g., first and second variable regions) of an antigen binding domain of an anti-CD276 antibody, each comprising the CDRs as described above. The first variable region may comprise SEQ ID NO: 7, 17, or 26. The second variable region may comprise SEQ ID NO: 8, 18, or 27. Accordingly, in an embodiment of the invention, the polypeptide comprises SEQ ID NO: 7, SEQ ID NO: 8, SEQ ID NO: 17, SEQ ID NO: 18, SEQ ID NO: 26, SEQ ID NO: 27, SEQ ID NOs: 7 and 8, SEQ ID NOs: 17 and 18, or SEQ ID NOs: 26 and 27. Preferably, the polypeptide comprises SEQ ID NOs: 26 and 27. In an embodiment of the invention, the first variable region is the heavy chain of an anti-CD276 antibody and the second variable region is the light chain of an anti-CD276 antibody.

In an embodiment of the invention, the variable regions of the polypeptide may be joined by a linker. The linker may comprise any suitable amino acid sequence. In an embodiment of the invention, the linker may comprise SEQ ID NO: 9 or 10.

In an embodiment, the polypeptide comprises a leader sequence. The leader sequence may be positioned at the amino terminus of the light chain variable region. The leader sequence may comprise any suitable leader sequence. In an embodiment, the leader sequence is a human granulocyte-macrophage colony-stimulating factor (GM-CSF) receptor sequence. The leader sequence may comprise, for example, SEQ ID NO: 39, 40, or 41. In an embodiment of the invention, while the leader sequence may facilitate expression of the polypeptide on the surface of the cell, the presence of the leader sequence in an expressed polypeptide is not necessary in order for the polypeptide to function. In an embodiment of the invention, upon expression of the polypeptide on the cell surface, the leader sequence may be cleaved off of the polypeptide. Accordingly, in an embodiment of the invention, the polypeptide lacks a leader sequence.

The invention further provides a protein comprising at least one of the polypeptides described herein. By "protein" is meant a molecule comprising one or more polypeptide chains.

The protein of the invention can comprise a first polypeptide chain comprising the amino acid sequences of (i) SEQ ID NOs: 1-3, (ii) SEQ ID NOs: 11-13, or (iii) SEQ ID NOs: 20-22 and a second polypeptide chain comprising (i) SEQ ID NOs: 4-6, (ii) SEQ ID NOs: 14-16, or (iii) SEQ ID NOs: 23-25. The protein of the invention can, for example, comprise a first polypeptide chain comprising the amino acid sequence of SEQ ID NO: 7, 17, or 26 and a second polypeptide chain comprising the amino acid sequence of SEQ ID NO: 8, 18, or 27. In this regard, the protein may comprise a first polypeptide chain comprising SEQ ID NO: 7, 17, or 26 and a second polypeptide chain comprising SEQ ID NO: 8, 18, or 27.

The protein may further comprise a leader sequence and/or a linker as described herein with respect to other aspects of the invention. In an embodiment, the protein lacks a leader sequence.

The protein of the invention can be, for example, a fusion protein. If, for example, the protein comprises a single polypeptide chain comprising (i) SEQ ID NO: 7, 17, or 26 and (ii) SEQ ID NO: 8, 18, or 27, or if the first and/or second polypeptide chain(s) of the protein further comprise(s) other amino acid sequences, e.g., an amino acid sequence encoding an immunoglobulin or a portion thereof, then the inventive protein can be a fusion protein. In this regard, the invention also provides a fusion protein comprising at least one of the inventive polypeptides described herein along with at least one other polypeptide. The other polypeptide can exist as a separate polypeptide of the fusion protein, or can exist as a polypeptide, which is expressed in frame (in tandem) with one of the inventive polypeptides described herein. The other polypeptide can encode any peptidic or proteinaceous molecule, or a portion thereof, including, but not limited to an immunoglobulin, CD3, CD4, CD8, an MHC molecule, a CD1 molecule, e.g., CD1a, CD1b, CD1c, CD1d, etc.

The fusion protein can comprise one or more copies of the inventive polypeptide and/or one or more copies of the other polypeptide. For instance, the fusion protein can comprise 1, 2, 3, 4, 5, or more, copies of the inventive polypeptide and/or of the other polypeptide. Suitable methods of making fusion proteins are known in the art, and include, for example, recombinant methods. See, for instance, Choi et al., *Mol. Biotechnol.* 31: 193-202 (2005).

It is contemplated that the polypeptides and proteins of the invention may be useful as anti-CD276 binding moieties. In this regard, an embodiment of the invention provides an anti-CD276 binding moiety comprising any of the polypeptides or proteins described herein. In an embodiment of the invention, the anti-CD276 binding moiety comprises an antigen binding portion of any of the polypeptides or proteins described herein. The antigen binding portion can be any portion that has at least one antigen binding site. In an embodiment, the anti-CD276 binding moiety is an antibody, a Fab fragment (Fab), F(ab')$_2$ fragment, diabody, triabody, tetrabody, single-chain variable region fragment (scFv), or disulfide-stabilized variable region fragment (dsFv).

In an embodiment, the anti-CD276 binding moiety is an antibody. The antibody may be, for example, a recombinant antibody comprising at least one of the inventive polypeptides described herein. As used herein, "recombinant antibody" refers to a recombinant (e.g., genetically engineered) protein comprising at least one of the polypeptides or proteins of the invention and one or more polypeptide chains of an antibody, or a portion thereof. The polypeptide of an antibody, or portion thereof, can be, for example, a constant region of a heavy or light chain, or an Fc fragment of an antibody, etc. The polypeptide chain of an antibody, or portion thereof, can exist as a separate polypeptide of the recombinant antibody. Alternatively, the polypeptide chain of an antibody, or portion thereof, can exist as a polypeptide, which is expressed in frame (in tandem) with the polypeptide or protein of the invention. The polypeptide of an antibody, or portion thereof, can be a polypeptide of any antibody or any antibody fragment.

The antibody of the invention can be any type of immunoglobulin that is known in the art. For instance, the anti-CD276 binding moiety can be an antibody of any isotype, e.g., IgA, IgD, IgE, IgG (e.g., IgG1, IgG2, IgG3, or IgG4), IgM, etc. The antibody can be monoclonal or polyclonal. The antibody can be a naturally-occurring antibody, e.g., an antibody isolated and/or purified from a mammal, e.g., mouse, rabbit, goat, horse, chicken, hamster, human, etc. Alternatively, the antibody can be a genetically-engineered antibody, e.g., a humanized antibody or a chimeric antibody. The antibody can be in monomeric or polymeric form. Also, the antibody can have any level of affinity or avidity for CD276.

Methods of testing antibodies for the ability to bind to CD276 are known in the art and include any antibody-antigen binding assay, such as, for example, radioimmunoassay (RIA), enzyme-linked immunosorbent assay (ELISA), Western blot, immunoprecipitation, and competitive inhibition assays (see, e.g., Murphy et al., infra, and U.S. Patent Application Publication No. 2002/0197266 A1).

Suitable methods of making antibodies are known in the art. For instance, standard hybridoma methods are described in, e.g., Köhler and Milstein, *Eur. J. Immunol.*, 5, 511-519 (1976), Greenfield (ed.), *Antibodies: A Laboratory Manual*, 2$^{nd}$ Ed., CSH Press (2013), and Murphy et al. (eds.), *Janeway's Immunobiology*, 8$^{th}$ Ed., Taylor & Francis, Inc., New York, N.Y. (2011)). Alternatively, other methods, such as Epstein-Barr virus (EBV)-hybridoma methods (Haskard and Archer, *J. Immunol. Methods,* 74(2), 361-67 (1984), and Roder et al., *Methods Enzymol.,* 121, 140-67 (1986)), and bacteriophage vector expression systems (see, e.g., Huse et al., *Science,* 246, 1275-81 (1989)) are known in the art. Further, methods of producing antibodies in non-human animals are described in, e.g., U.S. Pat. Nos. 5,545,806, 5,569,825, and 5,714,352, and U.S. Patent Application Publication No. 2002/0197266 A1.

Phage display furthermore can be used to generate an antibody. In this regard, phage libraries encoding antigen-binding variable (V) domains of antibodies can be generated using standard molecular biology and recombinant DNA techniques. See, for instance, Green et al. (eds.), *Molecular Cloning, A Laboratory Manual*, 4$^{th}$ Edition, Cold Spring Harbor Laboratory Press, New York (2012) and Ausubel et al., *Current Protocols in Molecular Biology*, Greene Publishing Associates and John Wiley & Sons, NY (2007). Phage encoding a variable region with the desired specificity are selected for specific binding to the desired antigen, and a complete or partial antibody is reconstituted comprising the selected variable domain. Nucleic acid sequences encoding the reconstituted antibody are introduced into a suitable cell line, such as a myeloma cell used for hybridoma production, such that antibodies having the characteristics of monoclonal antibodies are secreted by the cell (see, e.g., Murphy et al., supra, Huse et al., supra, and U.S. Pat. No. 6,265,150).

Antibodies can be produced by transgenic mice that are transgenic for specific heavy and light chain immunoglobulin genes. Such methods are known in the art and described in, for example U.S. Pat. Nos. 5,545,806 and 5,569,825, and Murphy et al., supra.

Methods for generating humanized antibodies are well known in the art and are described in detail in, for example, Murphy et al., supra, U.S. Pat. Nos. 5,225,539, 5,585,089 and 5,693,761, European Patent No. 0239400 B1, and United Kingdom Patent No. 2188638. Humanized antibodies can also be generated using the antibody resurfacing technology described in U.S. Pat. No. 5,639,641 and Pedersen et al., *J. Mol. Biol.,* 235, 959-973 (1994).

In a preferred embodiment, the anti-CD276 binding moiety is a single-chain variable region fragment (scFv). A single-chain variable region fragment (scFv) antibody fragment, which is a truncated Fab fragment including the variable (V) domain of an antibody heavy chain linked to a V domain of a light antibody chain via a synthetic peptide, can be generated using routine recombinant DNA technology techniques (see, e.g., Murphy et al., supra). Similarly, disulfide-stabilized variable region fragments (dsFv) can be prepared by recombinant DNA technology (see, e.g., Reiter et al., *Protein Engineering,* 7: 697-704 (1994)). The anti-CD276 binding moieties of the invention, however, are not limited to these exemplary types of antibody fragments.

Also, the anti-CD276 binding moiety can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

Another embodiment of the invention provides chimeric antigen receptors (CARs) comprising: (a) an antigen binding domain comprising any of the polypeptides or proteins described herein, (b) a transmembrane domain, and (c) an intracellular T cell signaling domain.

A chimeric antigen receptor (CAR) is an artificially constructed hybrid protein or polypeptide containing the antigen binding domains of an antibody (e.g., single chain variable fragment (scFv)) linked to T-cell signaling domains. Characteristics of CARs include their ability to redirect T-cell specificity and reactivity toward a selected target in a non-MHC-restricted manner, exploiting the antigen-binding properties of monoclonal antibodies. The non-MHC-restricted antigen recognition gives cells expressing CARs the ability to recognize antigen independent of antigen processing, thus bypassing a major mechanism of tumor escape. Moreover, when expressed in T-cells, CARs advantageously do not dimerize with endogenous T cell receptor (TCR) alpha and beta chains.

The phrases "have antigen specificity" and "elicit antigen-specific response" as used herein means that the CAR can specifically bind to and immunologically recognize an antigen, such that binding of the CAR to the antigen elicits an immune response.

The CARs of the invention have antigen specificity for CD276 (also known as B7-H3). Without being bound to a particular theory or mechanism, it is believed that by eliciting an antigen-specific response against CD276, the inventive CARs provide for one or more of the following: targeting and destroying CD276-expressing cancer cells and/or tumor vasculature, reducing or eliminating cancer cells and/or tumor vasculature, facilitating infiltration of immune cells to tumor site(s) and/or tumor vasculature, and enhancing/extending anti-cancer and anti-tumor vasculature responses.

An embodiment of the invention provides a CAR comprising an antigen binding domain of an anti-CD276 antibody. The antigen binding domain of the anti-CD276 antibody specifically binds to CD276. The antigen binding domain of the CARs may comprise any of the polypeptides or proteins described herein. In an embodiment of the invention, the CAR comprises an anti-CD276 single chain variable fragment (scFv). In this regard, a preferred embodiment of the invention provides a CAR comprising an antigen-binding domain comprising a single chain variable fragment (scFv) that comprises any of the polypeptides or proteins described herein.

In a preferred embodiment of the invention, the CAR comprises a heavy chain and a light chain each of which comprises a variable region comprising a complementarity determining region (CDR) 1, a CDR2, and a CDR3. Preferably, the heavy chain comprises a CDR1 comprising the amino acid sequence of SEQ ID NO: 1, 11, or 20 (CDR1 of heavy chain), a CDR2 comprising the amino acid sequence of SEQ ID NO: 2, 12, or 21 (CDR2 of heavy chain), and a CDR3 comprising the amino acid sequence of SEQ ID NO: 3, 13, or 22 (CDR3 of heavy chain), and the light chain comprises a CDR1 comprising the amino acid sequence of SEQ ID NO: 4, 14, or 23 (CDR1 of light chain), a CDR2 comprising the amino acid sequence of SEQ ID NO: 5, 15, or 24 (CDR2 of light chain), and a CDR3 comprising the amino acid sequence of SEQ ID NO: 6, 16, or 25 (CDR3 of light chain). In this regard, the inventive CAR can comprise SEQ ID NOs: 1-3, 4-6, 11-13, 14-16, 20-22, 23-25, 1-6, 11-16, or 20-25. Preferably the CAR comprises the amino acid sequences of SEQ ID NOs: 20-25.

The antigen binding domains of the CARs each comprise a light chain and a heavy chain. The light chain may comprise SEQ ID NO: 8, 18, or 27. The heavy chain may comprise SEQ ID NO: 7, 17, or 26. Accordingly, in an embodiment of the invention, the antigen binding domain comprises SEQ ID NO: 7, SEQ ID NO: 8, SEQ ID NO: 17, SEQ ID NO: 18, SEQ ID NO: 26, SEQ ID NO: 27, SEQ ID NOs: 7 and 8, SEQ ID NOs: 17 and 18, or SEQ ID NOs: 26 and 27. Preferably, the CAR comprises SEQ ID NOs: 26 and 27.

In an embodiment, the antigen binding domain of the CAR comprises a leader sequence. The leader sequence may be as described herein with respect to other aspects of the invention. In an embodiment of the invention, the CAR lacks a leader sequence.

In an embodiment, the CAR comprises an immunoglobulin constant domain. Preferably, the immunoglobulin domain is a human immunoglobulin sequence. In an embodiment, the immunoglobulin constant domain comprises an immunoglobulin CH2 and CH3 immunoglobulin G (IgG1) domain sequence (CH2CH3). In this regard, the CAR may comprise an immunoglobulin constant domain comprising SEQ ID NO: 45. Without being bound to a particular theory, it is believed that the CH2CH3 domain extends the binding motif of the scFv away from the membrane of the CAR-expressing cells and may more accurately mimic the size and domain structure of a native TCR. In some embodiments, the CAR may lack an immunoglobulin constant domain.

In an embodiment of the invention, the CAR comprises a transmembrane domain. In an embodiment of the invention, the transmembrane domain comprises i) CD8 and/or ii) CD28. In a preferred embodiment, the CD8 and CD28 are human. The CD8 or CD28 may comprise less than the whole CD8 or CD28, respectively. In this regard, the CAR comprises a transmembrane domain comprising any one or more of a CD8 amino acid sequence comprising SEQ ID NO: 29, a CD28 amino acid sequence comprising SEQ ID NO: 30, and a CD8 amino acid sequence comprising SEQ ID NO: 31.

In an embodiment of the invention, the CAR comprises an intracellular T cell signaling domain comprising one or more of i) CD28, ii) CD137, and iii) CD3 zeta ($\zeta$). In a preferred embodiment, the one or more of CD28, CD 137, and CD3 zeta are human. CD28 is a T cell marker important in T cell co-stimulation. CD137, also known as 4-1BB, transmits a potent costimulatory signal to T cells, promoting differentiation and enhancing long-term survival of T lymphocytes. CD3t associates with TCRs to produce a signal and contains immunoreceptor tyrosine-based activation motifs (ITAMs). One or more of CD28, CD137, and CD3 zeta may comprise less than the whole CD28, CD137, or CD3 zeta, respectively. In an embodiment of the invention, intracellular T cell signaling domain comprises a CD28 amino acid sequence comprising SEQ ID NO: 32 and/or SEQ ID NO: 35. In another embodiment of the invention, the intracellular T cell signaling domain comprises a CD137 amino acid sequence comprising SEQ ID NO: 33 and/or SEQ ID NO: 37. In another embodiment of the invention, the intracellular T cell signaling domain comprises a CD3 zeta amino acid sequence comprising any one or more of SEQ ID NOs: 34, 36, and 38.

In an embodiment of the invention, the CAR comprises a transmembrane domain comprising CD28 and an intracellular T cell signaling domain comprising CD28 and CD3 zeta. In this regard, the CAR may comprise each of SEQ ID NOs: 30, 35, and 36. In an embodiment, a transmembrane domain comprising CD28 and an intracellular T cell signaling domain comprising CD28 and CD3 zeta comprises SEQ ID NO: 47. Preferably, the CAR comprises (a) each of SEQ ID NOs: 1-6, 45, 30, 35, and 36; (b) each of SEQ ID NOs: 7, 8, 45, 30, 35, and 36; (c) each of SEQ ID NOs: 11-16, 45, 30, 35, and 36; (d) each of SEQ ID NOs: 17, 18, 45, 30, 35, and 36; (e) each of SEQ ID NOs: 20-25, 45, 30, 35, and 36; or (f) each of SEQ ID NOs: 26, 27, 45, 30, 35, and 36.

In an embodiment of the invention, the CAR comprises a transmembrane domain comprising CD8 and an intracellular T cell signaling domain comprising CD28, CD137, and CD3 zeta. In this regard, the CAR may comprise each of SEQ ID NOs: 29 and 32-34. In an embodiment, a transmembrane domain comprising CD8 and an intracellular T cell signaling domain comprising CD28, CD137, and CD3 zeta comprises SEQ ID NO: 49. Preferably, the CAR comprises (a) each of SEQ ID NOs: 1-6, 45, 29, and 32-34; (b) each of SEQ ID NOs: 7, 8, 45, 29, and 32-34; (c) each of SEQ ID NOs: 11-16, 45, 29, and 32-34; (d) each of SEQ ID NOs: 17, 18, 45, 29, and 32-34; (e) each of SEQ ID NOs: 20-25, 45, 29, and 32-34; or (f) each of SEQ ID NOs: 26, 27, 45, 29, and 32-34.

In an embodiment of the invention, the CAR comprises a transmembrane domain comprising CD8 and an intracellular T cell signaling domain comprising CD137 and CD3 zeta. In this regard, the CAR may comprise each of SEQ ID NOs: 31, 37, and 38. In an embodiment, a transmembrane domain comprising CD8 and an intracellular T cell signaling domain comprising CD137 and CD3 zeta comprises SEQ ID NO: 48. Preferably, the CAR comprises each of (a) each of SEQ ID NOs: 1-6, 45, 31, 37, and 38; (b) each of SEQ ID NOs: 7, 8, 45, 31, 37, and 38; (c) each of SEQ ID NOs: 11-16, 45, 31, 37, and 38; (d) each of SEQ ID NOs: 17, 18, 45, 31, 37, and 38; (e) each of SEQ ID NOs: 20-25, 45, 31, 37, and 38; or (f) each of SEQ ID NOs: 26, 27, 45, 31, 37, and 38.

Included in the scope of the invention are functional portions of the inventive polypeptides, proteins, and CARs described herein. The term "functional portion" when used in reference to a polypeptide, protein, or CAR refers to any part or fragment of the polypeptide, protein, or CAR of the invention, which part or fragment retains the biological activity of the polypeptide, protein, or CAR of which it is a part (the parent polypeptide, protein, or CAR). Functional portions encompass, for example, those parts of a polypeptide, protein, or CAR that retain the ability to recognize target cells, or detect, treat, or prevent a disease, to a similar extent, the same extent, or to a higher extent, as the parent polypeptide, protein, or CAR. In reference to the parent polypeptide, protein, or CAR, the functional portion can comprise, for instance, about 10%, 25%, 30%, 50%, 68%, 80%, 90%, 95%, or more, of the parent polypeptide, protein, or CAR.

The functional portion can comprise additional amino acids at the amino or carboxy terminus of the portion, or at both termini, which additional amino acids are not found in the amino acid sequence of the parent polypeptide, protein, or CAR. Desirably, the additional amino acids do not interfere with the biological function of the functional portion, e.g., recognize target cells, detect cancer and/or tumor vasculature, treat or prevent cancer, reduce or eliminate tumor vasculature, etc. More desirably, the additional amino acids enhance the biological activity, as compared to the biological activity of the parent polypeptide, protein, or CAR.

Included in the scope of the invention are functional variants of the inventive polypeptides, proteins, or CARs described herein. The term "functional variant" as used herein refers to a polypeptide, protein, or CAR having substantial or significant sequence identity or similarity to a parent polypeptide, protein, or CAR, which functional variant retains the biological activity of the polypeptide, protein, or CAR of which it is a variant. Functional variants encompass, for example, those variants of the polypeptide, protein, or CAR described herein (the parent polypeptide, protein, or CAR) that retain the ability to recognize target cells to a similar extent, the same extent, or to a higher extent, as the parent polypeptide, protein, or CAR. In reference to the parent polypeptide, protein, or CAR, the functional variant can, for instance, be at least about 30%, about 50%, about 75%, about 80%, about 85%, about 90%, about 91%, about 92%, about 93%, about 94%, about 95%, about 96%, about 97%, about 98%, about 99% or more identical in amino acid sequence to the parent polypeptide, protein, or CAR.

A functional variant can, for example, comprise the amino acid sequence of the parent polypeptide, protein, or CAR with at least one conservative amino acid substitution. Alternatively or additionally, the functional variants can comprise the amino acid sequence of the parent polypeptide, protein, or CAR with at least one non-conservative amino acid substitution. In this case, it is preferable for the non-conservative amino acid substitution to not interfere with or inhibit the biological activity of the functional variant. The non-conservative amino acid substitution may enhance the biological activity of the functional variant, such that the biological activity of the functional variant is increased as compared to the parent polypeptide, protein, or CAR.

Amino acid substitutions of the inventive polypeptides, proteins, or CARs are preferably conservative amino acid substitutions. Conservative amino acid substitutions are known in the art, and include amino acid substitutions in which one amino acid having certain physical and/or chemical properties is exchanged for another amino acid that has the same or similar chemical or physical properties. For instance, the conservative amino acid substitution can be an acidic/negatively charged polar amino acid substituted for another acidic/negatively charged polar amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Cys, Val, etc.), a basic/positively charged polar amino acid substituted for another basic/positively charged polar amino acid (e.g. Lys, His, Arg, etc.), an uncharged amino acid with a polar side chain substituted for another uncharged amino acid with a polar side chain (e.g., Asn, Gln, Ser, Thr, Tyr, etc.), an amino acid with a beta-branched side-chain substituted for another amino acid with a beta-branched side-chain (e.g., Ile, Thr, and Val), an amino acid with an aromatic side-chain substituted for another amino acid with an aromatic side chain (e.g., His, Phe, Trp, and Tyr), etc.

The polypeptide, protein, or CAR can consist essentially of the specified amino acid sequence or sequences described herein, such that other components, e.g., other amino acids, do not materially change the biological activity of the polypeptide, protein, CAR, functional portion, or functional variant.

The polypeptides, proteins, or CARs of embodiments of the invention (including functional portions and functional variants) can be of any length, i.e., can comprise any number of amino acids, provided that the polypeptides, proteins, or CARs (or functional portions or functional variants thereof) retain their biological activity, e.g., the ability to specifically bind to antigen, detect diseased cells in a mammal, or treat or prevent disease in a mammal, etc. For example, the polypeptide, protein, or CAR can be about 50 to about 5000 amino acids long, such as 50, 70, 75, 100, 125, 150, 175, 200, 300, 400, 500, 600, 700, 800, 900, 1000 or more amino acids in length.

The polypeptides, proteins, or CARs of embodiments of the invention (including functional portions and functional variants of the invention) can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

The polypeptides, proteins, or CARs of embodiments of the invention (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized.

The polypeptides, proteins, or CARs of embodiments of the invention (including functional portions and functional variants thereof) can be obtained by methods known in the art. The polypeptides, proteins, or CARs may be made by any suitable method of making polypeptides or proteins. Suitable methods of de novo synthesizing polypeptides and proteins are described in references, such as Chan et al., *Fmoc Solid Phase Peptide Synthesis*, Oxford University Press, Oxford, United Kingdom, 2000; *Peptide and Protein Drug Analysis*, ed. Reid, R., Marcel Dekker, Inc., 2000; *Epitope Mapping*, ed. Westwood et al., Oxford University Press, Oxford, United Kingdom, 2001; and U.S. Pat. No. 5,449,752. Also, polypeptides and proteins can be recombinantly produced using the nucleic acids described herein using standard recombinant methods. See, e.g., Green et al., supra, and Ausubel et al., supra. Further, some of the polypeptides, proteins, or CARs of the invention (including functional portions and functional variants thereof) can be isolated and/or purified from a source, such as a plant, a bacterium, an insect, a mammal, e.g., a rat, a human, etc. Methods of isolation and purification are well-known in the art. Alternatively, the polypeptides, proteins, or CARs described herein (including functional portions and functional variants thereof) can be commercially synthesized by companies, such as Synpep (Dublin, Calif.), Peptide Technologies Corp. (Gaithersburg, Md.), and Multiple Peptide Systems (San Diego, Calif.). In this respect, the inventive polypeptides, proteins, or CARs can be synthetic, recombinant, isolated, and/or purified.

Included in the scope of the invention are conjugates, e.g., bioconjugates, comprising any of the inventive polypeptides, proteins, CARs, anti-CD276 binding moieties, or functional portions or functional variants thereof. Conjugates, as well as methods of synthesizing conjugates in general, are known in the art (See, for instance, Hudecz, F.,

*Methods Mol. Biol.* 298: 209-223 (2005) and Kirin et al., *Inorg Chem.* 44(15): 5405-5415 (2005)). In this regard, an embodiment of the invention provides a conjugate comprising (a) any of the polypeptides, proteins, CARs, or anti-CD276 binding moieties described herein conjugated to (b) an effector molecule. The effector molecule may be any therapeutic molecule or a molecule that facilitates the detection of the conjugate. The effector molecule is not limited and may be any suitable effector molecule. For example, the effector molecule may be any one or more of a drug, toxin, label (e.g., any of the detectable labels described herein), small molecule, or another antibody. For example, the toxin may be *Pseudomonas* exotoxin A ("PE") or variants thereof such as, e.g., any of PE4E, PE40, PE38, PE25, PE38QQR, PE38KDEL, PE-LR, and PE35, as described in, e.g., U.S. Pat. Nos. 4,892,827; 5,512,658; 5,602,095; 5,608,039; 5,821,238; 5,854,044; U.S. Patent Application Publication No. US 2010/0215656; and WO 2012/041234, each of which is incorporated herein by reference. Examples of drugs that may be suitable in the inventive conjugates include, but are not limited to, pyrrolobenzodiazepine (PBD) dimer, tubulin-binders such as, for example, dolastatin 10, monomethyl dolastatin 10, auristain E, monomethyl auristain E (MMAE), auristatin F, monomethyl auristatin F, HTI-286, tubulysin M, maytansinoid AP-3, cryptophycin, Boc-Val-Dil-Dap-OH, tubulysin IM-1, Boc-Val-Dil-Dap-Phe-OMe, tubulysin IM-2, Boc-Nme-Val-Val-Dil-Dap-OH, tubulysin IM-3, and colchicine DA; DNA-alkylators (duocarmycin analogs) such as, for example, duocarmycin SA, duocarmycin CN, duocarmycin DMG, duocarmycin DMA, duocarmycin MA, duocarmycin TM, duocarmycin MB, duocarmycin GA; tomaymycin DM; SJG-136; illudin S; irofulven; apaziquone; triptolide; staurosporine; camptothecin; methotrexate; and other anti-cancer drugs such as, for example, kinase inhibitors, histone deacetylase (HDAC) inhibitors, proteasome inhibitors, and matrix metalloproteinase (MMP) inhibitors. In an embodiment, the drug is MMAE or PBD dimer.

The polypeptides, proteins, CARs, or anti-CD276 binding moieties described herein may be conjugated to (b) an effector molecule directly or indirectly, e.g., via a linking moiety. The linking moiety may be any suitable linking moiety known in the art. In an embodiment, the linking moiety is a cleavable linker that may be cleaved upon administration of the conjugate to a mammal. Examples of linking moieties that may be suitable for use in the inventive conjugates include, but are not limited to, peptide prodrug linking moieties such as, for example, the linking moieties having chemical structures (1) and (2); disulfide prodrug linking moieties such as, for example, the linking moieties having chemical structures (3) and (4); bifunctional linking moieties such as, for example, the linking moieties having chemical structures (5) and (6); thiol-reactive linking moieties such as, for example, the linking moieties having chemical structures (7) and (8); oxime/aldehyde linking moieties such as, for example, the linking moieties having chemical structures (9) and (10); ethylene glycol-based linking moieties such as, for example, the linking moiety having chemical structure (11), and the linking moiety having chemical structure (12)

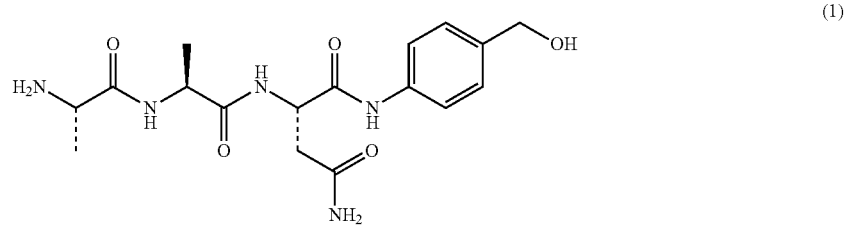

(1)

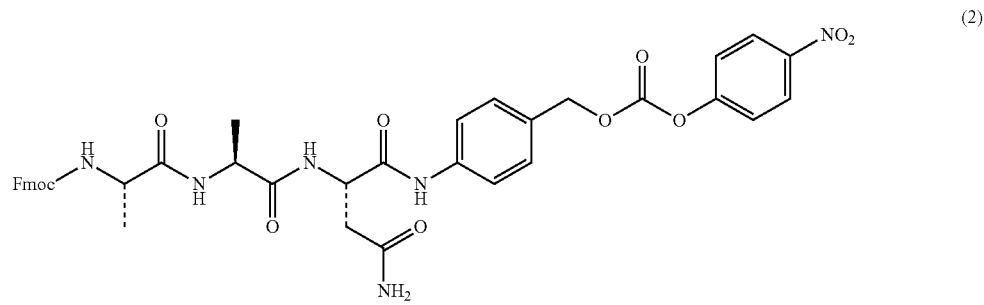

(2)

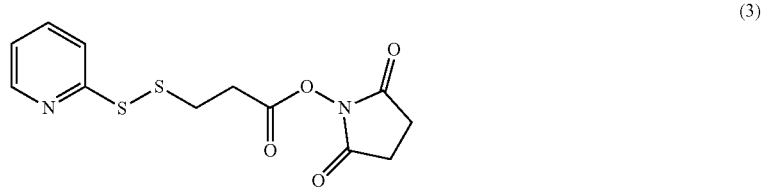

(3)

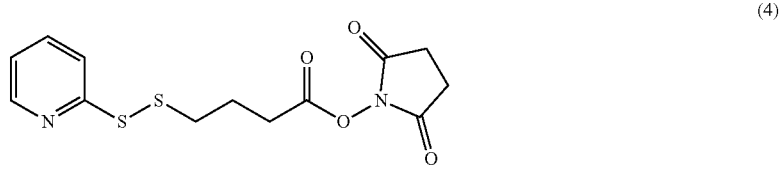

(4)

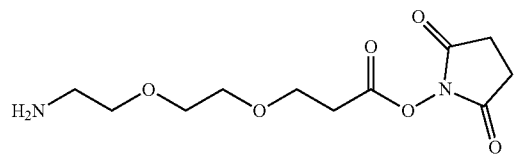
(5)
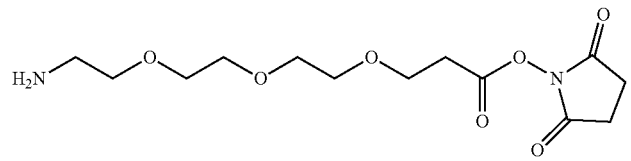
(6)
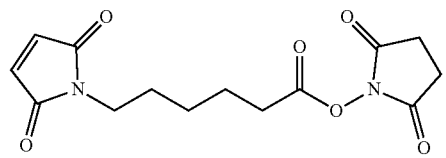
(7)
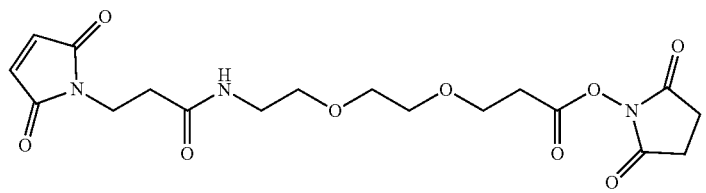
(8)
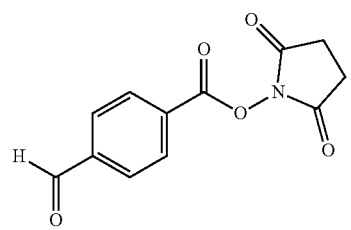
(9)
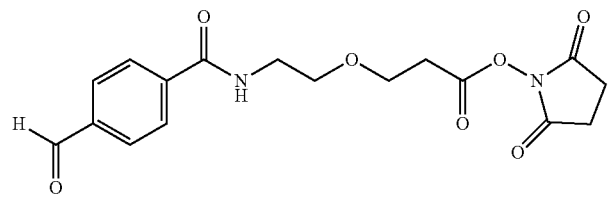
(10)
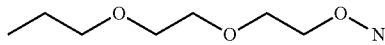
(11)
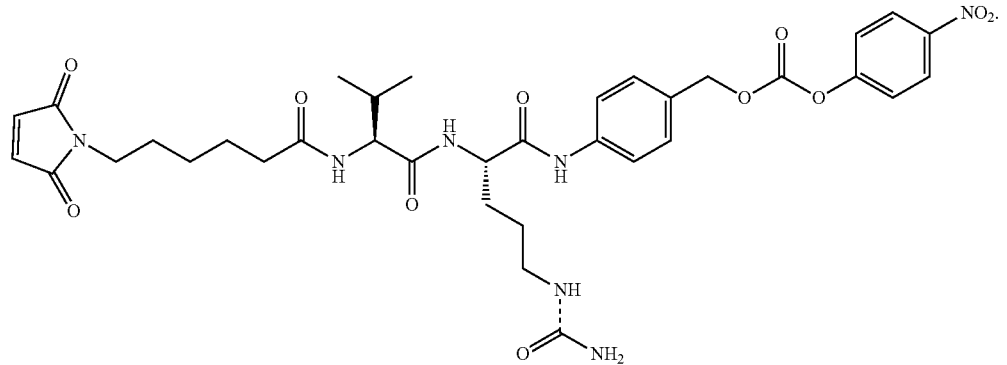
(12)

Another embodiment of the invention provides a conjugate comprising

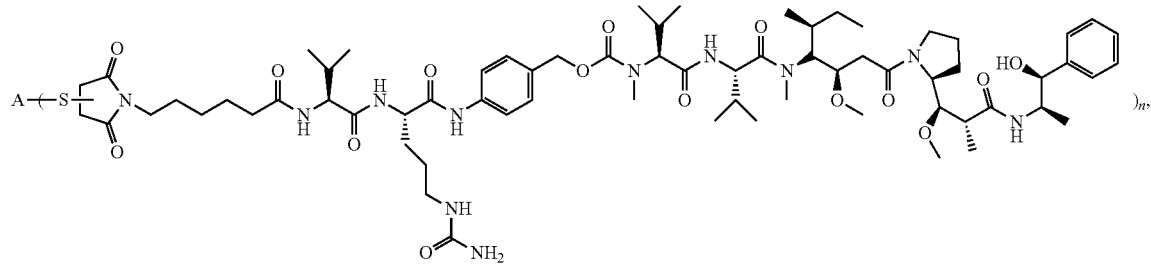

wherein:
n is an even integer, preferably an even integer from 0 to 8, more preferably an even integer from 0 to 4 (for example, n is 2, 4, 6, or 8); and
A is any of the polypeptides, proteins, or anti-CD276 binding moieties described herein with respect to other aspects of the invention, preferably an anti-CD276 binding moiety comprising the amino acid sequences of SEQ ID NOs: 26 and 27.

In an embodiment of the invention, the anti-CD276 polypeptide, anti-CD276 protein, or the anti-CD276 binding moiety of the inventive conjugate is conjugated to the effector molecule by next-generation site-specific conjugation technology. Examples of next-generation site-specific conjugation technologies include, but are not limited to, SNAP site-specific antibody drug conjugate (ADC) linker technology available from Igenica Biotherapeutics (Burlingame, Calif.) and SMARTAG technology available from Catalent Pharma Solutions (Woodstock, Ill.).

Further provided by an embodiment of the invention is a nucleic acid comprising a nucleotide sequence encoding any of the polypeptides, proteins, CARs, anti-CD276 binding moieties, conjugates, or functional portions or functional variants thereof. The nucleic acids of the invention may comprise a nucleotide sequence encoding any of the leader sequences, linkers, antigen binding domains, immunoglobulin domains, transmembrane domains, and/or intracellular T cell signaling domains described herein. For example, the nucleic acids may comprise a nucleotide sequence encoding a leader, the nucleotide sequence comprising SEQ ID NO: 42, 43, or 44. Alternatively or additionally, the nucleic acids may comprise a nucleotide sequence encoding a linker, the nucleotide sequence comprising SEQ ID NO: 59. Alternatively or additionally, the nucleic acids may comprise a nucleotide sequence encoding an immunoglobulin constant domain, the nucleotide sequence comprising SEQ ID NO: 46. Alternatively or additionally, the nucleic acids may comprise a nucleotide sequence encoding a transmembrane domain comprising CD28 and an intracellular T cell signaling domain comprising CD28 and CD3 zeta, the nucleotide sequence comprising SEQ ID NO: 50. Alternatively or additionally, the nucleic acids may comprise a nucleotide sequence encoding a transmembrane domain comprising CD8 and an intracellular T cell signaling domain comprising CD28, CD137, and CD3 zeta, the nucleotide sequence comprising SEQ ID NO: 52. Alternatively or additionally, the nucleic acids may comprise a nucleotide sequence encoding a transmembrane domain comprising CD8 and an intracellular T cell signaling domain comprising CD137 and CD3 zeta, the nucleotide sequence comprising SEQ ID NO: 51.

An embodiment of the invention provides a nucleic acid comprising a nucleotide sequence encoding any of the polypeptides, proteins, or anti-CD276 binding moieties described herein. In this regard, the nucleic acid comprises a nucleotide sequence encoding first and second variable regions (i) SEQ ID NOs: 53 and 54, (ii) SEQ ID NOs: 55 and 56, or (iii) SEQ ID NOs: 57 and 58, respectively. Another embodiment of the invention provides a nucleic acid comprising a nucleotide sequence encoding any of the CARs described herein.

"Nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In some embodiments, the nucleic acid does not comprise any insertions, deletions, inversions, and/or substitutions. However, it may be suitable in some instances, as discussed herein, for the nucleic acid to comprise one or more insertions, deletions, inversions, and/or substitutions. In some embodiments, the nucleic acid may encode additional amino acid sequences that do not affect the function of the polypeptide, protein, or CAR and which may or may not be translated upon expression of the nucleic acid by a host cell (e.g., AAA). In an embodiment of the invention, the nucleic acid is complementary DNA (cDNA). In an embodiment of the invention, the nucleic acid comprises a codon-optimized nucleotide sequence.

The nucleic acids of an embodiment of the invention may be recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acids can consist essentially of the specified nucleotide sequence or sequences described herein, such that other components, e.g., other nucleotides, do not materially change the biological activity of the encoded CAR, polypeptide, protein, anti CD276-binding moieties, functional portion, or functional variant.

A recombinant nucleic acid may be one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques, such as those described in Green et al., supra. The nucleic acids can be constructed based on chemical synthesis and/or enzymatic ligation reactions using procedures known in the art. See, for example, Green et al., supra, and Ausubel et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, Colo.) and Synthegen (Houston, Tex.).

The nucleic acid can comprise any isolated or purified nucleotide sequence which encodes any of the polypeptides, proteins, CARs, anti-CD276 binding moieties, conjugates, or functional portions or functional variants thereof. Alternatively, the nucleotide sequence can comprise a nucleotide sequence which is degenerate to any of the sequences or a combination of degenerate sequences.

An embodiment of the invention also provides an isolated or purified nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions may hybridize under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive polypeptides, proteins, CARs, anti-CD276 binding moieties, conjugates, or functional portions or functional variants thereof. It is generally appreciated that conditions can be rendered more stringent by the addition of increasing amounts of formamide.

The invention also provides a nucleic acid comprising a nucleotide sequence that is at least about 70% or more, e.g., about 80%, about 90%, about 91%, about 92%, about 93%, about 94%, about 95%, about 96%, about 97%, about 98%, or about 99% identical to any of the nucleic acids described herein.

In an embodiment, the nucleic acids of the invention can be incorporated into a recombinant expression vector. In this regard, an embodiment of the invention provides recombinant expression vectors comprising any of the nucleic acids of the invention. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring or non-naturally-occurring internucleotide linkages, or both types of linkages. Preferably, the non-naturally occurring or altered nucleotides or internucleotide linkages do not hinder the transcription or replication of the vector.

In an embodiment, the recombinant expression vector of the invention can be any suitable recombinant expression vector, and can be used to transform or transfect any suitable host cell. Suitable vectors include those designed for propagation and expansion or for expression or both, such as plasmids and viruses. The vector can be selected from the group consisting of the pUC series (Fermentas Life Sciences, Glen Burnie, Md.), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λZapII (Stratagene), λEMBL4, and λNM1149, also can be used. Examples of plant expression vectors include pBI01, pBI101.2, pBI101.3, pBI121 and pBIN19 (Clontech). Examples of animal expression vectors include pEUK-Cl, pMAM, and pMAMneo (Clontech). The recombinant expression vector may be a viral vector, e.g., a retroviral vector.

A number of transfection techniques are generally known in the art (see, e.g., Graham et al., *Virology,* 52: 456-467 (1973); Green et al., supra; Davis et al., *Basic Methods in Molecular Biology,* Elsevier (1986); and Chu et al., *Gene,* 13: 97 (1981). Transfection methods include calcium phosphate co-precipitation (see, e.g., Graham et al., supra), direct micro injection into cultured cells (see, e.g., Capecchi, *Cell,* 22: 479-488 (1980)), electroporation (see, e.g., Shigekawa et al., *BioTechniques,* 6: 742-751 (1988)), liposome mediated gene transfer (see, e.g., Mannino et al., *BioTechniques,* 6: 682-690 (1988)), lipid mediated transduction (see, e.g., Felgner et al., *Proc. Natl. Acad. Sci. USA,* 84: 7413-7417

(1987)), and nucleic acid delivery using high velocity microprojectiles (see, e.g., Klein et al., *Nature,* 327: 70-73 (1987)).

In an embodiment, the recombinant expression vectors of the invention can be prepared using standard recombinant DNA techniques described in, for example, Green et al., supra, and Ausubel et al., supra. Constructs of expression vectors, which are circular or linear, can be prepared to contain a replication system functional in a prokaryotic or eukaryotic host cell. Replication systems can be derived, e.g., from ColEl, 2μ plasmid, λ, SV40, bovine papilloma virus, and the like.

The recombinant expression vector may comprise regulatory sequences, such as transcription and translation initiation and termination codons, which are specific to the type of host cell (e.g., bacterium, fungus, plant, or animal) into which the vector is to be introduced, as appropriate, and taking into consideration whether the vector is DNA- or RNA-based. The recombinant expression vector may comprise restriction sites to facilitate cloning.

The recombinant expression vector can include one or more marker genes, which allow for selection of transformed or transfected host cells. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleotide sequence encoding the polypeptides, proteins, CARs, anti-CD276 binding moieties, conjugates, or functional portions or functional variants thereof, or to the nucleotide sequence which is complementary to or which hybridizes to the nucleotide sequence encoding the inventive polypeptides, proteins, CARs, anti-CD276 binding moieties, conjugates, or functional portions or functional variants thereof. The selection of promoters, e.g., strong, weak, inducible, tissue-specific and developmental-specific, is within the ordinary skill of the artisan. Similarly, the combining of a nucleotide sequence with a promoter is also within the ordinary skill of the artisan. The promoter can be a non-viral promoter or a viral promoter, e.g., a cytomegalovirus (CMV) promoter, an SV40 promoter, an RSV promoter, or a promoter found in the long-terminal repeat of the murine stem cell virus.

The inventive recombinant expression vectors can be designed for either transient expression, for stable expression, or for both. Also, the recombinant expression vectors can be made for constitutive expression or for inducible expression.

Further, the recombinant expression vectors can be made to include a suicide gene. As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art (see, for example, *Suicide Gene Therapy: Methods and Reviews*, Springer, Caroline J. (Cancer Research UK Centre for Cancer Therapeutics at the Institute of Cancer Research, Sutton, Surrey, UK), Humana Press, 2004) and include, for example, the Herpes Simplex Virus (HSV) thymidine kinase (TK) gene, cytosine daminase, purine nucleoside phosphorylase, and nitroreductase.

An embodiment of the invention further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5α *E. coli* cells, Chinese hamster ovarian cells, monkey VERO cells, COS cells, HEK293 cells, and the like. For purposes of amplifying or replicating the recombinant expression vector, the host cell may be a prokaryotic cell, e.g., a DH5α cell. For purposes of producing a recombinant polypeptide, protein, CAR, anti-CD276 binding moiety, conjugate, or functional portion or functional variant thereof, the host cell may be a mammalian cell. The host cell may be a human cell. While the host cell can be of any cell type, can originate from any type of tissue, and can be of any developmental stage, the host cell may be a peripheral blood lymphocyte (PBL) or a peripheral blood mononuclear cell (PBMC). The host cell may be a B cell or a T cell.

For purposes herein, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. The T cell may be a human T cell. The T cell may be a T cell isolated from a human. The T cell can be any type of T cell and can be of any developmental stage, including but not limited to, $CD4^+/CD8^+$ double positive T cells, $CD4^+$ helper T cells, e.g., $Th_1$ and $Th_2$ cells, $CD8^+$ T cells (e.g., cytotoxic T cells), tumor infiltrating cells, memory T cells, naïve T cells, and the like. The T cell may be a $CD8^+$ T cell or a $CD4^+$ T cell.

Also provided by an embodiment of the invention is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cell, a muscle cell, a brain cell, etc. Alternatively, the population of cells can be a substantially homogeneous population, in which the population comprises mainly host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

The polypeptides, proteins, CARs (including functional portions and variants thereof), nucleic acids, recombinant expression vectors, host cells (including populations thereof), anti-CD276 binding moieties, and conjugates, all of which are collectively referred to as "inventive anti-CD276 materials" hereinafter, can be isolated and/or purified. The term "isolated" as used herein means having been removed from its natural environment. The term "purified" or "isolated" does not require absolute purity or isolation; rather, it is intended as a relative term. Thus, for example, a purified (or isolated) host cell preparation is one in which the host cell is more pure than cells in their natural environment within the body. Such host cells may be produced, for example, by standard purification techniques. In some embodiments, a preparation of a host cell is purified such that the host cell represents at least about 50%, for example, at least about 70%, of the total cell content of the preparation. For example, the purity can be at least about 50%, can be greater than about 60%, about 70% or about 80%, or can be about 100%.

The inventive anti-CD276 materials can be formulated into a composition, such as a pharmaceutical composition. In this regard, an embodiment of the invention provides a pharmaceutical composition comprising any of the inventive anti-CD276 materials described herein and a pharmaceutically acceptable carrier. The inventive pharmaceutical compositions containing any of the inventive anti-CD276 materials can comprise more than one inventive anti-CD276 material, e.g., a conjugate and a nucleic acid, or two or more different conjugates Alternatively, the pharmaceutical composition can comprise an inventive anti-CD276 material in combination with other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc. In a preferred embodiment, the pharmaceutical composition comprises the inventive conjugate.

The inventive anti-CD276 materials can be provided in the form of a salt, e.g., a pharmaceutically acceptable salt. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, for example, p-toluenesulphonic acid.

With respect to pharmaceutical compositions, the pharmaceutically acceptable carrier can be any of those conventionally used and is limited only by chemico-physical considerations, such as solubility and lack of reactivity with the active agent(s), and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the active agent(s) and one which has no detrimental side effects or toxicity under the conditions of use.

The choice of carrier will be determined in part by the particular inventive anti-CD276 material, as well as by the particular method used to administer the inventive anti-CD276 material. Accordingly, there are a variety of suitable formulations of the pharmaceutical composition of the invention. Preservatives may be used. Suitable preservatives may include, for example, methylparaben, propylparaben, sodium benzoate, and benzalkonium chloride. A mixture of two or more preservatives optionally may be used. The preservative or mixtures thereof are typically present in an amount of about 0.0001% to about 2% by weight of the total composition.

Suitable buffering agents may include, for example, citric acid, sodium citrate, phosphoric acid, potassium phosphate, and various other acids and salts. A mixture of two or more buffering agents optionally may be used. The buffering agent or mixtures thereof are typically present in an amount of about 0.001% to about 4% by weight of the total composition.

The concentration of inventive anti-CD276 material in the pharmaceutical formulations can vary, e.g., from less than about 1%, usually at or at least about 10%, to as much as, for example, about 20% to about 50% or more by weight, and can be selected primarily by fluid volumes, and viscosities, in accordance with the particular mode of administration selected.

Methods for preparing administrable (e.g., parenterally administrable) compositions are known or apparent to those skilled in the art and are described in more detail in, for example, *Remington: The Science and Practice of Pharmacy*, Lippincott Williams & Wilkins; 21st ed. (May 1, 2005).

The following formulations for oral, aerosol, parenteral (e.g., subcutaneous, intravenous, intraarterial, intramuscular, intradermal, interperitoneal, and intrathecal), and topical administration are merely exemplary and are in no way limiting. More than one route can be used to administer the inventive anti-CD276 materials, and in certain instances, a particular route can provide a more immediate and more effective response than another route.

Formulations suitable for oral administration can comprise or consist of (a) liquid solutions, such as an effective amount of the inventive anti-CD276 material dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant. Capsule forms can be of the ordinary hard or softshelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and other pharmacologically compatible excipients. Lozenge forms can comprise the inventive anti-CD276 material in a flavor, usually sucrose and acacia or tragacanth, as well as pastilles comprising the inventive anti-CD276 material in an inert base, such as gelatin and glycerin, or sucrose and acacia, emulsions, gels, and the like containing, in addition to, such excipients as are known in the art.

Formulations suitable for parenteral administration include aqueous and nonaqueous isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The inventive anti-CD276 material can be administered in a physiologically acceptable diluent in a pharmaceutical carrier, such as a sterile liquid or mixture of liquids, including water, saline, aqueous dextrose and related sugar solutions, an alcohol, such as ethanol or hexadecyl alcohol, a glycol, such as propylene glycol or polyethylene glycol, dimethylsulfoxide, glycerol, ketals such as 2,2-dimethyl-1,3-dioxolane-4-methanol, ethers, poly(ethyleneglycol) 400, oils, fatty acids, fatty acid esters or glycerides, or acetylated fatty acid glycerides with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations will typically contain, for example, from about 0.5% to about 25% by weight of the inventive anti-CD276 material in solution. Preservatives and buffers may be used. In order to minimize or eliminate irritation at the site of injection, such compositions may contain one or more nonionic surfactants having, for example, a hydrophile-lipophile balance (HLB) of from about 12 to about 17. The quantity of surfactant in such formulations will typically range, for example, from about 5% to about 15% by weight. Suitable surfactants include polyethylene glycol sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Injectable formulations are in accordance with an embodiment of the invention. The requirements for effective pharmaceutical carriers for injectable compositions are well-known to those of ordinary skill in the art (see, e.g., *A Practical Guide to Contemporary Pharmacy Practice*, 3rd Edition, Lippincott Williams and Wilkins, Philadelphia, Pa., Thompson and Davidow, eds., (2009), and *Handbook on Injectable Drugs*, Trissel, 16th ed., (2010)).

Topical formulations, including those that are useful for transdermal drug release, are well known to those of skill in the art and are suitable in the context of embodiments of the invention for application to skin. The inventive anti-CD276 material, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer. Such spray formulations also may be used to spray mucosa.

An "effective amount" or "an amount effective to treat" refers to a dose that is adequate to (a) prevent or treat cancer or (b) reduce or eliminate tumor vasculature in an individual. Amounts effective for a therapeutic or prophylactic use will depend on, for example, the stage and severity of the disease or disorder being treated, the age, weight, and general state of health of the patient, and the judgment of the prescribing physician. The size of the dose will also be determined by the active selected, method of administration, timing and frequency of administration, the existence, nature, and extent of any adverse side-effects that might accompany the administration of a particular active, and the desired physiological effect. It will be appreciated by one of skill in the art that various diseases or disorders could require prolonged treatment involving multiple administrations, perhaps using the inventive anti-CD276 materials in each or various rounds of administration. By way of example and not intending to limit the invention, the dose of the inventive anti-CD276 material can be about 0.001 to about 1000 mg/kg body weight of the subject being treated/day, from about 0.01 to about 10 mg/kg body weight/day, about 0.01 mg to about 1 mg/kg body weight/day.

For purposes of the invention, the amount or dose of the inventive anti-CD276 material administered should be sufficient to effect a therapeutic or prophylactic response in the subject or animal over a reasonable time frame. For example, the dose of the inventive anti-CD276 material should be sufficient to bind to antigen, detect, reduce, or eliminate tumor vasculature, or detect, treat or prevent disease in a period of from about 2 hours or longer, e.g., about 12 to about 24 or more hours, from the time of administration. In certain embodiments, the time period could be even longer. The dose will be determined by the efficacy of the particular inventive anti-CD276 material and the condition of the animal (e.g., human), as well as the body weight of the animal (e.g., human) to be treated.

For purposes of the invention, an assay, which comprises, for example, comparing the extent to which target cells are killed upon administration of a given dose of the inventive anti-CD276 material to a mammal, among a set of mammals of which is each given a different dose of the inventive anti-CD276 material, could be used to determine a starting dose to be administered to a mammal. The extent to which target cells are killed upon administration of a certain dose can be assayed by methods known in the art.

In addition to the aforedescribed pharmaceutical compositions, the inventive anti-CD276 materials can be formulated as inclusion complexes, such as cyclodextrin inclusion complexes, or liposomes. Liposomes can serve to target the inventive anti-CD276 materials to a particular tissue. Liposomes also can be used to increase the half-life of the inventive anti-CD276 materials. Many methods are available for preparing liposomes, as described in, for example, Szoka et al., *Ann. Rev. Biophys. Bioeng.*, 9, 467 (1980) and U.S. Pat. Nos. 4,235,871, 4,501,728, 4,837,028, and 5,019,369.

The delivery systems useful in the context of embodiments of the invention may include time-released, delayed release, and sustained release delivery systems such that the delivery of the inventive composition occurs prior to, and with sufficient time to cause, sensitization of the site to be treated. The inventive composition can be used in conjunction with other therapeutic agents or therapies. Such systems can avoid repeated administrations of the inventive composition, thereby increasing convenience to the subject and the physician, and may be particularly suitable for certain composition embodiments of the invention.

Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are lipids including sterols such as cholesterol, cholesterol esters, and fatty acids or neutral fats such as mono-di-and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the active composition is contained in a form within a matrix such as those described in U.S. Pat. Nos. 4,452,775, 4,667,014, 4,748,034, and 5,239,660 and (b) diffusional systems in which an active component permeates at a controlled rate from a polymer such as described in U.S. Pat. Nos. 3,832,253 and 3,854,480. In addition, pump-based hardware delivery systems can be used, some of which are adapted for implantation.

One of ordinary skill in the art will readily appreciate that the inventive anti-CD276 materials of the invention can be modified in any number of ways, such that the therapeutic or prophylactic efficacy of the inventive anti-CD276 materials is increased through the modification. For instance, the inventive anti-CD276 materials can be modified into a depot form, such that the manner in which the inventive anti-CD276 materials is released into the body to which it is administered is controlled with respect to time and location within the body (see, for example, U.S. Pat. No. 4,450,150). Depot forms of inventive anti-CD276 materials can be, for example, an implantable composition comprising the inventive anti-CD276 materials and a porous or non-porous material, such as a polymer, wherein the inventive anti-CD276 materials are encapsulated by or diffused throughout the material and/or degradation of the non-porous material. The depot is then implanted into the desired location within the body and the inventive anti-CD276 materials are released from the implant at a predetermined rate.

When the inventive anti-CD276 materials are administered with one or more additional therapeutic agents, one or more additional therapeutic agents can be coadministered to the mammal. By "coadministering" is meant administering one or more additional therapeutic agents and the inventive anti-CD276 materials sufficiently close in time such that the inventive anti-CD276 materials can enhance the effect of one or more additional therapeutic agents, or vice versa. In this regard, the inventive anti-CD276 materials can be administered first and the one or more additional therapeutic agents can be administered second, or vice versa. Alternatively, the inventive anti-CD276 materials and the one or more additional therapeutic agents can be administered simultaneously. An exemplary therapeutic agent that can be co-administered with the anti-CD276 materials is IL-2. It is believed that IL-2 enhances the therapeutic effect of the inventive anti-CD276 materials. For purposes of the inventive methods, wherein host cells or populations of cells are administered to the mammal, the cells can be cells that are allogeneic or autologous to the mammal.

It is contemplated that the inventive anti-CD276 materials and pharmaceutical compositions can be used in methods of treating or preventing a disease in a mammal. Without being bound to a particular theory or mechanism, the inventive anti-CD276 materials have biological activity, e.g., ability to recognize antigen, e.g., CD276, such that the anti-CD276 material, can direct an effector molecule to a target cell or target tissue. In this regard, an embodiment of the invention provides a method of (a) treating or preventing cancer or (b) reducing or eliminating tumor vasculature in a mammal, comprising administering to the mammal any of the polypeptides, proteins, CARs, functional portions, functional variants, nucleic acids, recombinant expression vectors, host cells, population of cells, anti-CD276 binding moieties, conjugates, and/or the pharmaceutical compositions of the invention in an amount effective to (a) treat or prevent cancer or (b) reduce or eliminate tumor vasculature in the mammal.

An embodiment of the invention further comprises lymphodepleting the mammal prior to administering the inventive anti-CD276 materials. Examples of lymphodepletion include, but may not be limited to, nonmyeloablative lymphodepleting chemotherapy, myeloablative lymphodepleting chemotherapy, total body irradiation, etc.

For purposes of the inventive methods, wherein host cells or populations of cells are administered, the cells can be cells that are allogeneic or autologous to the mammal. Preferably, the cells are autologous to the mammal.

The mammal referred to herein can be any mammal. As used herein, the term "mammal" refers to any mammal, including, but not limited to, mammals of the order Rodentia, such as mice and hamsters, and mammals of the order Logomorpha, such as rabbits. The mammals may be from the order Carnivora, including Felines (cats) and Canines (dogs). The mammals may be from the order Artiodactyla, including Bovines (cows) and Swines (pigs) or of the order Perssodactyla, including Equines (horses). The mammals may be of the order Primates, Ceboids, or Simoids (monkeys) or of the order Anthropoids (humans and apes). Preferably, the mammal is a human.

With respect to the inventive methods, the cancer can be any cancer, including any of acute lymphocytic cancer, acute myeloid leukemia, rhabdomyosarcoma, bladder cancer (e.g., bladder carcinoma), bone cancer, brain cancer (e.g., medulloblastoma, neuroblastoma, and glioblastoma), breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, Ewing's sarcoma, esophageal cancer, cervical cancer, fibrosarcoma, gastrointestinal carcinoid tumor, head and neck cancer (e.g., head and neck squamous cell carcinoma), Hodgkin lymphoma, hypopharynx cancer, kidney cancer, larynx cancer, leukemia, liquid tumors, liver cancer, lung cancer (e.g., non-small cell lung carcinoma), lymphoma, malignant mesothelioma, mastocytoma, melanoma, multiple myeloma, nasopharynx cancer, neuroblastoma, non-Hodgkin lymphoma, B-chronic lymphocytic leukemia, hairy cell leukemia, acute lymphocytic leukemia (ALL), and Burkitt's lymphoma, ovarian cancer, pancreatic cancer, peritoneum, omentum, and mesentery cancer, pharynx cancer, prostate cancer, rectal cancer, renal cancer, skin cancer, small intestine cancer, soft tissue cancer, solid tumors, stomach cancer, testicular cancer, thyroid cancer, and ureter cancer. Preferably, the cancer is a solid tumor (e.g., pediatric solid tumor), adult carcinoma, neuroblastoma, glioblastoma, Ewing's sarcoma, rhabdomyosarcoma, prostate cancer, ovarian cancer, colorectal cancer, or lung cancer. In an embodiment, the cancer is characterized by the expression or overexpression of CD276.

Without being bound by a particular theory or mechanism, it is believed that vasculature (e.g., tumor vasculature) may be a CD276 expressing target. Accordingly, in an embodiment of the invention, the cancer is not characterized by the expression or overexpression of CD276 in areas other than tumor vasculature.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the disease, or a symptom or condition thereof.

Another embodiment of the invention provides a kit for (a) treating or preventing cancer or (b) reducing tumor vasculature, the kit comprising any of the polypeptides, proteins, anti-CD276 binding moieties, conjugates, nucleic acids, recombinant expression vectors, isolated host cells, populations of cells, or pharmaceutical compositions described herein with respect to other aspects of the invention. In a preferred embodiment, the kit comprises a conjugate comprising tions, functional variants, nucleic acids, recombinant expression vectors, host cells, population of cells, anti-CD276 binding moieties, conjugates, or pharmaceutical compositions of the invention for (a) the treatment or prevention of cancer or (b) the reduction or elimination of tumor vasculature in a mammal.

Another embodiment of the invention provides a method of detecting the presence of (a) cancer or (b) tumor vasculature in a mammal, comprising: (a) contacting a sample comprising one or more cells from the mammal with any of the polypeptides, proteins, CARs, functional portions, functional variants, nucleic acids, recombinant expression vectors, host cells, population of cells, anti-CD276 binding moieties, or conjugates of the invention, thereby forming a complex, (b) and detecting the complex, wherein detection of the complex is indicative of the presence of (a) cancer or (b) tumor vasculature in the mammal.

The sample may be obtained by any suitable method, e.g., biopsy or necropsy. A biopsy is the removal of tissue and/or cells from an individual. Such removal may be to collect tissue and/or cells from the individual in order to perform experimentation on the removed tissue and/or cells. This experimentation may include experiments to determine if the individual has and/or is suffering from a certain condition or disease-state. The condition or disease may be, e.g., cancer.

With respect to an embodiment of the inventive method of detecting the presence of (a) cancer or (b) tumor vasculature in a mammal, the sample comprising cells of the mammal can be a sample comprising whole cells, lysates thereof, or a fraction of the whole cell lysates, e.g., a nuclear or cytoplasmic fraction, a whole protein fraction, or a nucleic

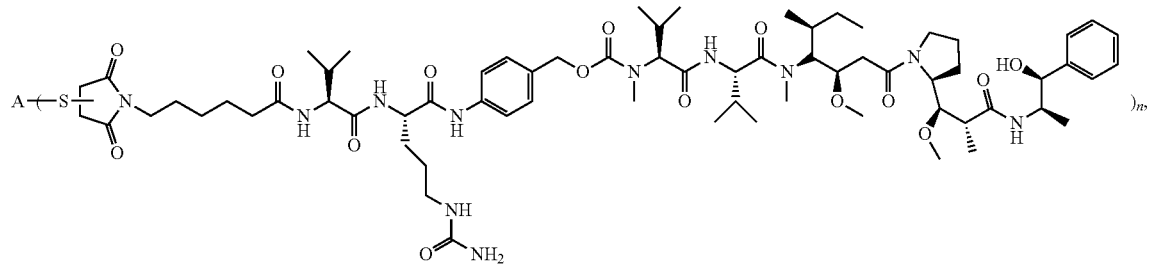

wherein:

n is an even integer, and

A is an anti-CD276 binding moiety comprising the amino acid sequences of SEQ ID NOs: 26 and 27. An embodiment of the kit may further comprise any one or more of (a) pharmaceutically acceptable carrier(s) as described herein with respect to other aspects of the invention (e.g., buffering agent(s)); (b) printed instructions for using the kit; (c) one or more other pharmaceutically active agent(s) or drug(s), such as chemotherapeutic agent(s), as described herein with respect to other aspects of the invention. The printed instructions for using the kit may recite methods of administering the inventive anti-CD276 material(s) as described herein with respect to other aspects of the invention. An embodiment of the kit further comprises separate containers for holding each of the one or more pharmaceutically acceptable carrier(s), each of the one or more inventive anti-CD276 material(s), and each of the one or more other pharmaceutically active agent(s) or drug(s).

Another embodiment of the invention provides a use of any of the polypeptides, proteins, CARs, functional poracid fraction. If the sample comprises whole cells, the cells can be any cells of the mammal, e.g., the cells of any organ or tissue, including blood cells or endothelial cells.

For purposes of the inventive detecting method, the contacting can take place in vitro or in vivo with respect to the mammal. Preferably, the contacting is in vitro.

Also, detection of the complex can occur through any number of ways known in the art. For instance, the inventive CARs, polypeptides, proteins, functional portions, functional variants, nucleic acids, recombinant expression vectors, host cells, populations of cells, anti-CD276 binding moieties, or conjugates, described herein, can be labeled with a detectable label such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

Methods of testing an anti-CD276 material for the ability to recognize target cells and for antigen specificity are known in the art. For instance, Clay et al., *J. Immunol.*, 163: 507-513 (1999), teaches methods of measuring the release of cytokines (e.g., interferon-γ, granulocyte/monocyte colony stimulating factor (GM-CSF), tumor necrosis factor a (TNF-α) or interleukin 2 (IL-2)). In addition, anti-CD276 material function can be evaluated by measurement of cellular cytotoxicity, as described in Zhao et al., *J. Immunol.*, 174: 4415-4423 (2005).

The following examples further illustrate the invention but, of course, should not be construed as in any way limiting its scope.

EXAMPLE 1

This example demonstrates the identification, purification, and characterization of anti-CD276 binding domains.
Yeast Display Naïve Human Antibody Library, Antibodies, Biotinylation Kit, Cells A large yeast display naïve single chain variable fragment (scFv) human antibody library was constructed using a collection of human antibody gene repertoires, including the genes used for the construction of a phage display Fab library (Zhu et al., *Methods Mol. Biol.*, 525: 129-142, xv (2009)).

Mouse monoclonal anti-c-Myc antibody was purchased from Roche (Pleasanton, Calif.). PE-conjugated streptavidin and Alexa-488 conjugated goat anti-mouse antibody were purchased from Invitrogen (Carlsbad, Calif.). Protein G columns were purchased from GE healthcare (Waukesha, Wis.). Avi-tag specific biotinylation kits were purchased from Avidity (Aurora, Colo.). Yeast plasmid extraction kits were purchased from Zymo Research (Irvine, Calif.). 293 free style protein expression kits were purchased from Invitrogen. An AutoMACS System was purchased from Miltenyi Biotec (Cologne, Germany).
MACS Sorting Downsize of the Initial Yeast Display Human Antibody Library Biotinylated human and mouse CD276 extracellular domain was used as the target for three rounds of sorting to downsize the initial yeast display naïve human antibody library. Approximately 1010 cells from the initial naïve antibody library and 10 μg of biotinylated CD276 ecto-domain were incubated in 50 ml PBSA (phosphate-buffered saline containing 0.1% bovine serum albumin) at room temperature (RT) for 2 hr with rotation. The mixture of biotinylated CD276 ecto-domain bound to displayed antibody on cells from the library was washed three times with PBSA and incubated with 100 μl of streptavidin conjugated microbeads at RT from Miltenyi Biotec. The resultant mixture was washed once with PBSA and loaded onto the AutoMACS system for the first round of sorting. The sorted cells were amplified in SDCAA media (20 g dextrose, 6.7 g DIFCO yeast nitrogen base without (w/o) amino acids, 5 g BACTO casamino acids, 5.4 g $Na_2HPO_4$ and 8.56 g $NaH_2PO_4.H_2O$ in 1 liter water) at 30° C. and 250 revolutions per minute (rpm) for 24 hours (hr). The culture was then induced in SGCAA media (20 g galactose, 20 g raffinose, 1 g dextrose, 6.7 g DIFCO yeast nitrogen base w/o amino acids, 5 g BACTO casamino acids, 5.4 g $Na_2HPO_4$ and 8.56 g $NaH_2PO_4.H_2O$ in 1 liter water) at 20° C. and 250 rpm for 16-18 hr.

The same amounts of antigen and incubation volume were used for the next two rounds of sorting. The cell numbers used for these two rounds of sorting were set at 100 times the size of the sorted pool from the previous round of sorting to keep the diversity of each sorted pool.
Expression and Purification of scFv-Fc Proteins Plasmids were extracted from the identified yeast clones using yeast plasmid extraction kits (Zymo Research, Irvine, Calif.), following the manufacturer's instructions. Extracted plasmids were transformed into 10G chemical competent *E. coli* (Lucigen, Middleton, Wis.) for further amplification. Plasmids extracted from the bacteria were used for DNA sequencing to obtain the nucleic acid sequences encoding the positive binder antibodies.

Three anti-CD276 antibodies were identified, each comprising heavy and light chain amino acid sequences as follows: (1) Clone m852 (comprising a heavy chain comprising SEQ ID NO: 7 and a light chain comprising SEQ ID NO: 8), (2) Clone m857 (comprising a heavy chain comprising SEQ ID NO: 17 and a light chain comprising SEQ ID NO: 18), and (3) Clone m8524 (m276) (comprising a heavy chain comprising SEQ ID NO: 26 and a light chain comprising SEQ ID NO: 27).

Figure 1:
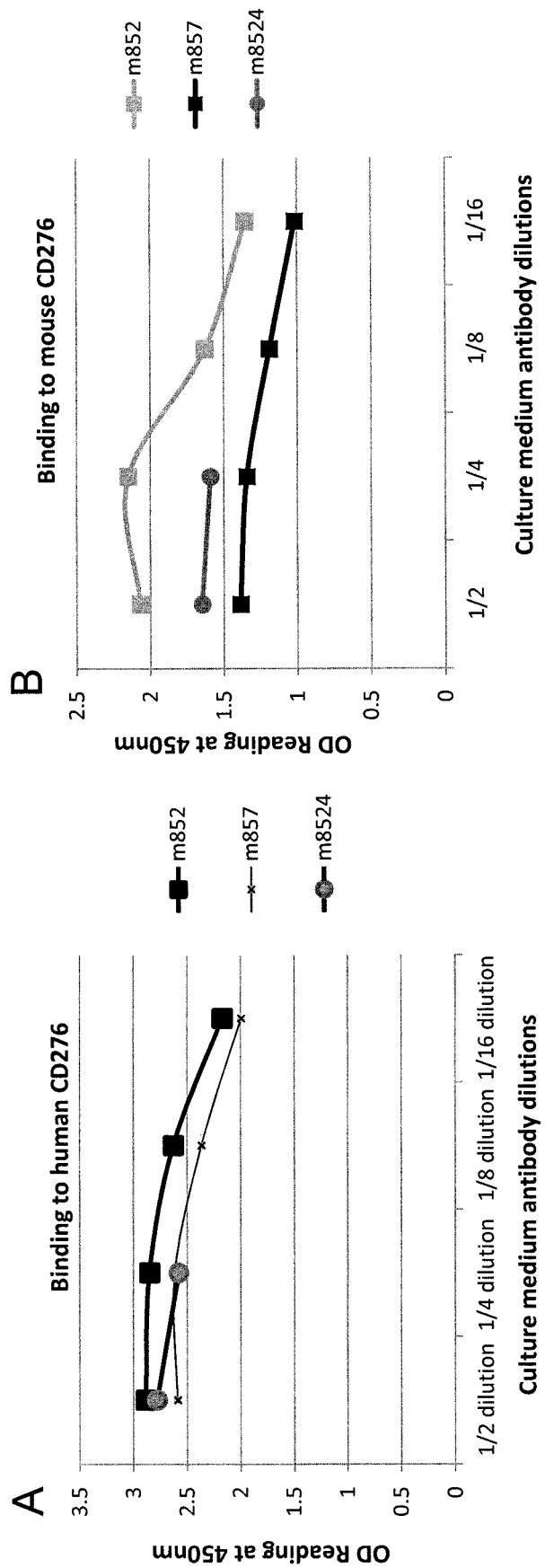
FIG. 1A is a graph showing the optical density (OD) reading at 450 nm as measured in an ELISA binding assay for scFv-Fc fusion proteins comprising heavy and light chain amino acid sequences as follows: (1) Clone m852 (comprising a heavy chain comprising SEQ ID NO: 7 and a light chain comprising SEQ ID NO: 8) (squares), (2) m857 (comprising a heavy chain comprising SEQ ID NO: 17 and a light chain comprising SEQ ID NO: 18) ("x"), and (3) m8524 (m276) (comprising a heavy chain comprising SEQ ID NO: 26 and a light chain comprising SEQ ID NO: 27) (circles), incubated with human CD276 at the dilutions indicated.
FIG. 1B is a graph showing the OD reading at 450 nm as measured in an ELISA binding assay for scFv-Fc fusion proteins comprising heavy and light chain amino acid sequences as follows: (1) Clone m852 (comprising a heavy chain comprising SEQ ID NO: 7 and a light chain comprising SEQ ID NO: 8) (grey squares), (2) m857 (comprising a heavy chain comprising SEQ ID NO: 17 and a light chain comprising SEQ ID NO: 18) (black squares), and (3) m8524 (m276) (comprising a heavy chain comprising SEQ ID NO: 26 and a light chain comprising SEQ ID NO: 27) (circles), incubated with mouse CD276 at the dilutions indicated.
Figure 2:
FIG. 2 is a graph showing the binding affinity (response, (RU)) of Clone m8524 (m276) (comprising a heavy chain comprising SEQ ID NO: 26 and a light chain comprising SEQ ID NO: 27) to human CD276 over time (seconds, (s)) as measured by surface plasmon resonance at KD=4.9×10$^{-11}$ M. The figure shows that both the line corresponding to the raw data and the line generated by the software when the fitting was performed to calculate the KD are practically the same.

The scFv-encoding inserts of the unique clones were digested with SfiI and ligated into modified pSecTag bearing the same set of SfiI sites and Fc-Avi tag for soluble expression. These constructs were transfected into 293T cells for expression following the manufacturer's protocol. After 72 hr of growth, the scFv-Fc fusion proteins in the culture medium were used for the ELISA binding assay.
ELISA Binding Assay 50 μl of the diluted human (FIG. 1A) or mouse (FIG. 1B) CD276-AP fusion protein in PBS at 2 μg/ml was coated in a 96-well plate at 4° C. overnight. Transiently expressed scFv-Fc fusion protein in the culture medium was serially diluted and added into the target protein coated wells. After washing, a 1:3000 diluted horseradish peroxidase (HRP) conjugated goat anti-human IgG antibody was added for 1 hr at RT. After washing, 3, 3, 5, 5'-Tetramethylbenzidine (TMB) substrate was added, and the optical density (O.D.) was read at 450 nm. The results are shown in FIGS. 1A and 1B. As shown in FIGS. 1A and 1B, scFv-Fc fusion proteins comprising heavy and light chain amino acid sequences as follows: (1) Clone m852 (comprising a heavy chain comprising SEQ ID NO: 7 and a light chain comprising SEQ ID NO: 8), (2) m857 (comprising a heavy chain comprising SEQ ID NO: 17 and a light chain comprising SEQ ID NO: 18), and (3) m8524 (m276) (comprising a heavy chain comprising SEQ ID NO: 26 and a light chain comprising SEQ ID NO: 27) each bound to both human (FIG. 1A) and mouse (FIG. 1B) CD276.
Affinity Determination by Surface Plasmon Resonance Binding affinities of human anti-CD276 scFv m8524 to human CD276 Ecto-domain were analyzed by surface plasmon resonance technology using a Biacore X100 instrument (GE healthcare). The human CD276 soluble extracellular domain was covalently immobilized onto a sensor chip (CM5) using carbodiimide coupling chemistry. A control reference surface was prepared for nonspecific binding and refractive index changes. For analysis of the kinetics of interactions, varying concentrations of antigens were injected at a flow rate of 30 μl/min using running buffer containing 10 mM HEPES, 150 mM NaCl, 3 mM EDTA, and 0.05% Surfactant P-20 (pH 7.4). The association and dissociation phase data were fitted simultaneously to a 1:1 Langumir global model, using the nonlinear data analysis program BIAevaluation 3.2. All of the experiments were done at 25° C. The affinity of the antibody m8524 (m276) (comprising a heavy chain comprising SEQ ID NO: 26 and a light chain comprising SEQ ID NO: 27) is shown in FIG. 2. FIG. 2 shows that both the line corresponding to the raw data and the line generated by the software when the fitting was performed to calculate the KD are practically the same.

EXAMPLE 2

This example demonstrates that the growth of subcutaneous HCT116 human colon xenograft tumors is impaired in CD276 knockout (KO) mice.

Figure 3:
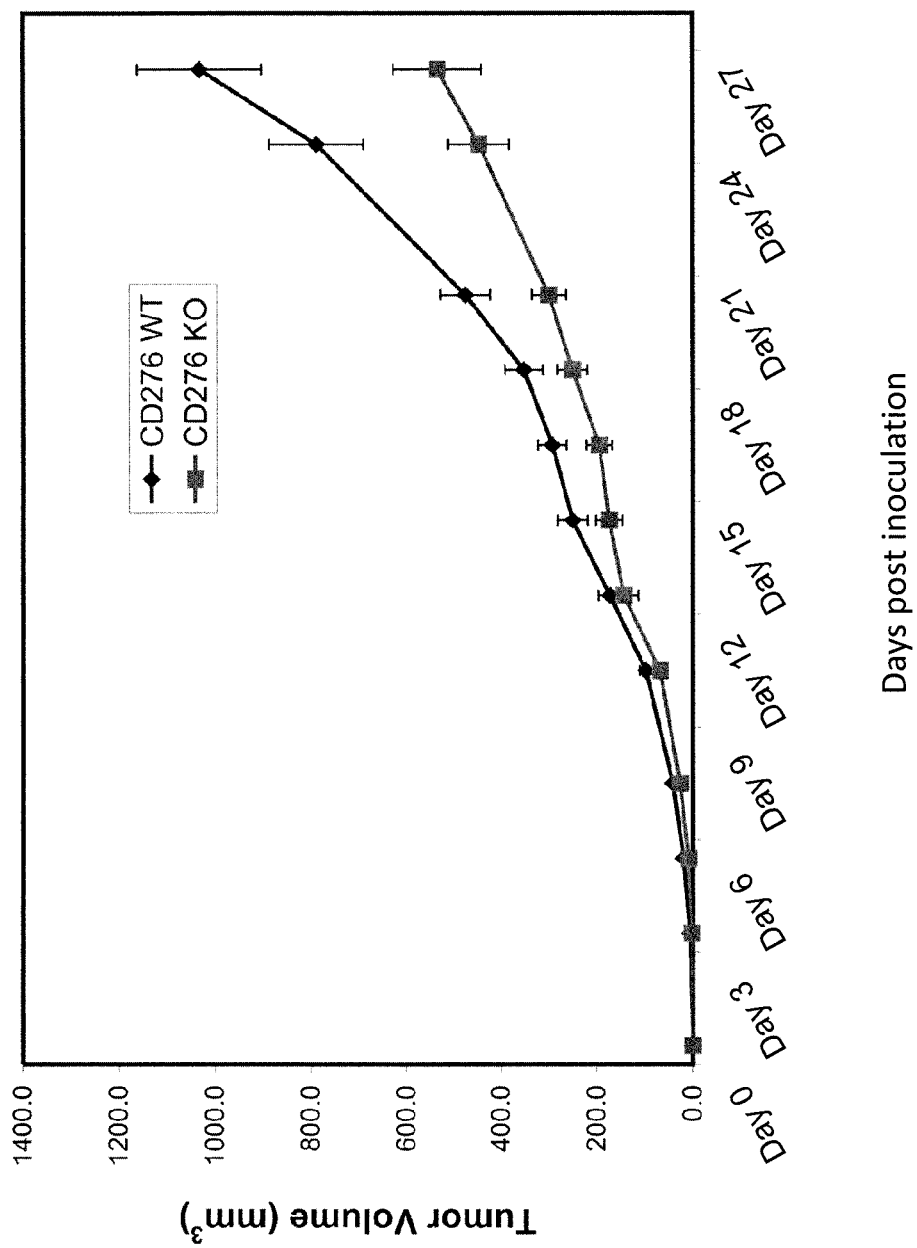
FIG. 3 is a graph showing the volume of tumor (mm$^3$) measured in wild-type (WT) (diamonds) and CD276 knockout (KO) (squares) mice at various time points (days) following inoculation with HCT116 human colon cells.

Wild-type (WT) and CD276 KO mice were inoculated with HTC116 human colon tumor cells and the tumor volume was measured about every three days over a period of about one month following inoculation. The results are shown in FIG. 3. As shown in FIG. 3, the growth of subcutaneous HCT116 human colon xenograft tumors is impaired in CD276 KO mice.

EXAMPLE 3

This example demonstrates the binding of the anti-CD276 scFv-Fc m8524 (m276) to mouse and human CD276 expressed on a cell surface.

Figure 4:
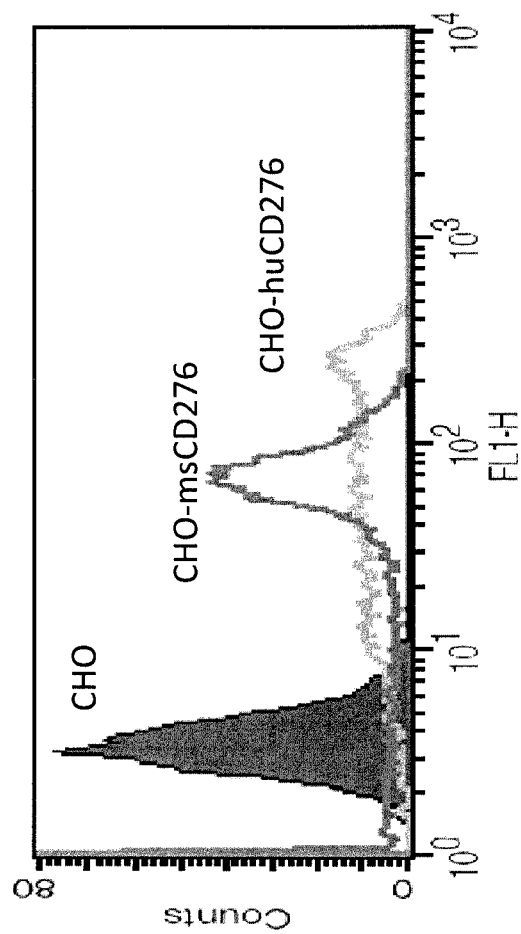
FIG. 4 is a graph showing the number of counts measured by flow cytometry indicating the level of binding of anti-CD276 scFv-Fc (m8524) (SEQ ID NOs: 26 and 27) to Chinese hamster ovary cells that were untransduced (CHO)

Chinese hamster ovary (CHO) cells were untransduced or transduced to express mouse CD276 or human CD276. The cells were cultured with 1 µg/100 µl of the anti-CD276 scFv-Fc m8524 (m276) (SEQ ID NOs: 26 and 27) (primary antibody) and fluorescein isothiocyanate (FITC) Gt anti-human antibody (H+L) (as a secondary antibody). The binding of the anti-CD276 scFv-Fc m8524 (m276) to mouse or human CD276 expressed on the cell surface was measured by flow cytometry. The results are shown in FIG. 4. As shown in FIG. 4, the anti-CD276 scFv-Fc m8524 (m276) bound to mouse and human CD276 expressed on the cell surface.

EXAMPLE 4

This example demonstrates the specific binding of human anti-CD276 antibody m8524 IgG1 to tumor vasculature in WT and CD276 KO mice with Pan 02 pancreatic adenocarcinoma tumors.

CD276 KO mice and CD276 WT mice each bearing Pan02 pancreatic adenocarcinoma tumors were injected (IP) with FITC-labeled 8524 IgG1 (SEQ ID NOs: 26 and 27) and anti-CD31/anti-Meca32. Anti-Meca32 is a monoclonal antibody with specificity for mouse endothelium. Immunofluorescence staining revealed the co-localization of the human anti-CD276 antibody m8524 IgG1 (green staining) with anti-CD31/anti-Meca32-positive tumor vasculature (red staining) in CD276 WT mice. Red staining was observed in the tumor vasculature of CD276 KO mice. However, the lack of green staining in the CD276 KO mice confirmed the specificity of the antibody for host vasculature.

EXAMPLE 5

This example demonstrates the specific binding of FITC-labeled human anti-CD276 antibody m8524 IgG1 to human CD276 expressed on the surface of human embryonic kidney (HEK) 293 cells.

HEK293 cells were untransduced or transduced to express human CD276. The cells were cultured with FITC-labeled human anti-CD276 antibody m8524 IgG1 (SEQ ID NOs: 26 and 27). The binding of the FITC-labeled human anti-CD276 antibody m8524 IgG1 to human CD276 expressed on the cell surface was measured by flow cytometry. The results are shown in FIG. 5. As shown in FIG. 5, flow cytometry revealed the increased binding of human anti-CD276 antibody m8524 to CD276-transfected 293 cells (293/CD276) as compared to non-transfected parent 293 cells.

EXAMPLE 6

This example demonstrates the localization of FITC-labeled, human anti-CD276 antibody (m8524 IgG1) to human tumor cells, but not vasculature, after intraperitoneal (IP) injection into tumor-bearing, CD276 KO mice.

CD276-positive, Pan02 pancreatic adenocarcinoma tumor-bearing, CD276 KO mice were injected (IP) with FITC-labeled 8524 IgG1 (SEQ ID NOs: 26 and 27) (green staining) and anti-CD31/anti-Meca32 (red staining). CD31/Meca32 positive vessels were stained red. Human tumor cells were stained green. Separate photographic images of the green and red staining were taken, and the images of the red and green staining were merged to provide a third image wherein co-localization of red and green staining provided a yellow signal. No yellow signal was observed in the merged image due to the lack of CD276 expression in the host-derived CD276-null vessels, resulting in no co-localization (yellow signal) in the merged image. The images showed that the FITC-labeled human anti-CD276 antibody (m8524 IgG1) localized to human tumor cells but not vasculature following injection into tumor-bearing CD276 KO mice.

EXAMPLE 7

This example demonstrates the localization of FITC-labeled, human anti-CD276 antibody (m8524 IgG1) to both human tumor cells and vasculature after IP injection into tumor-bearing, CD276 WT mice.

CD276-positive, Pan02 pancreatic adenocarcinoma tumor-bearing, CD276 WT mice were injected (IP) with FITC-labeled 8524 IgG1 (SEQ ID NOs: 26 and 27) (green staining) and anti-CD31/anti-Meca32 (red staining). CD31/Meca32 positive vessels were stained red. Human tumor cells were stained green. Separate photographic images of the green and red staining were taken, and the images of the red and green staining were merged to provide a third image wherein co-localization of red and green staining provided a yellow signal. A yellow signal was observed in the merged image due to the presence of CD276 expression in the host-derived CD276-positive vessels, resulting in co-localization (yellow signal) in the merged image. The images showed that FITC-labeled human anti-CD276 antibody (m8524 IgG1) localized to both human tumor cells and tumor vasculature following injection into tumor-bearing CD276 WT mice.

EXAMPLE 8

This example demonstrates that anti-CD276 antibody (m8524 IgG1) stains tumor cells and tumor vasculature but not normal liver.

CD276 KO mice and CD276 WT mice each bearing Pan02 pancreatic adenocarcinoma tumors were injected (IP) with FITC-labeled 8524 IgG1 (SEQ ID NOs: 26 and 27) and anti-CD31/anti-Meca32. CD31/Meca32 positive vessels in the normal liver of both CD276 KO and CD276 WT mice and in the tumor vasculature of CD276 WT mice were stained red. Human tumor cells and tumor vasculature were stained green in the CD276 WT mice. Separate photographic images of the green and red staining in the tumor of CD276 WT mice were taken, and the images of the red and green staining were merged to provide a third image wherein co-localization of red and green staining provided a yellow signal. It was observed that the anti-CD276 mAb (m8524 IgG1; green) stained tumor cells and tumor vasculature in CD276 WT mice but not the normal liver of the CD276 WT or the CD276 KO mice. A yellow signal was observed in the merged image of the tumor of CD276 WT mice. The yellow signal indicated the co-localization of the CD31/Meca32 staining (red) with the CD276 staining (green).

EXAMPLE 9

This example demonstrates that anti-CD276 antibody (m8524 IgG1) stains tumor cells and tumor vasculature but not normal tissues.

CD276 WT mice bearing Pan02 pancreatic adenocarcinoma tumors were injected (IP) with FITC-labeled 8524 IgG1 (SEQ ID NOs: 26 and 27) and anti-CD31/anti-Meca32. CD31/Meca32 positive vessels in normal tissues, including the brain, heart, intestines, liver, muscle, spleen, and stomach of the CD276 WT mice were stained red. Pan02 tumors served as a positive control for the staining of all normal tissues. CD31/Meca32 positive vessels in the tumor vasculature of CD276 WT mice were also stained red. Human tumor cells and tumor vasculature were stained green in the CD276 WT mice. Separate photographic images of the green and red staining in the tumor of CD276 WT mice were taken, and the images of the red and green staining were merged to provide a third image wherein co-localization of red and green staining provided a yellow signal. It was observed that the anti-CD276 mAb (m8524) stained tumor cells (green) and tumor vasculature (yellow signal, indicating co-localization with anti-CD31/anti-Meca32) in the CD276 WT mice. However, the anti-CD276 mAb (m8524) did not stain any of the normal tissues from CD276 WT mice.

EXAMPLE 10

This example demonstrates the co-immunofluorescence labeling of intrahepatic MC38 tumors at the normal liver/tumor margin by anti-CD276 antibody (m8524 IgG1).

Samples of the normal liver/tumor margin of MC38 (colon cancer)-tumor bearing, WT mice were post-stained with FITC-labeled human anti-CD276 antibody (m8524 IgG1) (SEQ ID NOs: 26 and 27) (FIG. 6B) or laminin (FIG. 6A). Photographic images were taken. The results are shown in FIGS. 6A and 6B. As shown in FIG. 6A, laminin stained the vessels in both the normal and the tumor tissue. As shown in FIG. 6B, the anti-CD276 antibody (m8524 IgG1) stained tumor cells but not normal tissue located at the normal liver/tumor margin.

EXAMPLE 11

This example demonstrates the preparation of an anti-CD276 antibody-drug conjugate (ADC).

An ADC (m8524-ADC) was prepared including the m8524 antibody conjugated to MMAE via a linking moiety. Reagents used to prepare the m8524-ADC included the linking moiety with chemical structure (12), MMAE with chemical structure (13), and MMAE conjugated to the linking moiety, which had chemical structure (14):

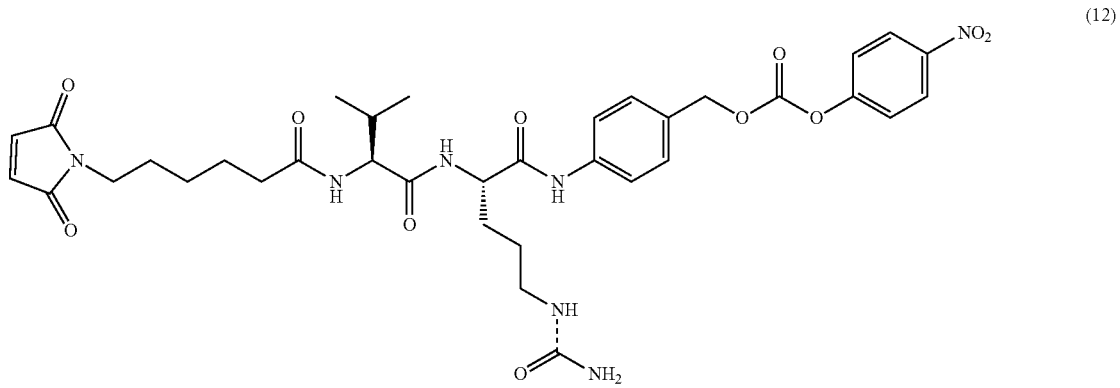

(12)

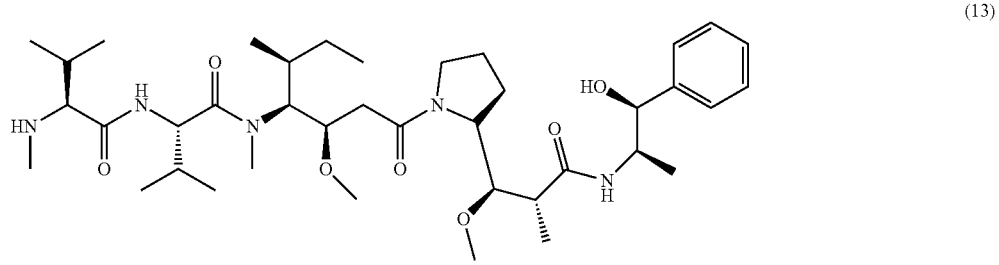

(13)

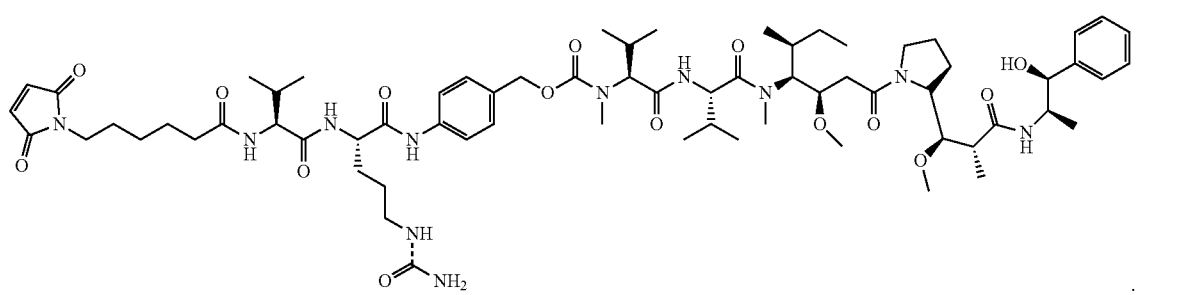

(14)

The m8524-ADC had chemical structure (15):

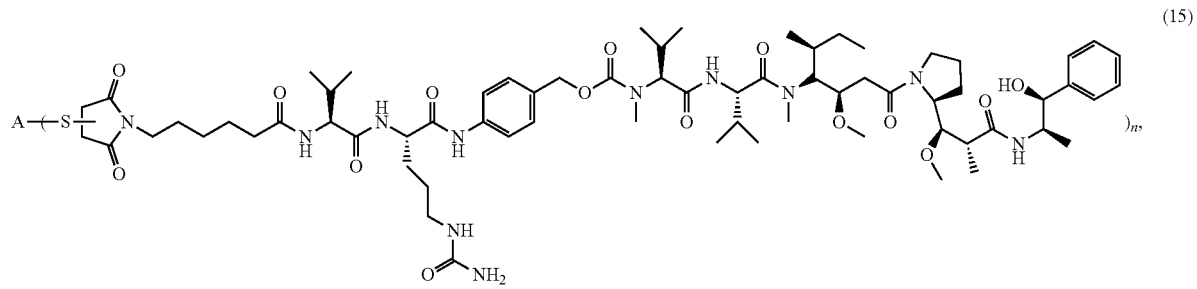

(15)

wherein:
n is 2, 4, 6, or 8, and
A is an anti-CD276 antibody comprising the amino acid sequences of SEQ ID NOs: 26 and 27.

EXAMPLE 12

This example demonstrates that immunofluorescence staining for CD276 reveals low levels of CD276 in HEK 293 untransduced cells and high levels of CD276 in 293/CD276 cells stably transfected with CD276.

HEK 293 cells or HEK 293 cells transduced with CD276 (293/CD276) were co-cultured with an irrelevant human IgG control antibody, an irrelevant ADC control, or m8524-ADC. The drug of the ADCs was MMAE.

The nuclei of the cells were counterstained blue with DAPI. Photographic images were taken. Immunofluorescence staining for CD276 (green) revealed low levels of CD276 in untransduced 293 cells and high levels of CD276 in 293 cells that were transduced with CD276.

EXAMPLE 13

This example demonstrates that an m8524 antibody drug conjugate (ADC) is selectively cytotoxic toward CD276-expressing cells.

HEK 293 cells (293) or HEK 293 cells transduced with CD276 (293/CD276) were treated with MMAE alone, m8524 (m276) (SEQ ID NOs: 26 and 27) antibody alone, m825 (irrelevant control antibody)-ADC, or m8524-ADC. The drug of the ADCs was MMAE. The cells were treated with the MMAE, ADC, or antibody at the various concentrations shown in FIG. 7. As shown in FIG. 7, MMAE free drug was cytotoxic to all cells and displayed no selectivity for CD276-expressing cells. The 293 cells and 293/CD276 cells were resistant to killing by CD276 naked antibodies (m8524) or MMAE-conjugated antibodies against another target. The anti-CD276 antibodies conjugated to MMAE (m8524-ADC) were selectively cytotoxic towards 293/CD276 and 293 cells, with toxicity corresponding to CD276 expression levels.

EXAMPLE 14

This example demonstrates the in vivo efficacy of CD276 ADCs against human colon cancer xenografts in athymic nude mice.

Athymic nude mice bearing HCT-116 human colon cancer xenografts were treated with control (vehicle), m8524 (m276) (SEQ ID NOs: 26 and 27) alone (30 mg/kg (mpk)), or m8524 (m276)-MMAE ADCs at various dosages (1 mpk, 3 mpk, 10 mpk, or 30 mpk) twice a week for three weeks. Tumor volume was measured at various time points after administration. The results are shown in FIGS. 8 and 9. As shown in FIGS. 8 and 9, the tumor volume in mice treated with m8524 (m276)-MMAE ADC decreased as compared to the tumor volume in mice treated with control or m8524 (m276) alone.

Athymic nude mice bearing HT29 human colorectal adenocarcinoma xenografts were treated with control (vehicle), m8524 (m276) (SEQ ID NOs: 26 and 27) alone (10 mg/kg (mpk)), or m8524 (m276)-MMAE ADCs at various dosages (1 mpk, 3 mpk, or 10 mpk) twice a week for three weeks. Tumor volume was measured at various time points after administration. The results are shown in FIG. 10. As shown in FIG. 10, the tumor volume in mice treated with m8524 (m276)-MMAE ADC decreased as compared to the tumor volume in mice treated with control or m8524 (m276) alone.

Athymic nude mice bearing KM12 human colon carcinoma xenografts were treated with control (vehicle), m8524 (m276) (SEQ ID NOs: 26 and 27) alone (10 mg/kg (mpk)), or m8524 (m276)-MMAE ADCs at various dosages (1 mpk, 3 mpk, or 10 mpk) twice weekly for 3 weeks, followed by a 2 day break, followed by another dose twice weekly for 3 weeks. Tumor volume was measured at various time points after administration. The results are shown in FIG. 11. As shown in FIG. 11, the tumor volume in mice treated with m8524 (m276)-MMAE ADC decreased as compared to the tumor volume in mice treated with control or m8524 (m276) alone.

EXAMPLE 15

This example demonstrates the in vivo efficacy of CD276 ADCs against human ovarian cancer xenografts in SCID mice.

SCID mice bearing OVCAR3 human ovarian xenografts were treated with control (vehicle), m8524 (m276) (SEQ ID NOs: 26 and 27) alone (10 mg/kg (mpk)), MMAE alone (0.2 mpk), or m8524 (m276)-MMAE ADCs at various dosages (1 mpk, 3 mpk, or 10 mpk) on days 1, 4, 8 and 11. Tumor volume was measured at various time points after administration. The results are shown in FIG. 12 (up to Day 11) and FIG. 15 (up to Day 53). As shown in FIGS. 12 and 15, the tumor volume in mice treated with m8524 (m276)-MMAE ADC decreased as compared to the tumor volume in mice treated with control, MMAE alone, or m8524 (m276) alone.

EXAMPLE 16

This example demonstrates the in vitro cytotoxic efficacy of CD276 ADCs against HCT116, HT29, and OVCAR3 cancer cell lines.

HCT116, HT29, KM12 or OVCAR3 cells were cultured with m8524-MMAE ADC at the concentrations shown in FIG. 13. Cell viability was measured, and the results are shown in FIG. 13. As shown in FIG. 13, m8524-MMAE ADC treatment decreased the viability of HCT116, HT29, and OVCAR3 cells.

EXAMPLE 17

This example demonstrates the in vivo efficacy of CD276 ADCs against colon cancer in immunocompetent mice.

C57BL/6 mice bearing syngeneic MC38 murine colon cancer tumors were treated with control (vehicle), or 1 mpk m8524(m276)-PBD ADC twice weekly for two weeks. Treatments were initiated 11 days post tumor inoculation. Tumor volume was measured at various time points after administration. As shown in FIG. 14, the tumor volume in mice treated with the m8524(m276)-PBD ADC decreased as compared to the tumor volume in mice treated with vehicle alone.

EXAMPLE 18

This example demonstrates the in vivo efficacy of CD276 ADCs against human breast cancer xenografts in athymic nude mice.

MDA-MB231 human breast cancer cells were implanted in the mammary fat pad of athymic nude mice (orthotopic model). Tumor-bearing mice were treated with control (vehicle), m8524 (m276) (SEQ ID NOs: 26 and 27) alone (10 mg/kg (mpk)), or m8524 (m276)-MMAE ADCs (at a dose of 1 mpk or 10 mpk) twice weekly for 3 weeks. Tumor volume was measured at various time points after administration. The results are shown in FIG. 16. As shown in FIG. 16, the tumor volume in mice treated with m8524 (m276)-MMAE ADC decreased as compared to the tumor volume in mice treated with control or m8524 (m276) alone.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A polypeptide that specifically binds to CD276, comprising
   (i) heavy chain complementary determining regions (CDRs) of SEQ ID NO: 1, 2, and 3, and light chain CDRs of SEQ ID NO: 4, 5, and 6;
   (ii) heavy chain CDRs of SEQ ID NO: 11, 12, and 13, and light chain CDRs of SEQ ID NO: 14, 15, and 16; or
   (iii) heavy chain CDRs of SEQ ID NO: 20, 21, and 22, and light chain CDRs of SEQ ID NO: 23, 24, and 25.

2. The polypeptide of claim 1 comprising (i) SEQ ID NOs: 7 and 8, (ii) SEQ ID NOs: 17 and 18, or (iii) SEQ ID NOs: 26 and 27.

3. A protein that specifically binds to CD276, comprising a first polypeptide chain comprising complementary determining regions (CDRs) of (i) SEQ ID NOs: 1-3, (ii) SEQ ID NOs: 11-13, or (iii) SEQ ID NOs: 20-22 and a second polypeptide chain comprising CDRs of (i) SEQ ID NOs: 4-6, (ii) SEQ ID NOs: 14-16, or (iii) SEQ ID NOs: 23-25.

4. The protein of claim 3 comprising SEQ ID NO: 7, 17, or 26 and SEQ ID NO: 8, 18, or 27.

5. The polypeptide of claim 1 further comprising a linker.

6. The polypeptide of claim 5, wherein the linker comprises SEQ ID NO: 9 or 10.

7. An anti-CD276 binding moiety comprising the polypeptide of claim 1, wherein the anti-CD276 binding moiety is an antibody, Fab fragment (Fab), F(ab')$_2$ fragment, diabody, triabody, tetrabody, single-chain variable region fragment (scFv), or disulfide-stabilized variable region fragment (dsFv).

8. A conjugate comprising (a) the polypeptide of claim 1, conjugated to (b) an effector molecule.

9. The conjugate of claim 8, wherein the effector molecule is one or more of a pyrrolobenzodiazepine (PBD) dimer, drug, toxin, label, small molecule, antibody and monomethyl auristatin E (MMAE).

10. The conjugate according to claim 8 comprising

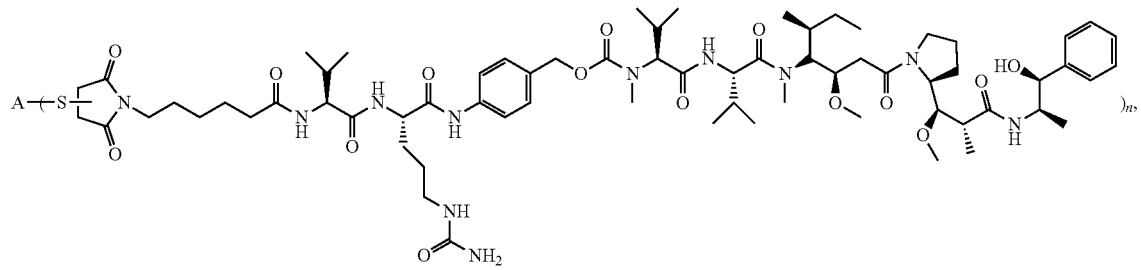

wherein:

n is an even integer, and

A is an anti-CD276 binding moiety comprising the amino acid sequences of SEQ ID NOs: 26 and 27.

11. The conjugate of claim 8 wherein (a) is conjugated to (b) by a site-specific conjugation.

12. A nucleic acid comprising a nucleotide sequence encoding the polypeptide of claim 1.

13. The nucleic acid according to claim 12, the nucleotide sequence comprising (i) SEQ ID NOs: 53 and 54, (ii) SEQ ID NOs: 55 and 56, or (iii) SEQ ID NOs: 57 and 58.

14. A recombinant expression vector comprising the nucleic acid of claim 12.

15. An isolated host cell comprising the recombinant expression vector of claim 14.

16. A population of cells comprising at least one host cell of claim 15, wherein the population of cells is not a human organism.

17. A pharmaceutical composition comprising the polypeptide of claim 1, and a pharmaceutically acceptable carrier.

18. A kit for (a) treating cancer or (b) reducing tumor vasculature, the kit comprising the polypeptide of claim 1.

19. The kit according to claim 18, wherein the kit comprises a conjugate comprising wherein:

n is an even integer, and

A is an anti-CD276 binding moiety comprising the amino acid sequences of SEQ ID NOs: 26 and 27.

20. A method of detecting the presence of (a) cancer or (b) tumor vasculature in a mammal, the method comprising:
(a) contacting a sample comprising one or more cells from the mammal with the polypeptide of claim 1, thereby forming a complex, and
(b) detecting the complex, wherein detection of the complex is indicative of the presence of (a) cancer or (b) tumor vasculature in the mammal.

21. The polypeptide of claim 2 further comprising a linker.

22. The protein of claim 3 further comprising a linker.

23. The protein of claim 4 further comprising a linker.

24. The protein of claim 3, wherein the linker comprises SEQ ID NO: 9 or 10.

25. An anti-CD276 binding moiety comprising the polypeptide of claim 3, wherein the anti-CD276 binding moiety is an antibody, Fab fragment (Fab), F(ab')$_2$ fragment, diabody, triabody, tetrabody, single-chain variable region fragment (scFv), or disulfide-stabilized variable region fragment (dsFv).

26. A conjugate comprising (a) the protein of claim 3 conjugated to (b) an effector molecule.

27. A conjugate comprising (a) the anti-CD276 binding moiety according to claim 7, conjugated to (b) an effector molecule.

28. The conjugate of claim 26, wherein the effector molecule is one or more of a pyrrolobenzodiazepine (PBD) dimer, drug, toxin, label, small molecule, antibody and monomethyl auristatin E (MMAE).

29. The conjugate of claim 27, wherein the effector molecule is one or more of a pyrrolobenzodiazepine (PBD) dimer, drug, toxin, label, small molecule, antibody and monomethyl auristatin E (MMAE).

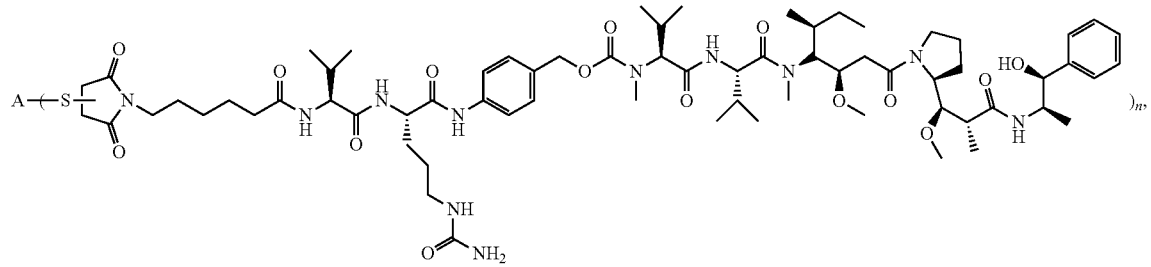

30. The conjugate according to claim 26 comprising

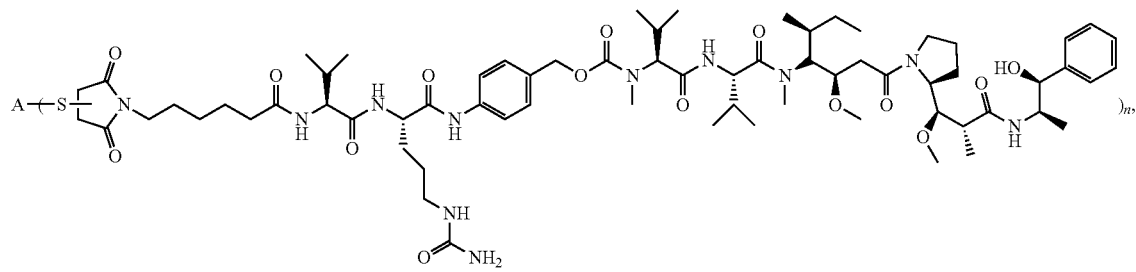

wherein:
n is an even integer, and
A is an anti-CD276 binding moiety comprising the amino acid sequences of SEQ ID NOs: 26 and 27.

31. The conjugate according to claim 27 comprising

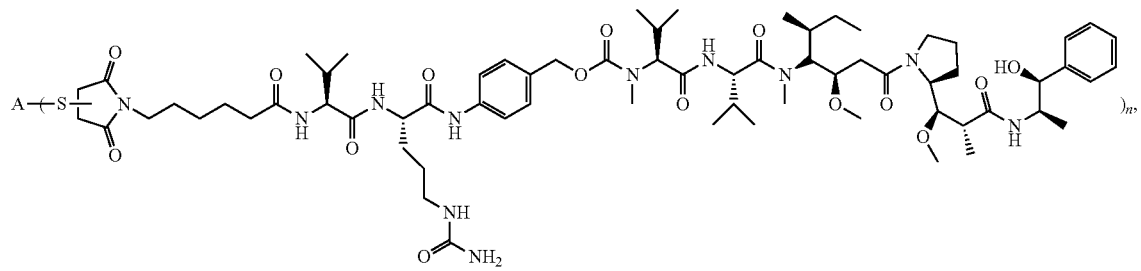

wherein:
n is an even integer, and
A is an anti-CD276 binding moiety comprising the amino acid sequences of SEQ ID NOs: 26 and 27.

32. A nucleic acid comprising a nucleotide sequence encoding the protein claim 3.

33. The nucleic acid according to claim 32, the nucleotide sequence comprising (i) SEQ ID NOs: 53 and 54, (ii) SEQ ID NOs: 55 and 56, or (iii) SEQ ID NOs: 57 and 58.

34. A pharmaceutical composition comprising the protein of claim 3, and a pharmaceutically acceptable carrier.

35. A kit for (a) treating cancer or (b) reducing tumor vasculature, the kit comprising the protein of claim 3.

36. The kit according to claim 35, wherein the kit comprises a conjugate comprising

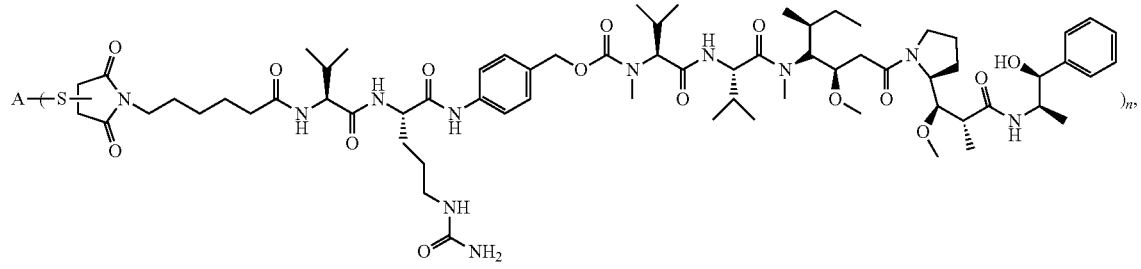

wherein:
n is an even integer, and
A is an anti-CD276 binding moiety comprising the amino acid sequences of SEQ ID NOs: 26 and 27.

37. A method of detecting the presence of (a) cancer or (b) tumor vasculature in a mammal, the method comprising:

(a) contacting a sample comprising one or more cells from the mammal with the protein of claim 3, thereby forming a complex, and
(b) detecting the complex, wherein detection of the complex is indicative of the presence of (a) cancer or (b) tumor vasculature in the mammal.

* * * * *

SEQUENCE LISTING

```
<160> NUMBER OF SEQ ID NOS: 59

<210> SEQ ID NO 1
<211> LENGTH: 8
<212> TYPE: PRT
<213> ORGANISM: Artificial Sequence
<220> FEATURE:
<223> OTHER INFORMATION: Synthetic

<400> SEQUENCE: 1

Gly Gly Thr Phe Ser Ser Tyr Ala
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic

<400> SEQUENCE: 2

Ile Ile Pro Ile Leu Gly Ile Ala
1               5
```

```
<210> SEQ ID NO 3
<211> LENGTH: 13
<212> TYPE: PRT
<213> ORGANISM: Artificial Sequence
<220> FEATURE:
<223> OTHER INFORMATION: Synthetic

<400> SEQUENCE: 3

Ala Arg Gly Arg Arg Ser Gly Ser Tyr Tyr Met Gly Tyr
1               5                   10

<210> SEQ ID NO 4
<211> LENGTH: 6
<212> TYPE: PRT
<213> ORGANISM: Artificial Sequence
<220> FEATURE:
<223> OTHER INFORMATION: Synthetic

<400> SEQUENCE: 4

Gln Ser Val Ser Ser Asn
1               5

<210> SEQ ID NO 5
<211> LENGTH: 3
<212> TYPE: PRT
<213> ORGANISM: Artificial Sequence
<220> FEATURE:
<223> OTHER INFORMATION: Synthetic

<400> SEQUENCE: 5

Asp Thr Ser
1

<210> SEQ ID NO 6
<211> LENGTH: 11
<212> TYPE: PRT
<213> ORGANISM: Artificial Sequence
<220> FEATURE:
<223> OTHER INFORMATION: Synthetic

<400> SEQUENCE: 6

Gln Gln Tyr Asn Asn Trp Pro Pro Ala Tyr Thr
1               5                   10

<210> SEQ ID NO 7
<211> LENGTH: 120
<212> TYPE: PRT
<213> ORGANISM: Artificial Sequence
<220> FEATURE:
<223> OTHER INFORMATION: Synthetic

<400> SEQUENCE: 7

Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Leu Gly Ile Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

```
Ala Arg Gly Arg Arg Ser Gly Ser Tyr Tyr Met Gly Tyr Trp Gly Gln
            100                 105                 110

Gly Thr Leu Val Thr Val Ser Ser
        115                 120

<210> SEQ ID NO 8
<211> LENGTH: 109
<212> TYPE: PRT
<213> ORGANISM: Artificial Sequence
<220> FEATURE:
<223> OTHER INFORMATION: Synthetic

<400> SEQUENCE: 8

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Asp Thr Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Ala Tyr Thr Phe Gly Gln Gly Thr Lys Leu Glu Ile Lys
            100                 105

<210> SEQ ID NO 9
<211> LENGTH: 17
<212> TYPE: PRT
<213> ORGANISM: Artificial Sequence
<220> FEATURE:
<223> OTHER INFORMATION: Synthetic

<400> SEQUENCE: 9

Ser Ser Gly Gly Gly Gly Ser Gly Gly Gly Gly Ser Gly Gly Gly Gly
1               5                   10                  15

Ser

<210> SEQ ID NO 10
<211> LENGTH: 15
<212> TYPE: PRT
<213> ORGANISM: Artificial Sequence
<220> FEATURE:
<223> OTHER INFORMATION: Synthetic

<400> SEQUENCE: 10

Gly Gly Gly Gly Ser Gly Gly Gly Gly Ser Gly Gly Gly Gly Ser
1               5                   10                  15

<210> SEQ ID NO 11
<211> LENGTH: 8
<212> TYPE: PRT
<213> ORGANISM: Artificial Sequence
<220> FEATURE:
<223> OTHER INFORMATION: Synthetic

<400> SEQUENCE: 11

Gly Gly Thr Phe Ser Ser Tyr Ala
1               5
```

<210> SEQ ID NO 12
<211> LENGTH: 8
<212> TYPE: PRT
<213> ORGANISM: Artificial Sequence
<220> FEATURE:
<223> OTHER INFORMATION: Synthetic

<400> SEQUENCE: 12

```
Ile Ile Pro Ile Leu Gly Ile Ala
1               5
```

<210> SEQ ID NO 13
<211> LENGTH: 12
<212> TYPE: PRT
<213> ORGANISM: Artificial Sequence
<220> FEATURE:
<223> OTHER INFORMATION: Synthetic

<400> SEQUENCE: 13

```
Ala Thr Gly Gly Ser Gly Ser Tyr Ala Phe Asp Ile
1               5                   10
```

<210> SEQ ID NO 14
<211> LENGTH: 6
<212> TYPE: PRT
<213> ORGANISM: Artificial Sequence
<220> FEATURE:
<223> OTHER INFORMATION: Synthetic

<400> SEQUENCE: 14

```
Gln Ser Val Ser Ser Tyr
1               5
```

<210> SEQ ID NO 15
<211> LENGTH: 3
<212> TYPE: PRT
<213> ORGANISM: Artificial Sequence
<220> FEATURE:
<223> OTHER INFORMATION: Synthetic

<400> SEQUENCE: 15

```
Asp Ala Ser
1
```

<210> SEQ ID NO 16
<211> LENGTH: 11
<212> TYPE: PRT
<213> ORGANISM: Artificial Sequence
<220> FEATURE:
<223> OTHER INFORMATION: Synthetic

<400> SEQUENCE: 16

```
Gln Gln Arg Ser Asn Trp Pro Pro Ser Tyr Thr
1               5                   10
```

<210> SEQ ID NO 17
<211> LENGTH: 119
<212> TYPE: PRT
<213> ORGANISM: Artificial Sequence
<220> FEATURE:
<223> OTHER INFORMATION: Synthetic

<400> SEQUENCE: 17

```
Gln Val Gln Leu Gln Gln Ser Gly Ala Glu Val Lys Lys Pro Gly Ser
1               5                   10                  15
Ser Val Lys Val Ser Cys Lys Ala Ser Gly Gly Thr Phe Ser Ser Tyr
            20                  25                  30
```

Ala Ile Ser Trp Val Arg Gln Ala Pro Gly Gln Gly Leu Glu Trp Met
            35                  40                  45

Gly Gly Ile Ile Pro Ile Leu Gly Ile Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Thr Gly Gly Ser Gly Ser Tyr Ala Phe Asp Ile Trp Gly Gln Gly
            100                 105                 110

Thr Met Val Thr Val Ser Ser
            115

<210> SEQ ID NO 18
<211> LENGTH: 109
<212> TYPE: PRT
<213> ORGANISM: Artificial Sequence
<220> FEATURE:
<223> OTHER INFORMATION: Synthetic

<400> SEQUENCE: 18

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Ser Tyr Thr Phe Gly Gln Gly Thr Lys Leu Glu Ile Lys
            100                 105

<210> SEQ ID NO 19
<211> LENGTH: 4
<212> TYPE: PRT
<213> ORGANISM: Artificial Sequence
<220> FEATURE:
<223> OTHER INFORMATION: Synthetic

<400> SEQUENCE: 19

Ala Ala Ala Ala
1

<210> SEQ ID NO 20
<211> LENGTH: 8
<212> TYPE: PRT
<213> ORGANISM: Artificial Sequence
<220> FEATURE:
<223> OTHER INFORMATION: Synthetic

<400> SEQUENCE: 20

Gly Gly Thr Phe Ser Ser Tyr Ala
1               5

```
<210> SEQ ID NO 21
<211> LENGTH: 8
<212> TYPE: PRT
<213> ORGANISM: Artificial Sequence
<220> FEATURE:
<223> OTHER INFORMATION: Synthetic

<400> SEQUENCE: 21

Ile Ile Pro Ile Leu Gly Ile Ala
1               5

<210> SEQ ID NO 22
<211> LENGTH: 12
<212> TYPE: PRT
<213> ORGANISM: Artificial Sequence
<220> FEATURE:
<223> OTHER INFORMATION: Synthetic

<400> SEQUENCE: 22

Ala Arg Gly Gly Ser Gly Ser Tyr His Met Asp Val
1               5                   10

<210> SEQ ID NO 23
<211> LENGTH: 6
<212> TYPE: PRT
<213> ORGANISM: Artificial Sequence
<220> FEATURE:
<223> OTHER INFORMATION: Synthetic

<400> SEQUENCE: 23

Gln Ser Val Ser Ser Tyr
1               5

<210> SEQ ID NO 24
<211> LENGTH: 3
<212> TYPE: PRT
<213> ORGANISM: Artificial Sequence
<220> FEATURE:
<223> OTHER INFORMATION: Synthetic

<400> SEQUENCE: 24

Asp Ala Ser
1

<210> SEQ ID NO 25
<211> LENGTH: 11
<212> TYPE: PRT
<213> ORGANISM: Artificial Sequence
<220> FEATURE:
<223> OTHER INFORMATION: Synthetic

<400> SEQUENCE: 25

Gln Gln Arg Ser Asn Trp Pro Pro Arg Ile Thr
1               5                   10

<210> SEQ ID NO 26
<211> LENGTH: 119
<212> TYPE: PRT
<213> ORGANISM: Artificial Sequence
<220> FEATURE:
<223> OTHER INFORMATION: Synthetic

<400> SEQUENCE: 26

Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30
```

```
Ala Ile Ser Trp Val Arg Gln Ala Pro Gly Gln Gly Leu Glu Trp Met
            35                  40                  45
Gly Gly Ile Ile Pro Ile Leu Gly Ile Ala Asn Tyr Ala Gln Lys Phe
 50                  55                  60
Gln Gly Arg Val Thr Ile Thr Ala Asp Glu Ser Thr Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Gly Gly Ser Gly Ser Tyr His Met Asp Val Trp Gly Lys Gly
            100                 105                 110
Thr Thr Val Thr Val Ser Ser
            115

<210> SEQ ID NO 27
<211> LENGTH: 109
<212> TYPE: PRT
<213> ORGANISM: Artificial Sequence
<220> FEATURE:
<223> OTHER INFORMATION: Synthetic

<400> SEQUENCE: 27

Glu Ile Val Leu Thr Gln Ser Pro Ala Thr Leu Ser Leu Ser Pro Gly
 1               5                  10                  15
Glu Arg Ala Thr Leu Ser Cys Arg Ala Ser Gln Ser Val Ser Ser Tyr
            20                  25                  30
Leu Ala Trp Tyr Gln Gln Lys Pro Gly Gln Ala Pro Arg Leu Leu Ile
        35                  40                  45
Tyr Asp Ala Ser Asn Arg Ala Thr Gly Ile Pro Ala Arg Phe Ser Gly
 50                  55                  60
Ser Gly Ser Gly Thr Asp Phe Thr Leu Thr Ile Ser Ser Leu Glu Pro
 65                  70                  75                  80
Glu Asp Phe Ala Val Tyr Tyr Cys Gln Gln Arg Ser Asn Trp Pro Pro
                 85                  90                  95
Arg Ile Thr Phe Gly Gln Gly Thr Arg Leu Glu Ile Lys
            100                 105

<210> SEQ ID NO 28
<211> LENGTH: 4
<212> TYPE: PRT
<213> ORGANISM: Artificial Sequence
<220> FEATURE:
<223> OTHER INFORMATION: Synthetic

<400> SEQUENCE: 28

Ala Ala Ala Ala
 1

<210> SEQ ID NO 29
<211> LENGTH: 84
<212> TYPE: PRT
<213> ORGANISM: Artificial Sequence
<220> FEATURE:
<223> OTHER INFORMATION: Synthetic

<400> SEQUENCE: 29

Phe Val Pro Val Phe Leu Pro Ala Lys Pro Thr Thr Thr Pro Ala Pro
 1               5                  10                  15
Arg Pro Pro Thr Pro Ala Pro Thr Ile Ala Ser Gln Pro Leu Ser Leu
            20                  25                  30
```

-continued

Arg Pro Glu Ala Cys Arg Pro Ala Ala Gly Gly Ala Val His Thr Arg
            35                  40                  45

Gly Leu Asp Phe Ala Cys Asp Ile Tyr Ile Trp Ala Pro Leu Ala Gly
 50                  55                  60

Thr Cys Gly Val Leu Leu Ser Leu Val Ile Thr Leu Tyr Cys Asn
65                  70                  75                  80

His Arg Asn Arg

<210> SEQ ID NO 30
<211> LENGTH: 67
<212> TYPE: PRT
<213> ORGANISM: Artificial Sequence
<220> FEATURE:
<223> OTHER INFORMATION: Synthetic

<400> SEQUENCE: 30

Ile Glu Val Met Tyr Pro Pro Pro Tyr Leu Asp Asn Glu Lys Ser Asn
 1               5                  10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
        35                  40                  45

Val Leu Ala Cys Tyr Ser Leu Leu Val Thr Val Ala Phe Ile Ile Phe
 50                  55                  60

Trp Val Arg
65

<210> SEQ ID NO 31
<211> LENGTH: 69
<212> TYPE: PRT
<213> ORGANISM: Artificial Sequence
<220> FEATURE:
<223> OTHER INFORMATION: Synthetic

<400> SEQUENCE: 31

Thr Thr Thr Pro Ala Pro Arg Pro Pro Thr Pro Ala Pro Thr Ile Ala
 1               5                  10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
        35                  40                  45

Trp Ala Pro Leu Ala Gly Thr Cys Gly Val Leu Leu Ser Leu Val
 50                  55                  60

Ile Thr Leu Tyr Cys
65

<210> SEQ ID NO 32
<211> LENGTH: 40
<212> TYPE: PRT
<213> ORGANISM: Artificial Sequence
<220> FEATURE:
<223> OTHER INFORMATION: Synthetic

<400> SEQUENCE: 32

Ser Lys Arg Ser Arg Leu Leu His Ser Asp Tyr Met Asn Met Thr Pro
 1               5                  10                  15

Arg Arg Pro Gly Pro Thr Arg Lys His Tyr Gln Pro Tyr Ala Pro Pro
            20                  25                  30

Arg Asp Phe Ala Ala Tyr Arg Ser
        35                  40

<210> SEQ ID NO 33
<211> LENGTH: 47
<212> TYPE: PRT
<213> ORGANISM: Artificial Sequence
<220> FEATURE:
<223> OTHER INFORMATION: Synthetic

<400> SEQUENCE: 33

Arg Phe Ser Val Val Lys Arg Gly Arg Lys Lys Leu Leu Tyr Ile Phe
1               5                   10                  15

Lys Gln Pro Phe Met Arg Pro Val Gln Thr Thr Gln Glu Glu Asp Gly
            20                  25                  30

Cys Ser Cys Arg Phe Pro Glu Glu Glu Glu Gly Gly Cys Glu Leu
        35                  40                  45

<210> SEQ ID NO 34
<211> LENGTH: 112
<212> TYPE: PRT
<213> ORGANISM: Artificial Sequence
<220> FEATURE:
<223> OTHER INFORMATION: Synthetic

<400> SEQUENCE: 34

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 35
<211> LENGTH: 40
<212> TYPE: PRT
<213> ORGANISM: Artificial Sequence
<220> FEATURE:
<223> OTHER INFORMATION: Synthetic

<400> SEQUENCE: 35

Ser Lys Arg Ser Arg Leu Leu His Ser Asp Tyr Met Asn Met Thr Pro
1               5                   10                  15

Arg Arg Pro Gly Pro Thr Arg Lys His Tyr Gln Pro Tyr Ala Pro Pro
            20                  25                  30

Arg Asp Phe Ala Ala Tyr Arg Ser
        35                  40

<210> SEQ ID NO 36
<211> LENGTH: 112
<212> TYPE: PRT
<213> ORGANISM: Artificial Sequence
<220> FEATURE:
<223> OTHER INFORMATION: Synthetic -continued

```
<400> SEQUENCE: 36

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 37
<211> LENGTH: 42
<212> TYPE: PRT
<213> ORGANISM: Artificial Sequence
<220> FEATURE:
<223> OTHER INFORMATION: Synthetic

<400> SEQUENCE: 37

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 38
<211> LENGTH: 112
<212> TYPE: PRT
<213> ORGANISM: Artificial Sequence
<220> FEATURE:
<223> OTHER INFORMATION: Synthetic

<400> SEQUENCE: 38

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 39
<211> LENGTH: 21
<212> TYPE: PRT
<213> ORGANISM: Artificial Sequence
```

```
<220> FEATURE:
<223> OTHER INFORMATION: Synthetic

<400> SEQUENCE: 39

Leu Leu Leu Val Thr Ser Leu Leu Leu Cys Glu Leu Pro His Pro Ala
1               5                   10                  15

Phe Leu Leu Ile Pro
            20

<210> SEQ ID NO 40
<211> LENGTH: 22
<212> TYPE: PRT
<213> ORGANISM: Artificial Sequence
<220> FEATURE:
<223> OTHER INFORMATION: Synthetic

<400> SEQUENCE: 40

Leu Leu Val Thr Ser Leu Leu Leu Cys Glu Leu Pro His Pro Ala Phe
1               5                   10                  15

Leu Leu Ile Pro Asp Thr
            20

<210> SEQ ID NO 41
<211> LENGTH: 24
<212> TYPE: PRT
<213> ORGANISM: Artificial Sequence
<220> FEATURE:
<223> OTHER INFORMATION: Synthetic

<400> SEQUENCE: 41

Met Val Leu Leu Val Thr Ser Leu Leu Leu Cys Glu Leu Pro His Pro
1               5                   10                  15

Ala Phe Leu Leu Ile Pro Asp Thr
            20

<210> SEQ ID NO 42
<211> LENGTH: 72
<212> TYPE: DNA
<213> ORGANISM: Artificial Sequence
<220> FEATURE:
<223> OTHER INFORMATION: Synthetic

<400> SEQUENCE: 42
atggttttgc tggtgacatc gcttctgttg tgcgaattgc cccatcccgc attcctcctt    60
atccccgata cg                                                        72

<210> SEQ ID NO 43
<211> LENGTH: 72
<212> TYPE: DNA
<213> ORGANISM: Artificial Sequence
<220> FEATURE:
<223> OTHER INFORMATION: Synthetic

<400> SEQUENCE: 43
atggttctgc tggtgacttc actcctgctc tgtgaacttc cccatcccgc ttttctcctg    60
atccccgaca cc                                                        72

<210> SEQ ID NO 44
<211> LENGTH: 72
<212> TYPE: DNA
<213> ORGANISM: Artificial Sequence
<220> FEATURE:
<223> OTHER INFORMATION: Synthetic
```

<400> SEQUENCE: 44

```
atggttctgc tggtgacttc actcctgctc tgtgaacttc cccatcccgc ttttctcctg    60
atccccgaca cc                                                        72
```

<210> SEQ ID NO 45
<211> LENGTH: 237
<212> TYPE: PRT
<213> ORGANISM: Artificial Sequence
<220> FEATURE:
<223> OTHER INFORMATION: Synthetic

<400> SEQUENCE: 45

Ala Glu Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Asp Glu Leu
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys Lys Asp Pro Lys
225                 230                 235

<210> SEQ ID NO 46
<211> LENGTH: 711
<212> TYPE: DNA
<213> ORGANISM: Artificial Sequence
<220> FEATURE:
<223> OTHER INFORMATION: Synthetic

<400> SEQUENCE: 46

```
gctgaaccca gtcatgcga taagacccac acttgtccac cctgtccagc ccctgaactg    60
ctcggaggtc cgtcagtgtt tcttttcccg ccaaagccta aggacactct gatgatctct   120
cggacccctg aagtgacttg cgtcgtcgtg gacgtgtcac acgaggatcc gaggtgaag   180
```

```
ttcaactggt atgtggacgg ggtggaagtg cataatgcta agaccaagcc cagggaggaa    240
caatacaact caacctaccg cgtggtgtcc gtgctcaccg tccttcatca agactggctg    300
aacggaaaag agtataagtg caaagtctcc aataaggctc tgccagcccc tatcgaaaag    360
accatttcaa aggccaaggg gcagcctaga gagcccaag tgtacaccct tcctccctca     420
agagatgagc tcactaagaa tcaggtcagc ctgacttgtc ttgtgaaagg cttctatccc    480
agcgatattg ccgtcgaatg ggaaagcaat ggacaaccag agaacaacta caagaccacc    540
ccgcctgtgc tggactccga cggctctttc ttcctttact caaagctgac cgtcgataag    600
agccggtggc aacaggggaa tgtgttcagc tgctccgtca tgcacgaggc tctccataac    660
cactacaccc agaaaagcct gtctctttct ccgggcaaaa aggacccaaa g              711
```

<210> SEQ ID NO 47
<211> LENGTH: 219
<212> TYPE: PRT
<213> ORGANISM: Artificial Sequence
<220> FEATURE:
<223> OTHER INFORMATION: Synthetic

<400> SEQUENCE: 47

Ile Glu Val Met Tyr Pro Pro Tyr Leu Asp Asn Glu Lys Ser Asn
1               5                   10                  15

Gly Thr Ile Ile His Val Lys Gly Lys His Leu Cys Pro Ser Pro Leu
                20                  25                  30

Phe Pro Gly Pro Ser Lys Pro Phe Trp Val Leu Val Val Gly Gly
            35                  40                  45

Val Leu Ala Cys Tyr Ser Leu Leu Val Thr Val Ala Phe Ile Ile Phe
50                      55                      60

Trp Val Arg Ser Lys Arg Ser Arg Leu Leu His Ser Asp Tyr Met Asn
65                  70                  75                  80

Met Thr Pro Arg Arg Pro Gly Pro Thr Arg Lys His Tyr Gln Pro Tyr
                85                  90                  95

Ala Pro Pro Arg Asp Phe Ala Ala Tyr Arg Ser Arg Val Lys Phe Ser
            100                 105                 110

Arg Ser Ala Asp Ala Pro Ala Tyr Gln Gln Gly Gln Asn Gln Leu Tyr
        115                 120                 125

Asn Glu Leu Asn Leu Gly Arg Arg Glu Glu Tyr Asp Val Leu Asp Lys
    130                 135                 140

Arg Arg Gly Arg Asp Pro Glu Met Gly Gly Lys Pro Arg Arg Lys Asn
145                 150                 155                 160

Pro Gln Glu Gly Leu Tyr Asn Glu Leu Gln Lys Asp Lys Met Ala Glu
                165                 170                 175

Ala Tyr Ser Glu Ile Gly Met Lys Gly Glu Arg Arg Arg Gly Lys Gly
            180                 185                 190

His Asp Gly Leu Tyr Gln Gly Leu Ser Thr Ala Thr Lys Asp Thr Tyr
        195                 200                 205

Asp Ala Leu His Met Gln Ala Leu Pro Pro Arg
    210                 215

<210> SEQ ID NO 48
<211> LENGTH: 223
<212> TYPE: PRT
<213> ORGANISM: Artificial Sequence
<220> FEATURE:
<223> OTHER INFORMATION: Synthetic

<400> SEQUENCE: 48

```
Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
        35                  40                  45

Trp Ala Pro Leu Ala Gly Thr Cys Gly Val Leu Leu Leu Ser Leu Val
    50                  55                  60

Ile Thr Leu Tyr Cys Lys Arg Gly Arg Lys Lys Leu Leu Tyr Ile Phe
65                  70                  75                  80

Lys Gln Pro Phe Met Arg Pro Val Gln Thr Thr Gln Glu Glu Asp Gly
                85                  90                  95

Cys Ser Cys Arg Phe Pro Glu Glu Glu Glu Gly Gly Cys Glu Leu Arg
            100                 105                 110

Val Lys Phe Ser Arg Ser Ala Asp Ala Pro Ala Tyr Lys Gln Gly Gln
        115                 120                 125

Asn Gln Leu Tyr Asn Glu Leu Asn Leu Gly Arg Arg Glu Glu Tyr Asp
130                 135                 140

Val Leu Asp Lys Arg Arg Gly Arg Asp Pro Glu Met Gly Gly Lys Pro
145                 150                 155                 160

Arg Arg Lys Asn Pro Gln Glu Gly Leu Tyr Asn Glu Leu Gln Lys Asp
                165                 170                 175

Lys Met Ala Glu Ala Tyr Ser Glu Ile Gly Met Lys Gly Glu Arg Arg
            180                 185                 190

Arg Gly Lys Gly His Asp Gly Leu Tyr Gln Gly Leu Ser Thr Ala Thr
        195                 200                 205

Lys Asp Thr Tyr Asp Ala Leu His Met Gln Ala Leu Pro Pro Arg
    210                 215                 220
```

<210> SEQ ID NO 49
<211> LENGTH: 283
<212> TYPE: PRT
<213> ORGANISM: Artificial Sequence
<220> FEATURE:
<223> OTHER INFORMATION: Synthetic

<400> SEQUENCE: 49

```
Phe Val Pro Val Phe Leu Pro Ala Lys Pro Thr Thr Thr Pro Ala Pro
1               5                   10                  15

Arg Pro Pro Thr Pro Ala Pro Thr Ile Ala Ser Gln Pro Leu Ser Leu
            20                  25                  30

Arg Pro Glu Ala Cys Arg Pro Ala Ala Gly Gly Ala Val His Thr Arg
        35                  40                  45

Gly Leu Asp Phe Ala Cys Asp Ile Tyr Ile Trp Ala Pro Leu Ala Gly
    50                  55                  60

Thr Cys Gly Val Leu Leu Leu Ser Leu Val Ile Thr Leu Tyr Cys Asn
65                  70                  75                  80

His Arg Asn Arg Ser Lys Arg Ser Arg Leu Leu His Ser Asp Tyr Met
                85                  90                  95

Asn Met Thr Pro Arg Arg Pro Gly Pro Thr Arg Lys His Tyr Gln Pro
            100                 105                 110

Tyr Ala Pro Pro Arg Asp Phe Ala Ala Tyr Arg Ser Arg Phe Ser Val
        115                 120                 125
```

```
Val Lys Arg Gly Arg Lys Lys Leu Leu Tyr Ile Phe Lys Gln Pro Phe
    130                 135                 140
Met Arg Pro Val Gln Thr Thr Gln Glu Glu Asp Gly Cys Ser Cys Arg
145                 150                 155                 160
Phe Pro Glu Glu Glu Gly Gly Cys Glu Leu Arg Val Lys Phe Ser
                165                 170                 175
Arg Ser Ala Asp Ala Pro Ala Tyr Gln Gln Gly Gln Asn Gln Leu Tyr
            180                 185                 190
Asn Glu Leu Asn Leu Gly Arg Arg Glu Glu Tyr Asp Val Leu Asp Lys
        195                 200                 205
Arg Arg Gly Arg Asp Pro Glu Met Gly Gly Lys Pro Arg Arg Lys Asn
    210                 215                 220
Pro Gln Glu Gly Leu Tyr Asn Glu Leu Gln Lys Asp Lys Met Ala Glu
225                 230                 235                 240
Ala Tyr Ser Glu Ile Gly Met Lys Gly Glu Arg Arg Gly Lys Gly
                245                 250                 255
His Asp Gly Leu Tyr Gln Gly Leu Ser Thr Ala Thr Lys Asp Thr Tyr
            260                 265                 270
Asp Ala Leu His Met Gln Ala Leu Pro Pro Arg
        275                 280

<210> SEQ ID NO 50
<211> LENGTH: 657
<212> TYPE: DNA
<213> ORGANISM: Artificial Sequence
<220> FEATURE:
<223> OTHER INFORMATION: Synthetic

<400> SEQUENCE: 50
attgaagtta tgtatcctcc tccttaccta gacaatgaga agagcaatgg aaccattatc      60
catgtgaaag ggaaacacct tgtccaagt ccctatttc ccggaccttc taagccctt       120 tgggtgctgg tggtggttgg gggagtcctg gcttgctata gcttgctagt aacagtggcc     180
tttattattt tctgggtgag gagtaagagg agcaggctcc tgcacagtga ctacatgaac    240
atgactcccc gccgcccgg gcccaccccg aagcattacc agccctatgc ccaccacgc      300 gacttcgcag cctatcgctc cagagtgaag ttcagcagga gcgcagacgc ccccgcgtac    360
cagcagggcc agaaccagct ctataacgag ctcaatctag gacgaagaga ggagtacgat    420
gttttggaca gagacgtggc cgggaccct gagatgggg gaaagccgag aaggaagaac      480
cctcaggaag gcctgtacaa tgaactgcag aaagataaga tggcggaggc ctacagtgag    540
attgggatga aggcgagcg ccggagggc aaggggcacg atggccttta ccagggtctc      600
agtacagcca ccaaggacac ctacgacgcc cttcacatgc aggccctgcc ccctcgc       657

<210> SEQ ID NO 51
<211> LENGTH: 669
<212> TYPE: DNA
<213> ORGANISM: Artificial Sequence
<220> FEATURE:
<223> OTHER INFORMATION: Synthetic

<400> SEQUENCE: 51
accacgacgc cagcgccgcg accaccaaca ccggcgccca ccatcgcgtc gcagcccctg      60
tccctgcgcc cagaggcgtg ccggccagcg gcggggggcg cagtgcacac gaggggctg     120 gacttcgcct gtgatatcta catctgggcg cccttggccg ggacttgtgg ggtccttctc    180
ctgtcactgg ttatcaccct ttactgcaaa cggggcagaa agaaactcct gtatatattc    240
```

```
aaacaaccat ttatgagacc agtacaaact actcaagagg aagatggctg tagctgccga    300
tttccagaag aagaagaagg aggatgtgaa ctgagagtga agttcagcag gagcgcagac    360
gcccccgcgt acaagcaggg ccagaaccag ctctataacg agctcaatct aggacgaaga    420
gaggagtacg atgttttgga caagagacgt ggccgggacc ctgagatggg gggaaagccg    480
agaaggaaga accctcagga aggcctgtac aatgaactgc agaaagataa gatggcggag    540
gcctacagtg agattgggat gaaaggcgag cgccggaggg gcaaggggca cgatggcctt    600
taccagggtc tcagtacagc caccaaggac acctacgacg cccttcacat gcaggccctg    660
ccccctcgc                                                            669

<210> SEQ ID NO 52
<211> LENGTH: 849
<212> TYPE: DNA
<213> ORGANISM: Artificial Sequence
<220> FEATURE:
<223> OTHER INFORMATION: Synthetic

<400> SEQUENCE: 52
ttcgtgccgg tcttcctgcc agcgaagccc accacgacgc cagcgccgcg accaccaaca     60
ccggcgccca ccatcgcgtc gcagcccctg tccctgcgcc cagaggcgtg ccggccagcg    120 gcgggggggcg cagtgcacac gaggggggctg gacttcgcct gtgatatcta catctgggcg    180
cccttggccg ggacttgtgg ggtccttctc ctgtcactgg ttatcaccct ttactgcaac    240
cacaggaaca ggagtaagag gagcaggctc ctgcacagtg actacatgaa catgactccc    300
cgccgccccg ggcccacccg caagcattac cagccctatg ccccaccacg cgacttcgca    360
gcctatcgct cccgtttctc tgttgttaaa cggggcagaa agaagctcct gtatatattc    420
aaacaaccat ttatgagacc agtacaaact actcaagagg aagatggctg tagctgccga    480
tttccagaag aagaagaagg aggatgtgaa ctgagagtga agttcagcag gagcgcagac    540
gcccccgcgt accagcaggg ccagaaccag ctctataacg agctcaatct aggacgaaga    600
gaggagtacg atgttttgga caagagacgt ggccgggacc ctgagatggg gggaaagccg    660
agaaggaaga accctcagga aggcctgtac aatgaactgc agaaagataa gatggcggag    720
gcctacagtg agattgggat gaaaggcgag cgccggaggg gcaaggggca cgatggcctt    780
taccagggtc tcagtacagc caccaaggac acctacgacg cccttcacat gcaggccctg    840
ccccctcgc                                                            849

<210> SEQ ID NO 53
<211> LENGTH: 360
<212> TYPE: DNA
<213> ORGANISM: Artificial Sequence
<220> FEATURE:
<223> OTHER INFORMATION: Synthetic

<400> SEQUENCE: 53
caggtacagc tgcagcagtc agggggctgag gtgaagaagc ctggatcctc agtgaaggtc     60
tcctgcaagg cttctggagg caccttcagc agctatgcta tcagctgggt gcgacaggcc    120
cctggacaag ggcttgagtg gatgggaggg atcatcccta tccttggtat agcaaactac    180
gcacagaagt tccagggcag agtcacgatt accgcggacg aatccacgag cacagcctac    240
atggagctga gcagcctgag atctgaggac acggccgtgt attactgtgc gagagggcga    300
cgttcgggga gttattatat gggctactgg ggccagggaa ccctggtcac cgtctcctca    360
```

<210> SEQ ID NO 54
<211> LENGTH: 330
<212> TYPE: DNA
<213> ORGANISM: Artificial Sequence
<220> FEATURE:
<223> OTHER INFORMATION: Synthetic

<400> SEQUENCE: 54

```
gaaattgtgc tgactcagtc tccagccacc ctgtctctgt ctccagggga aagagccacc    60
ctctcctgta gggccagtca gagtgttagc agtaaccttg cctggtacca gcagaaacct   120
gggcaggctc ccaggctcct catctatgat acatccacga gggccactgg tatcccagcc   180
aggttcagtg gcagtgggtc agggacagaa ttcactctca ccataagcag cctacagtct   240
gaagattttg cagtttatta ctgtcagcag tataataact ggcctccggc gtacactttt   300
ggccagggga ccaagctgga aatcaaacgt                                     330
```

<210> SEQ ID NO 55
<211> LENGTH: 386
<212> TYPE: DNA
<213> ORGANISM: Artificial Sequence
<220> FEATURE:
<223> OTHER INFORMATION: Synthetic

<400> SEQUENCE: 55

```
caggtacagc tgcagcagtc aggggctgag gtgaagaagc ctgggtcctc ggtgaaggtc    60
tcctgcaagg cttctggagg caccttcagc agctatgcta tcagctgggt gcgacaggcc   120
cctggacaag gcttgagtg gatgggaggg atcatcccta tccttggtat agcaaactac   180
gcacagaagt tccagggcag agtcacgatt accgcggacg aatccacgag cacagcctac   240
atggagctga gcagcctgag atctgaggac acggccgtgt attactgtgc aacaggtggt   300
tcggggagtt atgcttttga tatctggggc caagggacaa tggtcaccgt ctcttcagga   360
ggtggcgggt ctggtggagg cgctag                                        386
```

<210> SEQ ID NO 56
<211> LENGTH: 330
<212> TYPE: DNA
<213> ORGANISM: Artificial Sequence
<220> FEATURE:
<223> OTHER INFORMATION: Synthetic

<400> SEQUENCE: 56

```
gaaattgtgt tgacgcagtc tccagccacc ctgtccttgt ctccagggga aagagccacc    60
ctctcctgca gggccagtca gagtgttagc agctacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg cagtttatta ctgtcagcag cgtagcaact ggcctccctc gtacactttt   300
ggccagggga ccaagctgga gatcaaacgt                                     330
```

<210> SEQ ID NO 57
<211> LENGTH: 357
<212> TYPE: DNA
<213> ORGANISM: Artificial Sequence
<220> FEATURE:
<223> OTHER INFORMATION: Synthetic

```
<400> SEQUENCE: 57
caggtacagc tgcagcagtc aggggctgag gtgaagaagc ctggatcctc agtgaaggtc        60
tcctgcaagg cttctggagg caccttcagc agctatgcta tcagctgggt gcgacaggcc       120
cctggacaag gcttgagtg gatgggaggg atcatcccta tccttggtat agcaaactac        180
gcacagaagt tccagggcag agtcacgatt accgcggacg aatccacgag cacagcctac       240
atggagctga gcagcctgag atctgaggac acggccgtgt attactgtgc gagggggt         300 tcggggagtt accatatgga cgtctggggc aaagggacca cggtcaccgt gagctca          357

<210> SEQ ID NO 58
<211> LENGTH: 330
<212> TYPE: DNA
<213> ORGANISM: Artificial Sequence
<220> FEATURE:
<223> OTHER INFORMATION: Synthetic

<400> SEQUENCE: 58
gaaattgtgt tgacgcagtc tccagccacc ctgtctttgt ctccagggga aagagccacc        60
ctctcctgca gggccagtca gagtgttagc agctacttag cctggtacca acagaaacct       120
ggccaggctc ccaggctcct catctatgat gcatccaaca gggccaccgg catcccagcc       180
aggttcagtg gcagtgggtc tgggacagac ttcactctca ccatcagcag cctagagcct       240
gaagattttg cagtttatta ctgtcagcag cgtagcaact ggcctccgcg gatcaccttc       300
ggccaaggga cacgactgga gattaaacgt                                        330

<210> SEQ ID NO 59
<211> LENGTH: 45
<212> TYPE: DNA
<213> ORGANISM: Artificial Sequence
<220> FEATURE:
<223> OTHER INFORMATION: Synthetic

<400> SEQUENCE: 59
ggaggtggcg ggtctggtgg aggcggtagc ggtggtggcg gatcc                        45
```